(12) United States Patent
Urgaonkar et al.

(10) Patent No.: US 11,739,079 B2
(45) Date of Patent: Aug. 29, 2023

(54) POLYMORPHISMS OF HM30181 MESYLATE

(71) Applicant: ATHENEX R&D, LLC, Buffalo, NY (US)

(72) Inventors: Sameer Urgaonkar, Williamsville, NY (US); Michael P. Smolinski, Amherst, NY (US); Johnson Yiu-Nam Lau, Houston, TX (US)

(73) Assignee: ATHENEX R&D. LLC, Buffalo, NY (US)

( * ) Notice: Subject to any disclaimer, the term of this patent is extended or adjusted under 35 U.S.C. 154(b) by 0 days.

(21) Appl. No.: 17/513,448

(22) Filed: Oct. 28, 2021

(65) Prior Publication Data
US 2023/0076079 A1 Mar. 9, 2023

Related U.S. Application Data

(60) Provisional application No. 63/107,720, filed on Oct. 30, 2020, provisional application No. 63/107,792, filed on Oct. 30, 2020.

(51) Int. Cl.
*A61K 45/06* (2006.01)
*C07D 405/14* (2006.01)

(52) U.S. Cl.
CPC ............ *C07D 405/14* (2013.01); *A61K 45/06* (2013.01); *C07B 2200/13* (2013.01)

(58) Field of Classification Search
CPC .... C07B 2200/13; C07D 405/14; A61K 45/06
See application file for complete search history.

(56) References Cited

FOREIGN PATENT DOCUMENTS

| WO | 2014092489 | 6/2014 |
| WO | 2020168144 | 8/2020 |
| WO | 2020194175 | 10/2020 |

(Continued)

OTHER PUBLICATIONS

International Search Report dated Feb. 28, 2022, from related PCT application No. PCT/US21/57046. 13 pages.

(Continued)

*Primary Examiner* — Joseph K McKane
*Assistant Examiner* — David M Shim
(74) *Attorney, Agent, or Firm* — Fish IP Law, LLP

(57) ABSTRACT

HM30181 (shown below) can be used to improve absorption of cancer chemotherapy drugs, such as paclitaxel. Herein are described various polymorphisms of HM30181, in particular polymorphism C, as well as their physical properties and methods for their preparation and characterization.

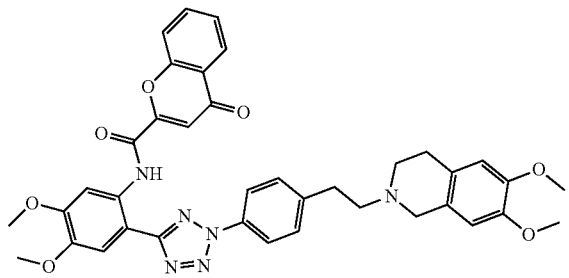

2 Claims, 33 Drawing Sheets

(56) References Cited

FOREIGN PATENT DOCUMENTS

WO     WO 2020/194175 A1 * 10/2020 ............... A61K 9/00

OTHER PUBLICATIONS

Finch, et al. "P-glycoprotein and its role in drug-drug interactions," Australian Prescriber vol. 37:No. 4:Aug. 2014. 3 pages.
Caira, Mino R. "Crystalline Polymorphism of Organic Compounds," Topics in Chemistry, vol. 198. 1998. 46 pages.
Pires, et al. "Inhibition of P-Glycoprotein-Mediated Paclitaxel Resistance by Reversibly Linked Quinine Homodimers," Molecular Pharmacology. Jan. 2009; 75(1): 92-100. 17 pages.

* cited by examiner

POLYMORPHISMS OF HM30181 MESYLATE

This application claims the benefit of U.S. Provisional Patent Application No. 63/107,720 filed on Oct. 30, 2020, and Provisional Patent Application No. 63/107,792 filed on Oct. 30, 2020. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is P-glycoprotein inhibitors, in particular HM30181 mesylate.

BACKGROUND

The background description includes information that may be useful in understanding the present invention. It is not an admission that any of the information provided herein is prior art or relevant to the presently claimed invention, or that any publication specifically or implicitly referenced is prior art.

P-glycoprotein (P-gp) is an ATP dependent efflux pump protein with a wide range of substrate specificity that is found throughout the major genera. Due to its broad distribution and its function it is thought to be a defense mechanism that actively transport toxins out of cells. In humans P-gp can transport substrate compounds from intestinal epithelial cells back into the intestinal lumen, from the blood brain barrier back into adjacent capillaries, from the proximal tubule of the kidney into the urinary filtrate, and from liver cells into the bile ducts.

Unfortunately, a number of drugs utilized in chemotherapy are substrates for P-gp. P-gp activity, therefore, can reduce bioavailability and effectiveness of chemotherapeutic drugs. In such instances administration of P-gp inhibitors can be useful in improving the response to chemotherapy. Accordingly, over the last 30 years a number of pharmaceutically useful P-gp inhibitors (such as amiodarone, clarithromycin, cyclosporin, colchicine, diltiazem, erythromycin, felodipine, ketoconazole, lansoprazole, omeprazole, nifedipine, paroxetine, reserpine, saquinavir, sertraline, quinidine, tamoxifen, verapamil, and duloxetine) have been developed.

HM30181 mesylate is a third generation P-gp inhibitor that has been studied for use with paclitaxel. HM30181 mesylate selectively inhibits P-gp in the intestinal epithelium, improving absorption of orally administered chemotherapeutic drugs without increasing potentially detrimental transport across the blood-brain barrier. The structure of HM30181 mesylate is shown below.

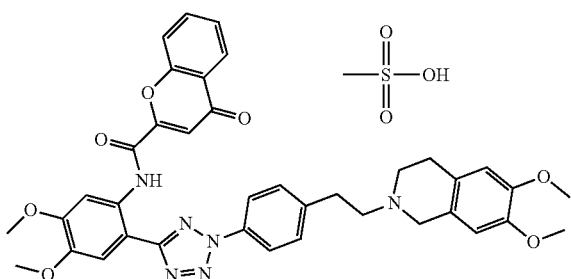

The pharmacokinetics, bioavailability, and incidence of side effects of orally administered HM30181 mesylate are less than optimal, however.

Thus, there is still a need for polymorphisms of HM30181 mesylate that can provide improved absorption, improved pharmacokinetics, and/or reduced side effects upon administration.

SUMMARY OF THE INVENTION

The inventive subject matter provides polymorphisms of HM31081 mesylate, methods for their preparation and characterization, and methods for their use.

One embodiment of the inventive concept is a composition that includes a crystalline or partially crystalline form of HM30181 mesylate, where the crystalline or partially crystalline form includes polymorph B, polymorph C, polymorph D, polymorph E, polymorph F, polymorph G, polymorph H, polymorph I, polymorph J, polymorph K, polymorph L, polymorph M, and/or polymorph N. In some of such embodiments the crystalline or partially crystalline form is polymorph B, and has an X-ray diffraction pattern corresponding to FIG. 40 and an endotherm at about 159.92° C. In some of such embodiments the crystalline or partially crystalline form is polymorph Type C, and has an X-ray diffraction pattern corresponding to FIG. 42 and an endotherm at about 159.6° C. In some of such embodiments the crystalline or partially crystalline form is polymorph Type C, and the crystalline form has an X-ray diffraction pattern with 2Theta maxima at about 6.4° and about 8.0°. In some of such embodiments the crystalline or partially crystalline form is polymorph Type C, and has a unit cell with a volume of about 1180 Å$^3$, where a is about 7 Å, b is about 15 Å, c is about 18 Å, alpha is about 52°, beta is about 62°, and gamma is about 90°. In some of such embodiments the crystalline or partially crystalline form is polymorph C, and has an X-ray diffraction pattern corresponding to FIG. 42 and an endotherm at about 159.60° C., and can be a monohydrate. In some of such embodiments the crystalline or partially crystalline form is polymorph D, and has an X-ray diffraction pattern corresponding to FIG. 45 and an endotherm at about 66.97° C. In some of such embodiments the crystalline or partially crystalline form is polymorph E, and has an X-ray diffraction pattern corresponding to FIG. 47 and an endotherm at about 154.42° C., and can include DMA. In some of such embodiments the crystalline or partially crystalline form is polymorph Type E, and has an X-ray diffraction pattern corresponding to FIG. 47 and an endotherm at about 154.4° C. In some of such embodiments the crystalline or partially crystalline form is polymorph Type E, and has an X-ray diffraction pattern comprising 2Theta maxima at about 4.2°, about 10.4°, about 10.7°, about 14.7°, about 16.8°, about 21°, about 23.8°, about 26.6°, and about 27.7°. In some of such embodiments the crystalline or partially crystalline form is polymorph Type E, and has a unit cell with a volume of about 1620 Å$^3$, where a is about 8 Å, b is about 10 Å, c is about 24 Å, alpha is about 75°, beta is about 80°, and gamma is about 110°. In some of such embodiments the crystalline or partially crystalline form is polymorph F, and has an X-ray diffraction pattern corresponding to FIG. 50 has an endotherm at about 148.41° C., and can include DMF. In some of such embodiments the crystalline or partially crystalline form is polymorph G, and has an X-ray diffraction pattern corresponding to FIG. 53 and an endotherm at about 69.02° C. In some of such embodiments the crystalline or partially crystalline form is polymorph H, and has an X-ray diffraction pattern corresponding to FIG.

55 and an endotherm at about 126.52° C. In some of such embodiments the crystalline or partially crystalline form is polymorph I, and has an X-ray diffraction pattern corresponding to FIG. 57. In some of such embodiments the crystalline or partially crystalline form is polymorph J, and has an X-ray diffraction pattern corresponding to FIG. 58. In some of such embodiments the crystalline or partially crystalline form is polymorph K, and has an X-ray diffraction pattern corresponding to FIG. 60. In some of such embodiments the crystalline or partially crystalline form is polymorph L, and has an X-ray diffraction pattern corresponding to FIG. 61. In some of such embodiments the crystalline or partially crystalline form is polymorph M, and has an X-ray diffraction pattern corresponding to FIG. 62. In some of such embodiments the crystalline or partially crystalline form is polymorph N, has an X-ray diffraction pattern corresponding to FIG. 63 and an endotherms at about 159° C. and about 188° C., and can include methanol.

Another embodiment of the inventive concept is a method of inhibiting P-glycoprotein activity, by contacting P-glycoprotein with at least one crystalline or partially crystalline form of HM30181 mesylate as described above in an amount that is effective in inhibiting an activity of P-glycoprotein.

Another embodiment of the inventive concept is a method of treating cancer by administering a chemotherapeutic drug that is a P-glycoprotein substrate to an individual that in need of treatment for cancer and also administering a polymorph of HM30181 mesylate as described above in an amount that is effective to inhibit P-glycoprotein activity in the individual.

Another embodiment of the inventive concept is the use of a polymorph of HM30181 mesylate as described above in preparing a medicament for treating cancer. Such a medicament can also include a chemotherapeutic drug that is a P-glycoprotein substrate.

Another embodiment of the inventive concept is a formulation that includes a polymorph of HM30181 mesylate as described above and a therapeutic drug, where the therapeutic drug is a P-glycoprotein substrate. Such a therapeutic drug can be a chemotherapeutic drug that is used in the treatment of cancer.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 shows an overlay of X-Ray Powder Diffraction (XRPD) results from HM30181 mesylate polymorphisms types A to N.

FIG. 2 shows results from XRPD studies of HM30181 mesylate Type A starting material FIG. 3 shows an overlay of results of DSC/TGA studies of HM30181 mesylate Type A.

FIG. 4 shows results of $^1$H-NMR studies of HM30181 mesylate Type A.

FIG. 5 shows results of DVS of HM30181 mesylate Type A starting material.

FIG. 6 shows an overlay of overlay of XRPD studies of Type A starting material post-DVS.

FIG. 7 shows an overlay of results from Cyclic DSC studies of HM30181 mesylate Type A and HM30181 mesylate Type A heated to 110° C.

FIG. 8 shows an overlay of results of XRPD studies of HM30181 mesylate Type A and HM30181 mesylate Type A heated to 110° C.

FIG. 9 shows an overlay of cyclic DSC studies of HM30181 mesylate Type A starting material and HM30181 mesylate Type A heated to 185° C.

FIG. 10 shows an overlay of XRPD studies of HM30181 mesylate Type A starting material and HM30181 mesylate Type A heated to 185° C.

FIG. 11 shows an overlay of results of cyclic DSC studies of HM30181 mesylate Type A starting material and HM30181 mesylate Type A heated to 200° C.

FIG. 12 shows an overlay of results of XRPD studies of HM30181 mesylate Type A starting material and HM30181 mesylate Type A heated to 200° C.

FIG. 13 shows results of XRPD studies of freebase HM3018-A

FIG. 14 shows an overlay of results of $^1$H-NMR studies of HM30181 mesylate Type A heated to 200° C., freebase HM3018-A, and HM30181 mesylate Type A starting material.

FIG. 15 shows an overlay of results of XRPD studies of HM30181 mesylate Type B from slurry experiments.

FIG. 16 shows an overlay of results of XRPD studies of HM30181 mesylate Type C from slurry experiments.

FIG. 17 shows an overlay of results of XRPD studies of HM30181 mesylate Type D from slurry experiments.

FIG. 18 shows an overlay of results of XRPD studies of HM30181 mesylate Type E from slurry experiments.

FIG. 19 shows an overlay of results of XRPD of HM30181 mesylate Type F from slurry experiments.

FIG. 20 shows an overlay of results of XRPD studies of HM30181 mesylate Type G from slurry experiments.

FIG. 21 shows an overlay of results of XRPD studies of HM30181 mesylate Type D from liquid vapor diffusion experiments.

FIG. 22 shows an overlay of results of XRPD studies of HM30181 mesylate Type E from liquid vapor diffusion experiments.

FIG. 23 shows an overlay of results of XRPD studies of HM30181 mesylate Type H from liquid vapor diffusion experiments.

FIG. 24 shows an overlay of results of XRPD studies of HM30181 mesylate Type I and HM30181 mesylate Type J from liquid vapor diffusion experiments.

FIG. 25 shows an overlay of results of XRPD studies of HM30181 mesylate Type C polymorph generated by cooling.

FIG. 26 shows an overlay of results of XRPD studies of HM30181 mesylate Type C with samples from anti-solvent experiments.

FIG. 27 shows an overlay of results of XRPD studies of HM30181 mesylate Type F with sample from anti-solvent experiments.

FIG. 28 shows an overlay of results of XRPD studies of HM30181 mesylate Type J with samples from anti-solvent experiments.

FIG. 29 shows an overlay of results of XRPD studies of HM30181 mesylate Type K from anti-solvent experiments.

FIG. 30 shows an overlay of results of XRPD studies of HM30181 mesylate Type L from anti-solvent experiments.

FIG. 31 shows an overlay of results of XRPD studies of HM30181 mesylate Type M from anti-solvent experiments.

FIG. 32 shows an overlay of results of XRPD studies of HM30181 mesylate Type B large scale studies.

FIG. 33 shows an overlay of results of XRPD studies of HM30181 mesylate Type C large scale studies.

FIG. 34 shows an overlay of XRPD studies of HM30181 mesylate Type D large scale studies.

FIG. 35 shows an overlay of results of XRPD studies of HM30181 mesylate Type E large scale studies.

FIG. 36 shows an overlay of results of XRPD studies of HM30181 mesylate Type G large scale studies.

FIG. 37 shows an overlay of results of XRPD studies of HM30181 mesylate Type F and HM30181 mesylate Type G large scale studies.

FIG. 38 shows an overlay of results of $^1$H-NMR studies of HM30181 mesylate Type G large scale studies.

FIG. 39 shows an overlay of results of $^1$H-NMR studies HM30181 mesylate polymorphisms large scale studies.

FIG. 40 shows results of XRPD studies of HM30181 mesylate Type B.

FIG. 41 shows an overlay of DSC and TGA results from HM30181 mesylate Type B.

FIG. 42 shows results of XRPD of HM30181 mesylate Type C.

FIG. 43 shows an overlay of DSC and TGA results of HM30181 mesylate Type C.

FIG. 44 shows results of $^1$H-NMR of HM30181 mesylate Type C.

FIG. 45 shows results of XRPD of HM30181 mesylate Type D.

FIG. 46 shows an overlay of DSC and TGA results from HM30181 mesylate Type D.

FIG. 47 shows results of XRPD of HM30181 mesylate Type E.

FIG. 48 shows an overlay of results from DSC and TGA of HM30181 mesylate Type E.

FIG. 49 shows results of $^1$H-NMR of HM30181 mesylate Type E.

FIG. 50 shows results from XRPD of HM30181 mesylate Type F.

FIG. 51 shows an overlay of results from DSC and TGA of HM30181 mesylate Type F.

FIG. 52 shows results from $^1$H-NMR of HM30181 mesylate Type F

FIG. 53 shows results from XRPD of HM30181 mesylate Type G.

FIG. 54 shows an overlay of results from DSC and TGA of HM30181 mesylate Type G.

FIG. 55 shows results from XRPD of HM30181 mesylate Type H.

FIG. 56 shows an overlay of results from DSC and TGA of HM30181 mesylate Type H.

FIG. 57 shows results from XRPD of HM30181 mesylate Type I.

FIG. 58 shows results from XRPD of HM30181 mesylate Type J.

FIG. 59 shows results from TGA of HM30181 mesylate Type J.

FIG. 60 shows results from XRPD of HM30181 mesylate Type K.

FIG. 61 shows results from XRPD of HM30181 mesylate Type L.

FIG. 62 shows results from XRPD of HM30181 mesylate Type M.

FIG. 63 shows results from XRPD of HM30181 mesylate Type N.

FIG. 64 shows an overlay of DSC and TGA results from HM30181 mesylate Type N.

FIG. 65 shows results of $^1$H-NMR of HM30181 mesylate Type N.

DETAILED DESCRIPTION

Figure 1:
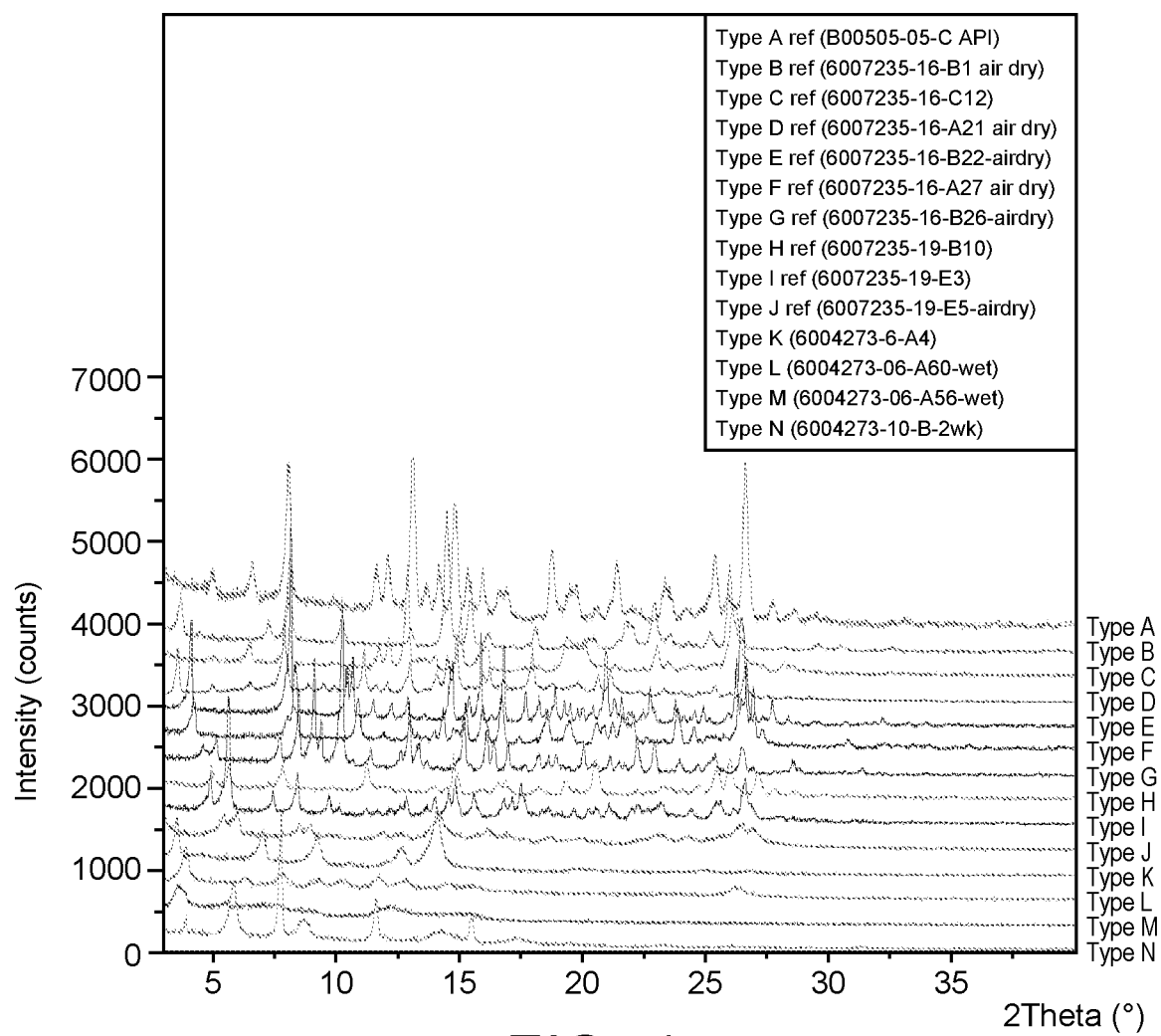
FIG. 1.

The following description includes information that may be useful in understanding the present invention. It is not an admission that any of the information provided herein is prior art or relevant to the presently claimed invention, or that any publication specifically or implicitly referenced is prior art.

The inventive subject matter provides a wide range of polymorphisms of HM30181 mesylate and methods for their preparation. The various polymorphisms are shown to be structurally distinct by X-ray diffraction and various physical properties. Polymorphs of HM30181 mesylate with improved pharmacokinetics, reduced incidence of side effects, reduced dosing schedules, etc. can be identified among these by conventional methods (e.g., animal studies, clinical studies, etc.).

One should appreciate that the disclosed techniques provide many advantageous technical effects including improving absorption of chemotherapeutic drugs while maintaining patency of the blood-brain barrier and reducing the incidence of developing drug resistance during cancer treatment.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Inventors have identified 1a number of polymorphisms of HM30181 mesylate, including Type A to Type N (see Table 1). Some of the polymorphisms can include metastable solvates. The Inventors believe that one or more of these polymorphs can have improved pharmacokinetics and/or bioavailability relative to prior art formulations of HM30181 mesylate. Inventors believe that such improvements can permit the use of lower doses that reduce or eliminate side effects associated with treatment using prior art formulations of HM30181 mesylate.

Table 1

FIG. 1 provides a summary overlay of X-Ray Powder Diffraction (XRPD) results from HM30181 mesylate polymorphisms types A to N, as provided in Table 1.

Figure 2:
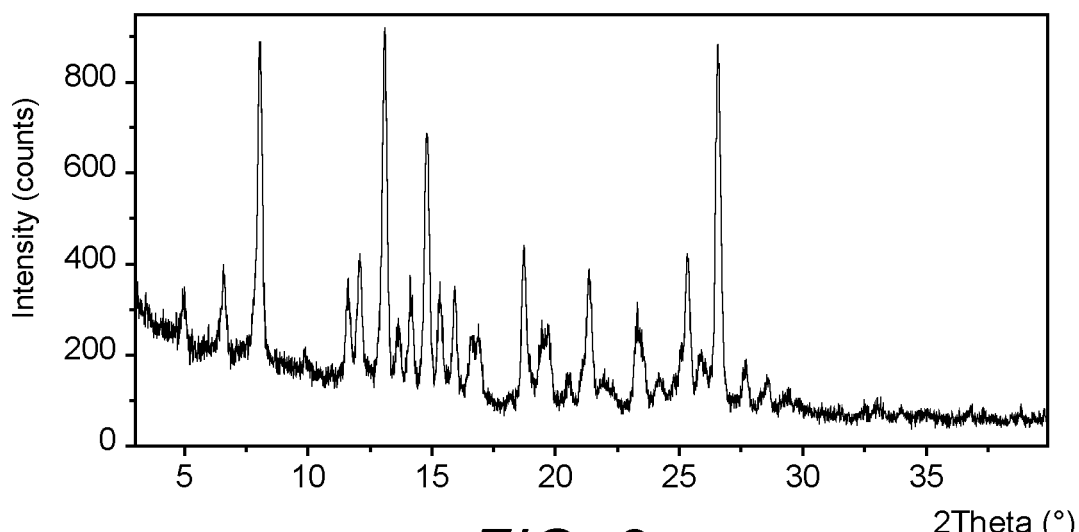
FIG. 2.

A prior art HM30181 mesylate salt monohydrate material (i.e., a starting material) can be synthesized as described in PCT application publication number WO 2005/033097 or U.S. Pat. No. 9,283,218 which are incorporated herein by reference. This starting material was characterized by XRPD, TGA, DSC, and DVS (see below), and was identified as crystalline Type A by XRPD (see FIG. 2).

Figure 3:
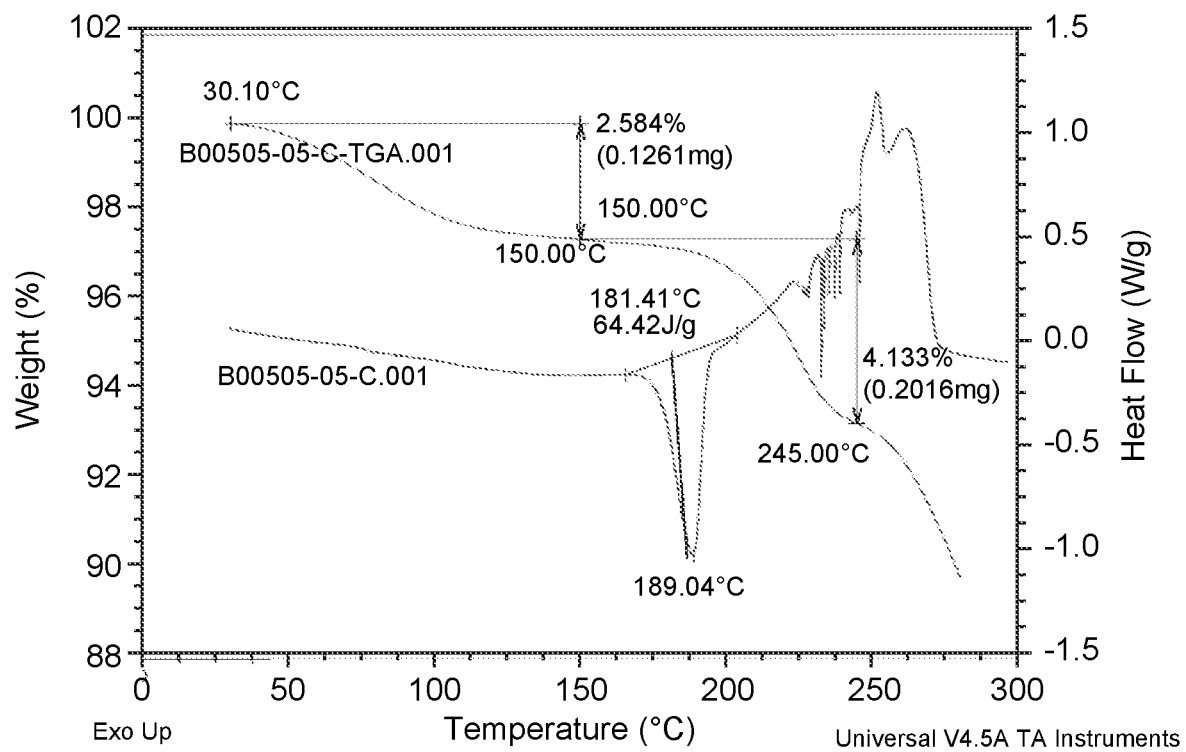
FIG. 3.
Figure 4:
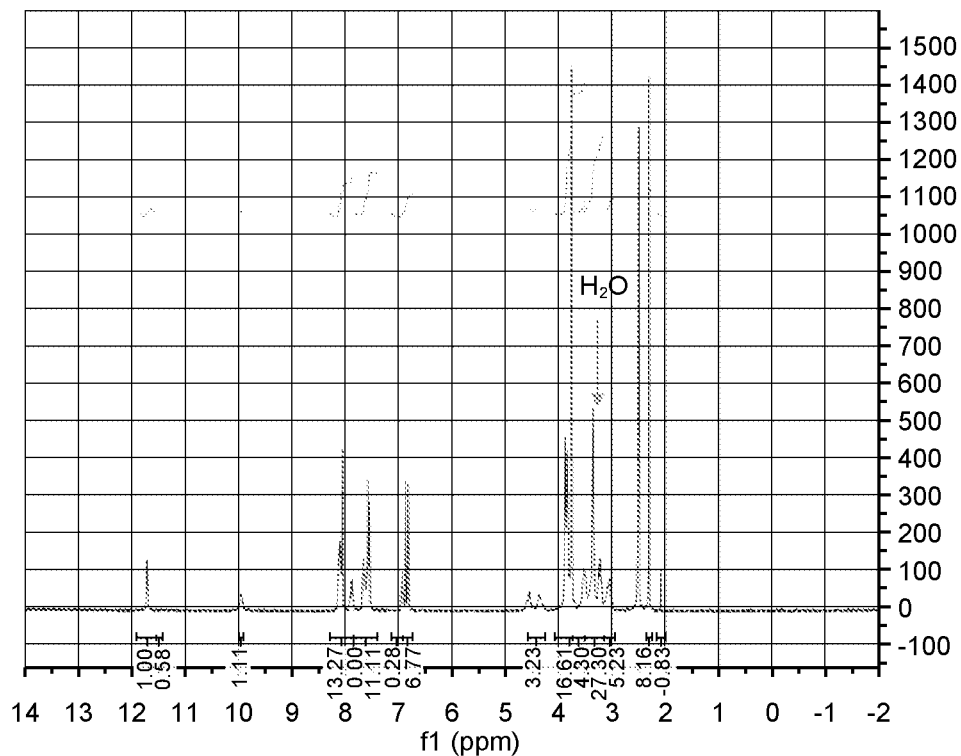
FIG. 4.

By DSC, HM30181 mesylate Type A displayed an endotherm at 181.41° C. (see FIG. 3). By TGA, HM30181 mesylate Type A showed 2.584% weight loss before 150° C., matching with a monohydrate weight loss (MW 802.849 for HM30181 mesylate salt monohydrate, 2.24% wt loss), followed by a 4.133% weight loss before 250° C., possibly due to disassociation and decomposition (see FIG. 3). By $^1$H-NMR, HM30181 mesylate Type A was potentially a hydrate, as no solvents were detected other than water (see FIG. 4).

Figure 5:
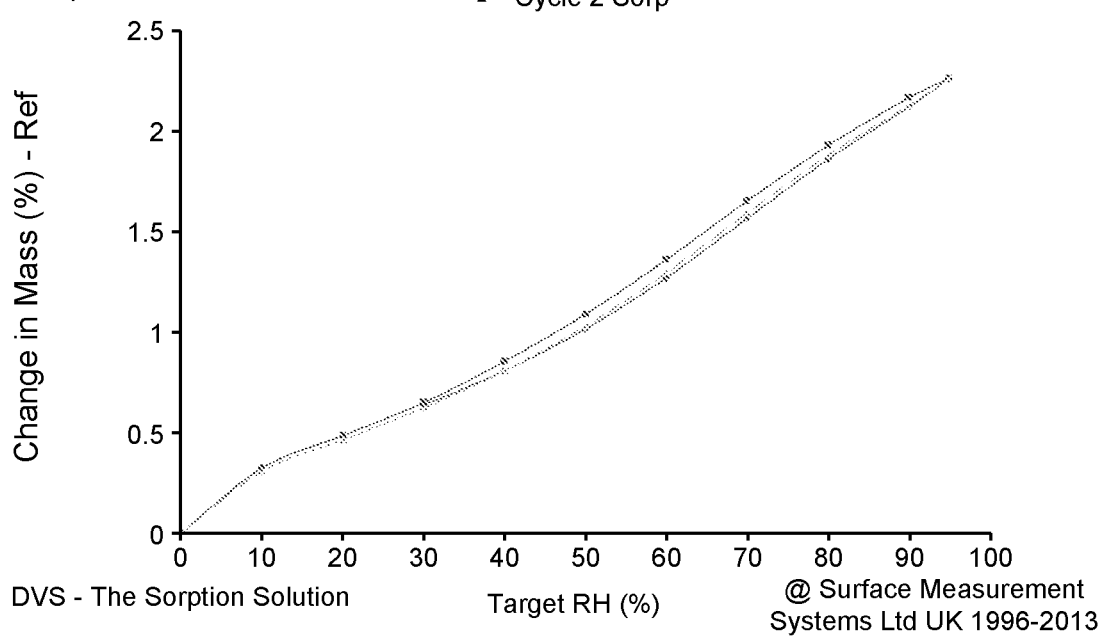
FIG. 5.
Figure 6:
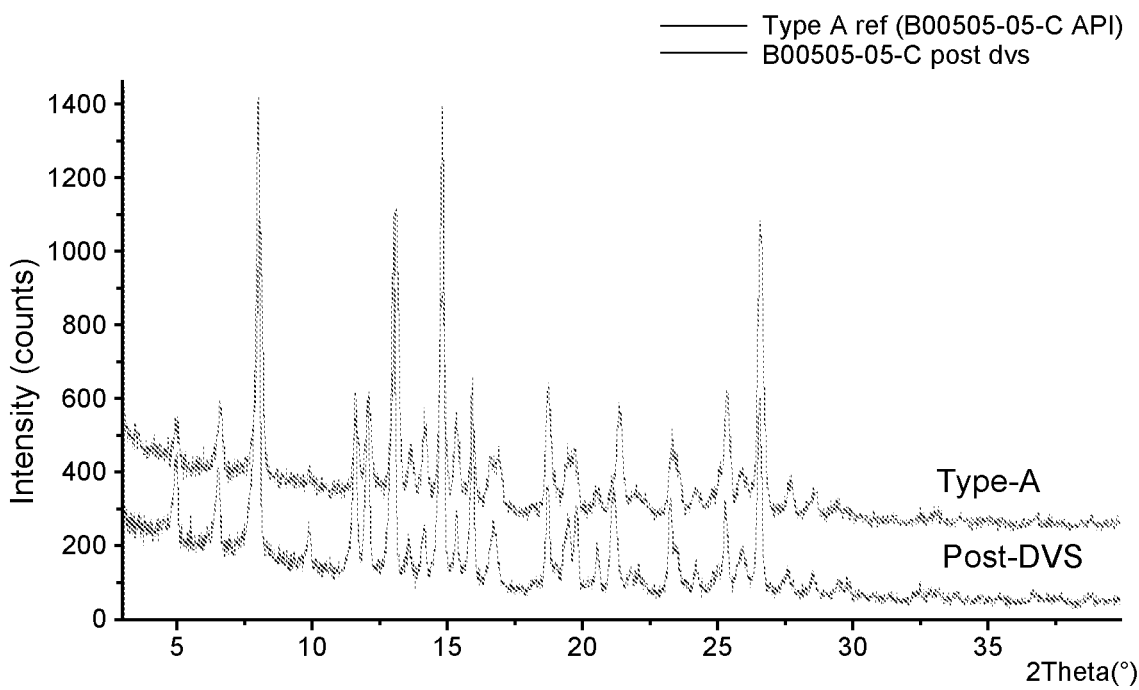
FIG. 6.

By DVS, HM30181 mesylate Type A was hygroscopic and absorbed 2.26% water from 0-95% RH, with no change in XRPD pattern observed (see FIG. 5 and FIG. 6).

Figure 7:
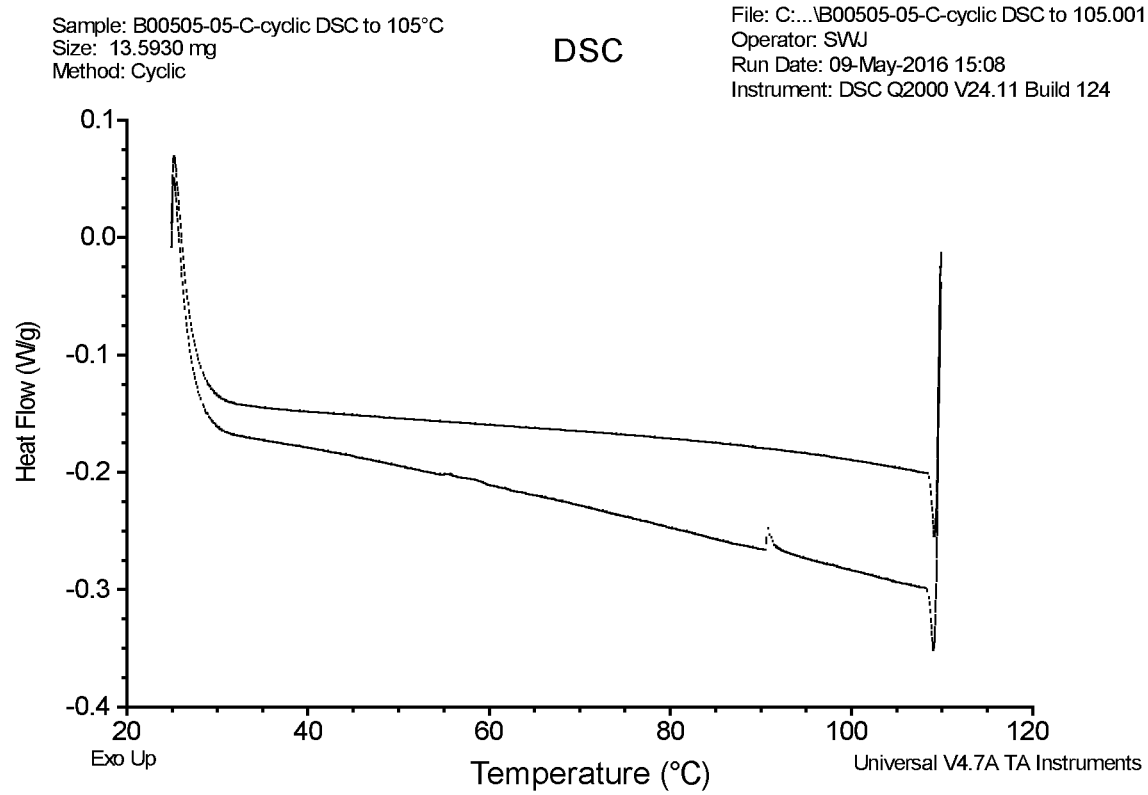
FIG. 7.
Figure 8:
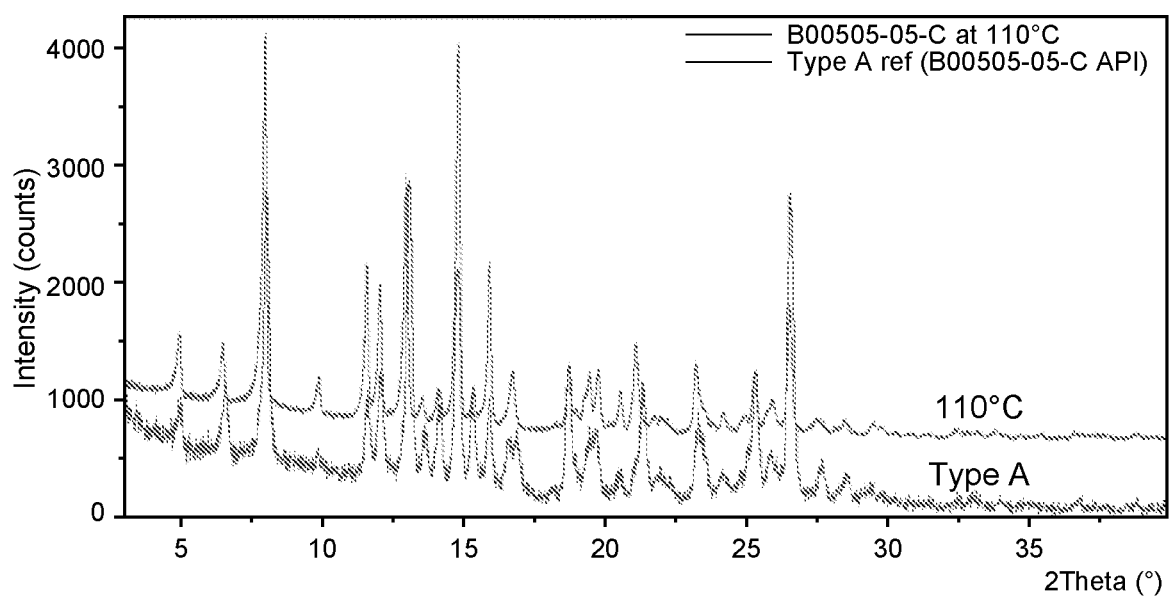
FIG. 8.
Figure 9:
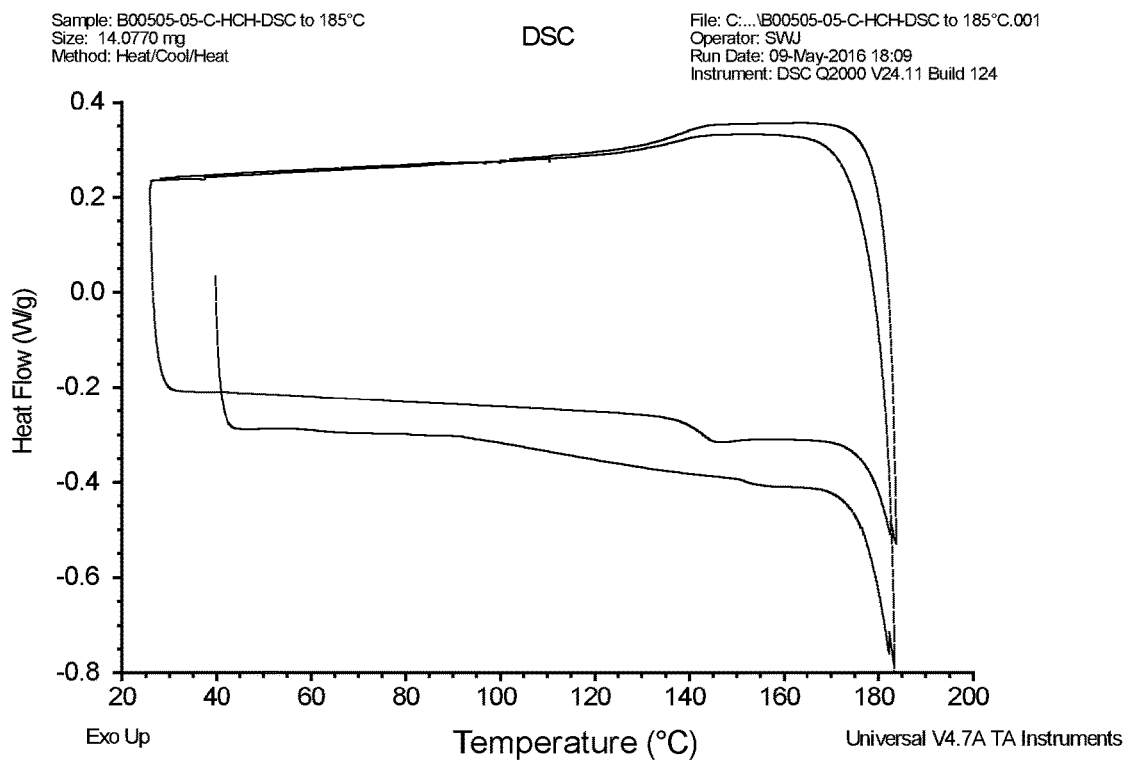
FIG. 9.
Figure 10:
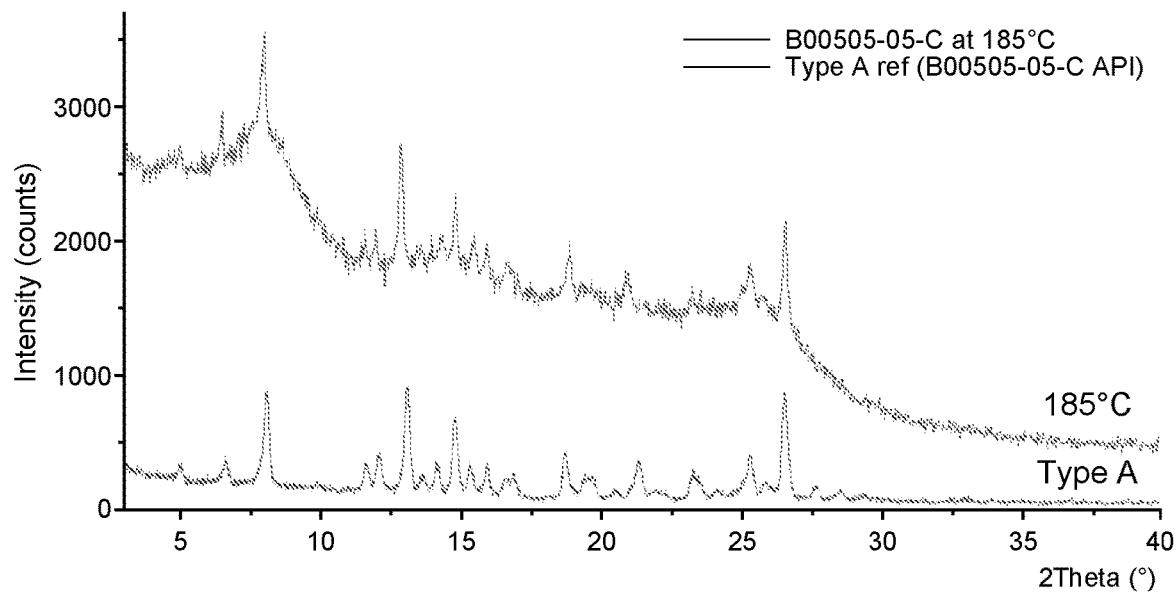
FIG. 10.
Figure 11:
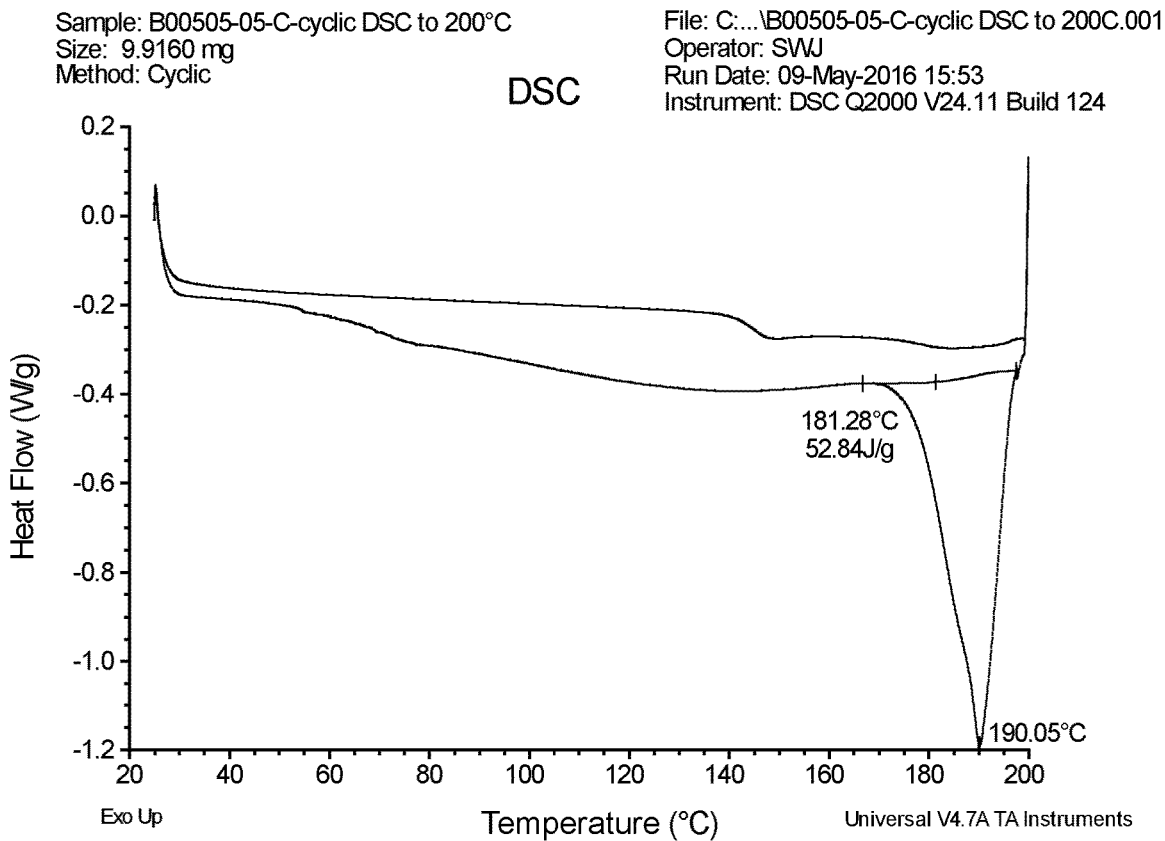
FIG. 11.
Figure 12:
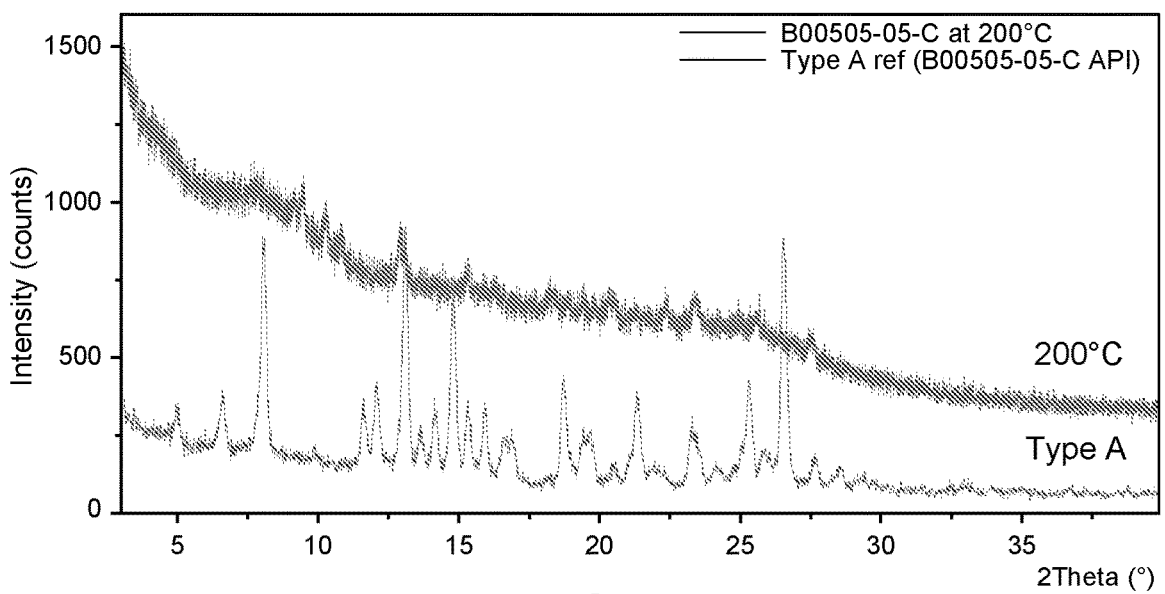
FIG. 12.
Figure 13:
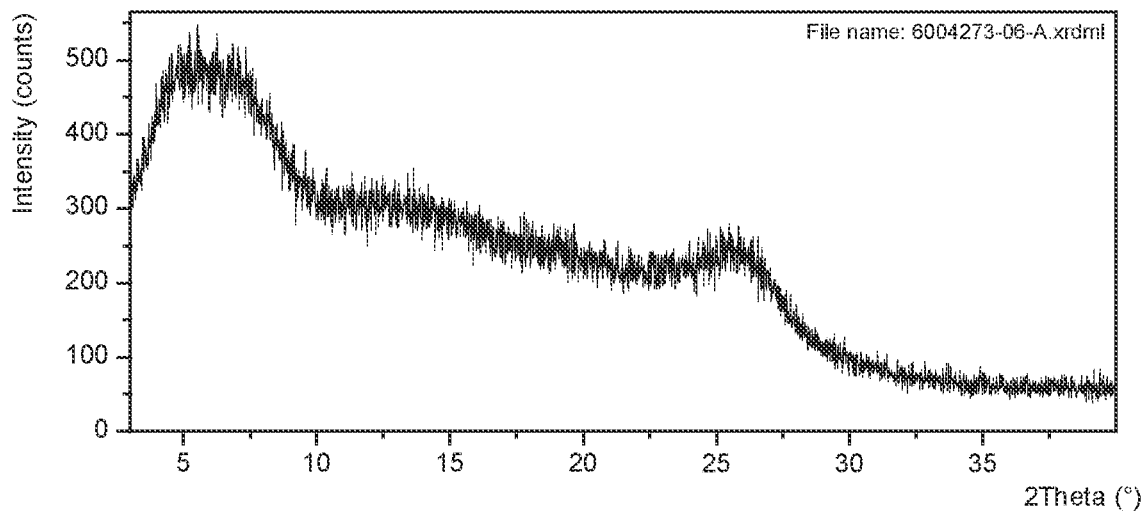
FIG. 13.
Figure 14:
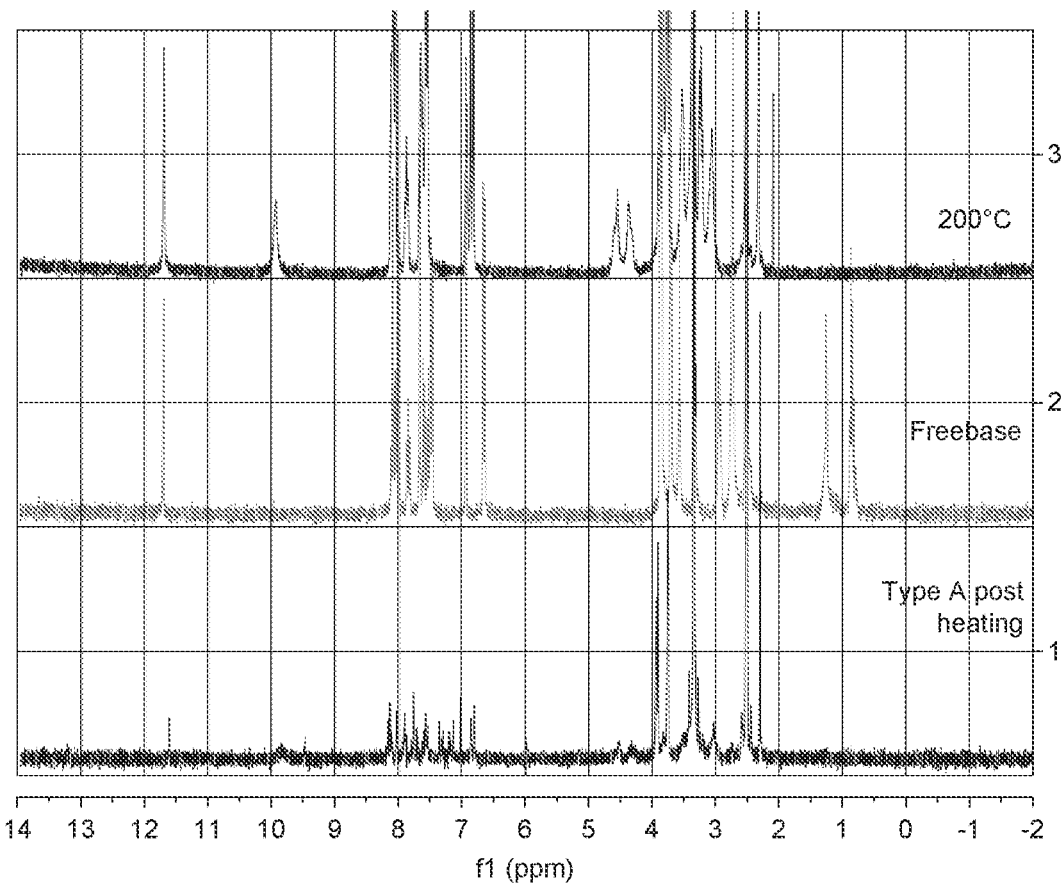
FIG. 14.

Cyclic DSC to 110° C. of HM30181 mesylate Type A resulted in no XRPD change (see FIG. 7 and FIG. 8). Cyclic DSC of HM30181 mesylate Type A to 185° C. resulted in HM30181 mesylate Type A with reduced crystallinity (FIG. 9 and FIG. 10). Cyclic DSC of HM30181 mesylate Type A to 200° C. resulted in amorphous material (see FIG. 11 and FIG. 12). Freebase HM3018-A (6004273-06-A) was also characterized by XRPD and was found to be amorphous (see FIG. 13). Based on $^1$H-NMR data, decomposition of Type A initiated after heating to 200° C. (see FIG. 14).

Solubility of HM30181 mesylate starting material was estimated in solvents (see below), and results are listed in Table 2.

TABLE 0

| Batch | Crystal form (XRPD) | DSC endotherm (° C.) | TGA weight loss | Identification |
|---|---|---|---|---|
| B00505-05-C (starting material) | Type A | 181.41 | 2.6% before 150° C. | Monohydrate (hygroscopic to 2.26% at 95% RH) |
| 6007235-16-A1-airdry | Type B | 159.92 | 1.9% before 170° C. | Solvate/hydrate |
| 6004273-10-C-vd | Type C | 159.60 | 3.0% before 175° C. | Monohydrate |
| 6007235-16-A21-airdry | Type D | 66.97 (peak), 114 (exotherm) | 14.71% before 150° C. | Solvate/hydrate |
| 6004273-10-E-vd | Type E | 154.42 | 5.247% before 168° C. | DMA solvate |
| 6004273-10-G-vd | Type F | 148.41 | 5.123% weight loss before 180° C. | DMF solvate |
| 6007235-16-B26-airdry | Type G | 69.02 233.29 | 1.451% before 150° C. | Solvate/hydrate |
| 6007235-19-B10 | Type H | 126.52 | 7.444% weight loss before 200° C. | Solvate/hydrate |
| 6007235-19-E3 | Type I | NA | NA | Weak solvate- converts to Type J on air-drying |
| 6007235-19-E5 | Type J | NA | 2.887% weight loss before 150° C. | Solvate/hydrate |
| 6004273-06-A4 | Type K | Insufficient sample | Insufficient sample | Possible solvate/hydrate |
| 6004273-06-A60 | Type L | Insufficient sample | Insufficient sample | Possible solvate/hydrate |
| 6004273-06-A56 | Type M | Insufficient sample | Insufficient sample | Possible solvate/hydrate |
| 6004273-10-B-vd | Type N | 159.28 188.47 | 2.128% weight loss before 180° C. | Possible MeOH solvate/hydrate |

TABLE 2

| Experiment ID | Solvent | Solubility (mg/mL) | Dissolved after heating to 50° C. for 2 hours? |
|---|---|---|---|
| B00505-05-C-1 | MeOH | 1.7-2.0 | |
| B00505-05-C-2 | EtOH | <0.9 | Almost |
| B00505-05-C-3 | IPA | <1.0 | No |
| B00505-05-C-4 | Acetone | <1.0 | No |
| B00505-05-C-5 | MIBK | <1.0 | No |
| B00505-05-C-6 | EtOAc | <0.9 | No |
| B00505-05-C-7 | IPOAc | <1.0 | No |
| B00505-05-C-8 | THF | <1.0 | No |
| B00505-05-C-9 | 2-MeTHF | <1.0 | No |
| B00505-05-C-10 | 1,4-Dioxane | <1.0 | No |
| B00505-05-C-11 | MTBE | <1.0 | No |
| B00505-05-C-12 | ACN | <1.0 | Yes |
| B00505-05-C-13 | DCM | <1.0 | Yes |
| B00505-05-C-14 | CHCl$_3$ | 5.0-6.7 | |
| B00505-05-C-15 | Toluene | <1.0 | No |
| B00505-05-C-16 | n-Heptane | <1.0 | No |
| B00505-05-C-17 | H$_2$O | <1.0 | No |
| B00505-05-C-18 | Cyclohexane | <1.0 | No |
| B00505-05-C-19 | MEK | <1.0 | No |
| B00505-05-C-20 | T-BuOH | <1.0 | No |
| B00505-05-C-21 | NMP | 4.8-6.3 | |
| B00505-05-C-22 | DMSO | 22-44 | |
| B00505-05-C-23 | DMA | 3.2-4.8 | |
| B00505-05-C-24 | n-Propanol | <1.0 | No |
| B00505-05-C-25 | n-Propyl acetate | <1.0 | No |
| B00505-05-C-26 | Cumene | <1.0 | No |

Slurry-based generation and/or screening for HM30181 mesylate polymorphs was performed by preparing slurries of starting material HM30181 mesylate Type A in a variety of solvents and under a variety of conditions as described below. The resulting solids were analyzed by XRPD and identified for physical state. Results are summarized in Table 3 and Table 4.

Figure 15:
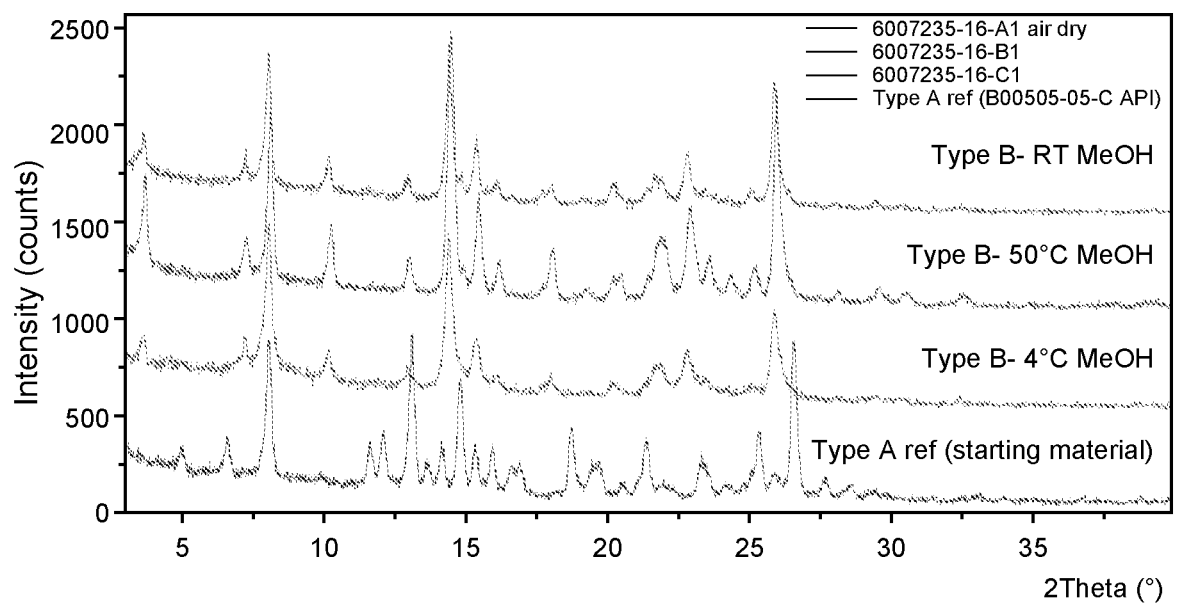
FIG. 15.
Figure 16:
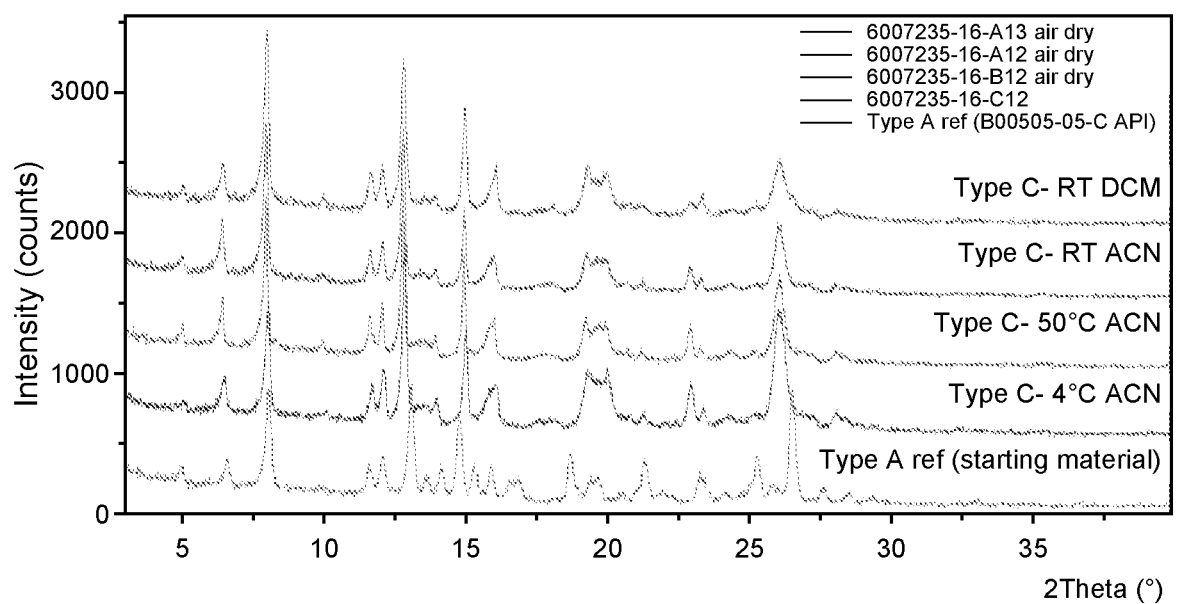
FIG. 16.
Figure 17:
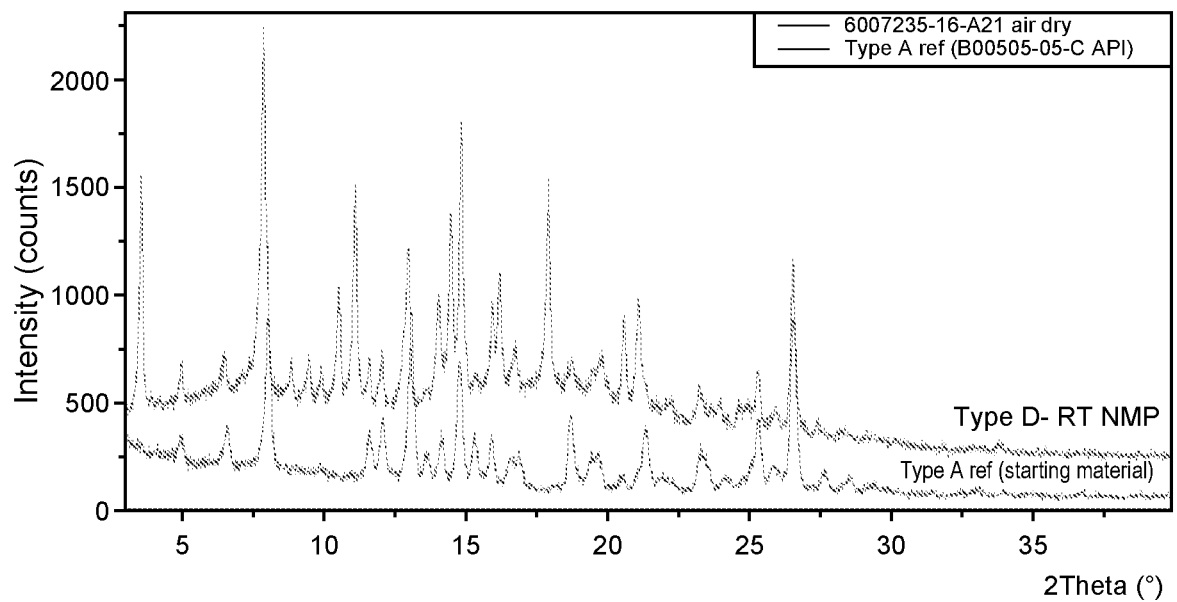
FIG. 17.
Figure 18:
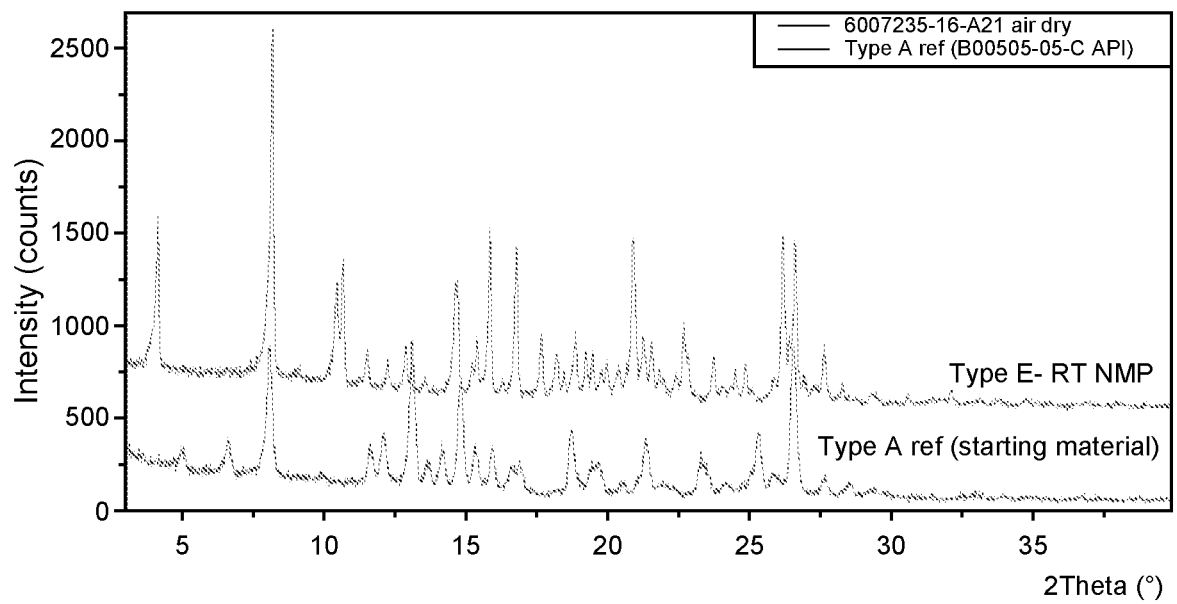
FIG. 18.
Figure 19:
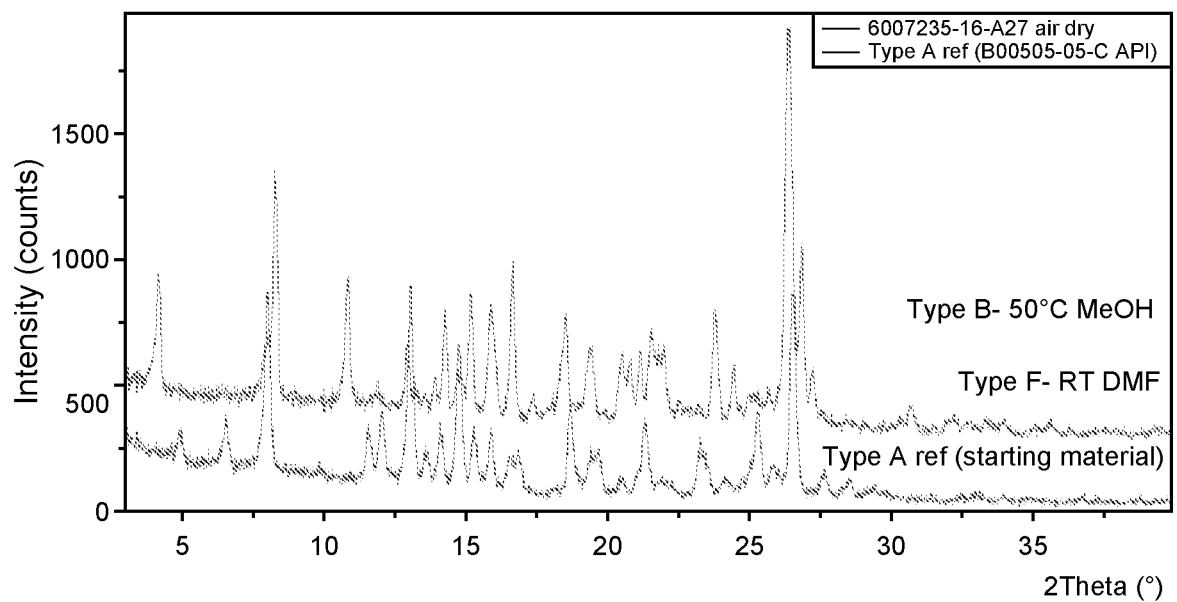
FIG. 19.
Figure 20:
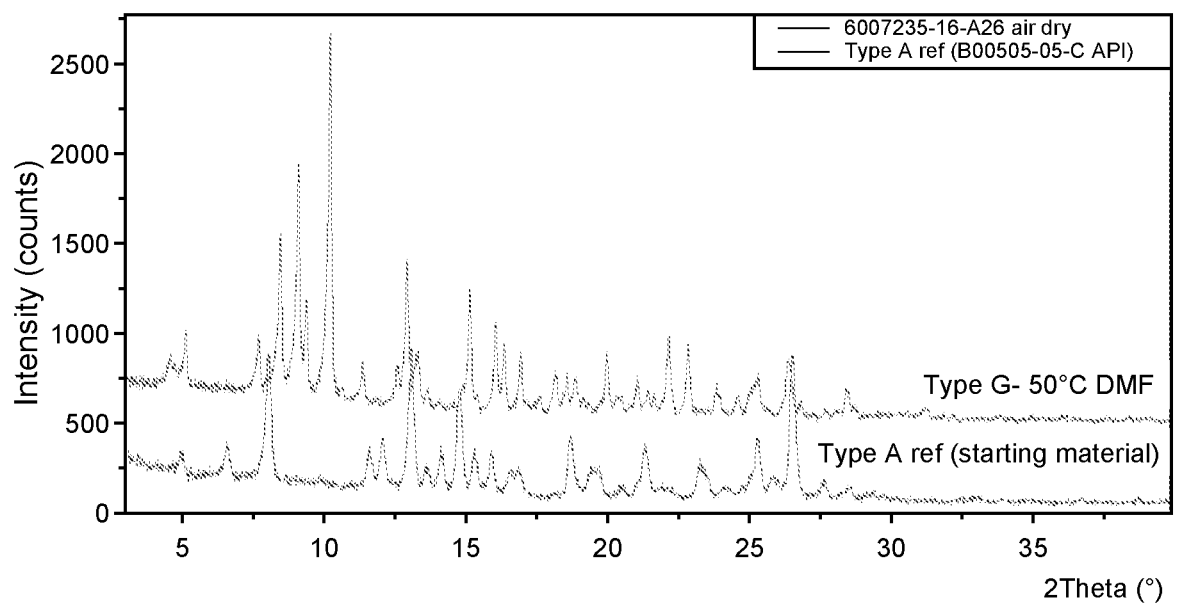
FIG. 20.

Slurries of HM30181 mesylate Type A in MeOH generated HM30181 mesylate Type B after 1 week at temperatures of 4° C. to 50° C. (see FIG. 15). Slurries of HM30181 mesylate Type A in DCM at ambient temperature and acetonitrile at 4° C. to 50° C. generated HM30181 mesylate Type C (see FIG. 16). Slurries of HM30181 mesylate Type A in NMP at ambient temperature generated HM30181 mesylate Type D (see FIG. 17). Both HM30181 mesylate Type C and HM30181 mesylate Type D showed significant similarities to HM30181 mesylate Type A. Slurries of HM30181 mesylate Type A in DMA at ambient conditions generated HM30181 mesylate Type E (see FIG. 18). Slurries of HM30181 mesylate Type A in DMF generated HM30181 mesylate Type F at ambient temperature (see FIG. 19) and Type G at 50° C. (see FIG. 20).

Table 3 (continued in Table 4)

| Exp | Method | Temp. | Solvent | API (mg) | Solvent (mL) | Crystal Type |
|---|---|---|---|---|---|---|
| 6007235-16-C10 | Slurry | 4° C. | 1,4-Dioxane | 25.9 | 0.2 | A |
| 6007235-16-B10 | Slurry | 50° C. | 1,4-Dioxane | 23.4 | 0.2 | A |
| 6007235-16-A10 | Slurry | ambient temperature | 1,4-Dioxane | 21 | 0.2 | A |
| 6007235-16-A34 | Slurry | ambient temperature | 1-Methyl-2-pyrrolidinone/water (1:1) | 25 | 0.2 | A |
| 6007235-16-C9 | Slurry | 4° C. | 2-Methyl tetrahydrofuran | 27.4 | 0.2 | A |
| 6007235-16-B9 | Slurry | 50° C. | 2-Methyl tetrahydrofuran | 24.5 | 0.2 | A |
| 6007235-16-A9 | Slurry | ambient temperature | 2-Methyl tetrahydrofuran | 28.7 | 0.2 | A |
| 6007235-16-C4 | Slurry | 4° C. | Acetone | 25.3 | 0.2 | A |
| 6007235-16-B4 | Slurry | 50° C. | Acetone | 27.9 | 0.2 | A |
| 6007235-16-A4 | Slurry | ambient temperature | Acetone | 26.7 | 0.2 | A |
| 6007235-16-C13 | Slurry | 4° C. | CHCl$_3$ | 22.4 | 0.2 | A |
| 6007235-16-B13 | Slurry | 50° C. | CHCl$_3$ | 29 | 0.1 | A |
| 6007235-16-A14 | Slurry | ambient temperature | CHCl$_3$ | 25.6 | 0.2 | A |
| 6007235-16-C21 | Slurry | 4° C. | Cumene | 22.1 | 0.2 | A |
| 6007235-16-B25 | Slurry | 50° C. | Cumene | 26.3 | 0.2 | A |
| 6007235-16-A26 | Slurry | ambient temperature | Cumene | 26.1 | 0.2 | A |
| 6007235-16-C17 | Slurry | 4° C. | Cyclohexane | 24.2 | 0.2 | A |
| 6007235-16-B17 | Slurry | 50° C. | Cyclohexane | 23.8 | 0.2 | A |
| 6007235-16-A18 | Slurry | ambient temperature | Cyclohexane | 26.2 | 0.2 | A |
| 6007235-16-C24 | Slurry | 4° C. | Cyclopentylmethyl ether | 20.8 | 0.2 | A |
| 6007235-16-B29 | Slurry | 50° C. | Cyclopentylmethyl ether | 24.9 | 0.2 | A |
| 6007235-16-A30 | Slurry | ambient temperature | Cyclopentylmethyl ether | 21.7 | 0.2 | A |
| 6007235-16-A22 | Slurry | ambient temperature | DMSO | 22.7 | 0.1 | A |
| 6007235-16-A31 | Slurry | ambient temperature | DMSO/water (1:1) | 25.1 | 0.2 | A |

| Exp | Method | Temp. | Solvent | API (mg) | Solvent (mL) | Crystal Type |
|---|---|---|---|---|---|---|
| 6007235-16-C2 | Slurry | 4° C. | Ethanol | 20.7 | 0.2 | A |
| 6007235-16-B2 | Slurry | 50° C. | Ethanol | 26.9 | 0.2 | A |
| 6007235-16-A2 | Slurry | ambient temperature | Ethanol | 21.7 | 0.2 | A |
| 6007235-16-C6 | Slurry | 4° C. | Ethyl acetate | 26.2 | 0.2 | A |
| 6007235-16-B6 | Slurry | 50° C. | Ethyl acetate | 25.5 | 0.2 | A |
| 6007235-16-A6 | Slurry | ambient temperature | Ethyl acetate | 24.2 | 0.2 | A |
| 6007235-16-C22 | Slurry | 4° C. | Ethyl formate | 24.8 | 0.2 | A |
| 6007235-16-B27 | Slurry | 50° C. | Ethyl formate | 25 | 0.2 | A |
| 6007235-16-A28 | Slurry | ambient temperature | Ethyl formate | 25.1 | 0.2 | A |
| 6007235-16-C23 | Slurry | 4° C. | Isobutyl Acetate | 23.7 | 0.2 | A |
| 6007235-16-B28 | Slurry | 50° C. | Isobutyl Acetate | 22 | 0.2 | A |
| 6007235-16-A29 | Slurry | ambient temperature | Isobutyl Acetate | 25.4 | 0.2 | A |
| 6007235-16-C3 | Slurry | 4° C. | isopropanol | 26.8 | 0.2 | A |
| 6007235-16-B3 | Slurry | 50° C. | isopropanol | 21.5 | 0.2 | A |
| 6007235-16-A3 | Slurry | ambient temperature | isopropanol | 23.6 | 0.2 | A |
| 6007235-16-C7 | Slurry | 4° C. | isopropyl acetate | 25.9 | 0.2 | A |
| 6007235-16-B7 | Slurry | 50° C. | isopropyl acetate | 21.9 | 0.2 | A |
| 6007235-16-A7 | Slurry | ambient temperature | isopropyl acetate | 28.8 | 0.2 | A |
| 6007235-16-C18 | Slurry | 4° C. | methyl ethyl ketone | 21.8 | 0.2 | A |
| 6007235-16-B18 | Slurry | 50° C. | methyl ethyl ketone | 20.6 | 0.2 | A |
| 6007235-16-A19 | Slurry | ambient temperature | methyl ethyl ketone | 27.1 | 0.2 | A |
| 6007235-16-C5 | Slurry | 4° C. | methyl isobutyl ketone | 26.1 | 0.2 | A |
| 6007235-16-B5 | Slurry | 50° C. | methyl isobutyl ketone | 27 | 0.2 | A |
| 6007235-16-A5 | Slurry | ambient temperature | methyl isobutyl ketone | 27.9 | 0.2 | A |

Table 4 (continued from Table 3)

| Exp | Method | Temp. | Solvent | API (mg) | Solvent (mL) | Crystal Type |
|---|---|---|---|---|---|---|
| 6007235-16-C11 | Slurry | 4° C. | Methyl t-butyl ether | 27.1 | 0.2 | A |
| 6007235-16-B11 | Slurry | 50° C. | Methyl t-butyl ether | 27.5 | 0.2 | A |
| 6007235-16-A11 | Slurry | ambient temperature | Methyl t-butyl ether | 26.8 | 0.2 | A |
| 6007235-16-A32 | Slurry | ambient temperature | N,N-Dimethylacetamide/water (1:1) | 26.9 | 0.2 | A |
| 6007235-16-A33 | Slurry | ambient temperature | N,N-Dimethylacetamide/water (1:1) | 27 | 0.2 | A |
| 6007235-16-C15 | Slurry | 4° C. | n-Heptane | 26.8 | 0.2 | A |
| 6007235-16-B15 | Slurry | 50° C. | n-Heptane | 22.7 | 0.2 | A |
| 6007235-16-A16 | Slurry | ambient temperature | n-Heptane | 22.8 | 0.2 | A |
| 6007235-16-C19 | Slurry | 4° C. | n-Propanol | 22.3 | 0.2 | A |
| 6007235-16-B23 | Slurry | 50° C. | n-Propanol | 21.8 | 0.2 | A |
| 6007235-16-A24 | Slurry | ambient temperature | n-Propanol | 23.3 | 0.2 | A |
| 6007235-16-C20 | Slurry | 4° C. | n-Propyl acetate | 21.5 | 0.2 | A |
| 6007235-16-B24 | Slurry | 50° C. | n-Propyl acetate | 27.4 | 0.2 | A |
| 6007235-16-A25 | Slurry | ambient temperature | n-Propyl acetate | 26.5 | 0.2 | A |
| 6007235-16-B19 | Slurry | 50° C. | t-Butanol | 23.7 | 0.2 | A |
| 6007235-16-A20 | Slurry | ambient temperature | t-Butanol | 23.9 | 0.2 | A |
| 6007235-16-C8 | Slurry | 4° C. | Tetrahydrofuran | 22.9 | 0.2 | A |
| 6007235-16-B8 | Slurry | 50° C. | Tetrahydrofuran | 21.7 | 0.2 | A |
| 6007235-16-A8 | Slurry | ambient temperature | Tetrahydrofuran | 20.9 | 0.2 | A |
| 6007235-16-C14 | Slurry | 4° C. | Toluene | 24.2 | 0.2 | A |
| 6007235-16-B14 | Slurry | 50° C. | Toluene | 25.7 | 0.2 | A |
| 6007235-16-A15 | Slurry | ambient temperature | Toluene | 24.9 | 0.2 | A |
| 6007235-16-C16 | Slurry | 4° C. | Water | 27.6 | 0.2 | A |
| 6007235-16-B16 | Slurry | 50° C. | Water | 27 | 0.2 | A |

-continued

| | | | | | | |
|---|---|---|---|---|---|---|
| 6007235-16-C28 | Slurry | 4° C. | 1-Methyl-2-pyrrolidinonee/water (1:1) | 23.9 | 0.2 | amorphous + A |
| 6007235-16-C26 | Slurry | 4° C. | N,N-Dimethylacetamide/water (1:1) | 26.4 | 0.2 | amorphous + A |
| 6007235-16-C27 | Slurry | 4° C. | N,N-Dimethylacetamide/water (1:1) | 24 | 0.2 | amorphous + A |
| 6007235-16-A17 | Slurry | ambient temperature | Water | 22 | 0.2 | amorphous + A |
| 6007235-16-B20 | Slurry | 50° C. | 1 -mMethyl-2-pyrrolidinone | 23.7 | 0.1 | amorphous |
| 6007235-16-B21 | Slurry | 50° C. | DMSO | 23.8 | 0.1 | amorphous |
| 6007235-16-C25 | Slurry | 4° C. | DMSO/water (1:1) | 24.3 | 0.2 | amorphous |
| 6007235-16-A1 | Slurry | ambient temperature | Methanol | 24.9 | 0.2 | B |
| 6007235-16-B1 | Slurry | 50° C. | Methanol | 27 | 0.1 | B |
| 6007235-16-C1 | Slurry | 4° C. | Methanol | 23.2 | 0.2 | B |
| 6007235-16-A12 | Slurry | ambient temperature | Acetonitrile | 25.5 | 0.2 | C |
| 6007235-16-A13 | Slurry | ambient temperature | Dichloromethane | 21.9 | 0.2 | C |
| 6007235-16-B12 | Slurry | 50° C. | Acetonitrile | 22.7 | 0.1 | C |
| 6007235-16-C12 | Slurry | 4° C. | Acetonitrile | 21.9 | 0.2 | C |
| 6007235-16-A21 | Slurry | ambient temperature | 1-Methyl-2-pyrrolidinone | 24.6 | 0.2 | D |
| 6007235-16-A23 | Slurry | ambient temperature | N,N-Dimethylacetamide | 25.6 | 0.1 | E |
| 6007235-16-A27 | Slurry | ambient temperature | N,N-Dimethylacetamide | 26.2 | 0.1 | F |
| 6007235-16-B26 | Slurry | 50° C. | N,N-Dimethylacetamide | 27.3 | 0.1 | G |

Figure 21:
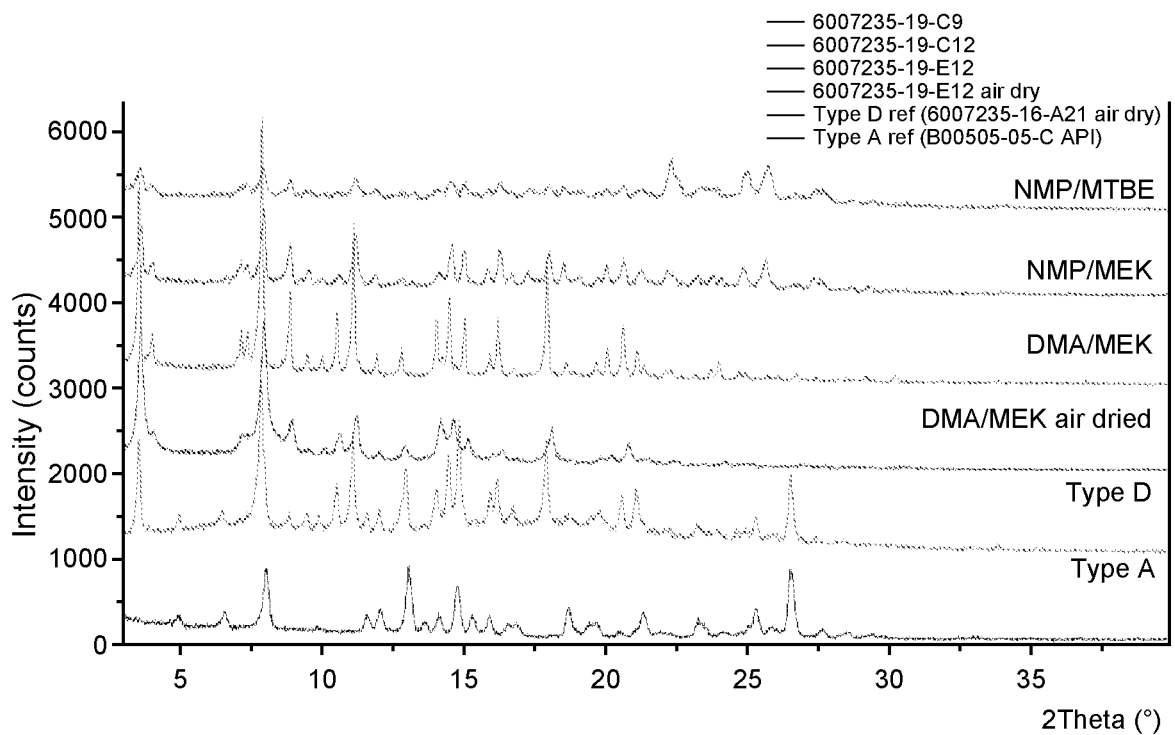
FIG. 21.
Figure 22:
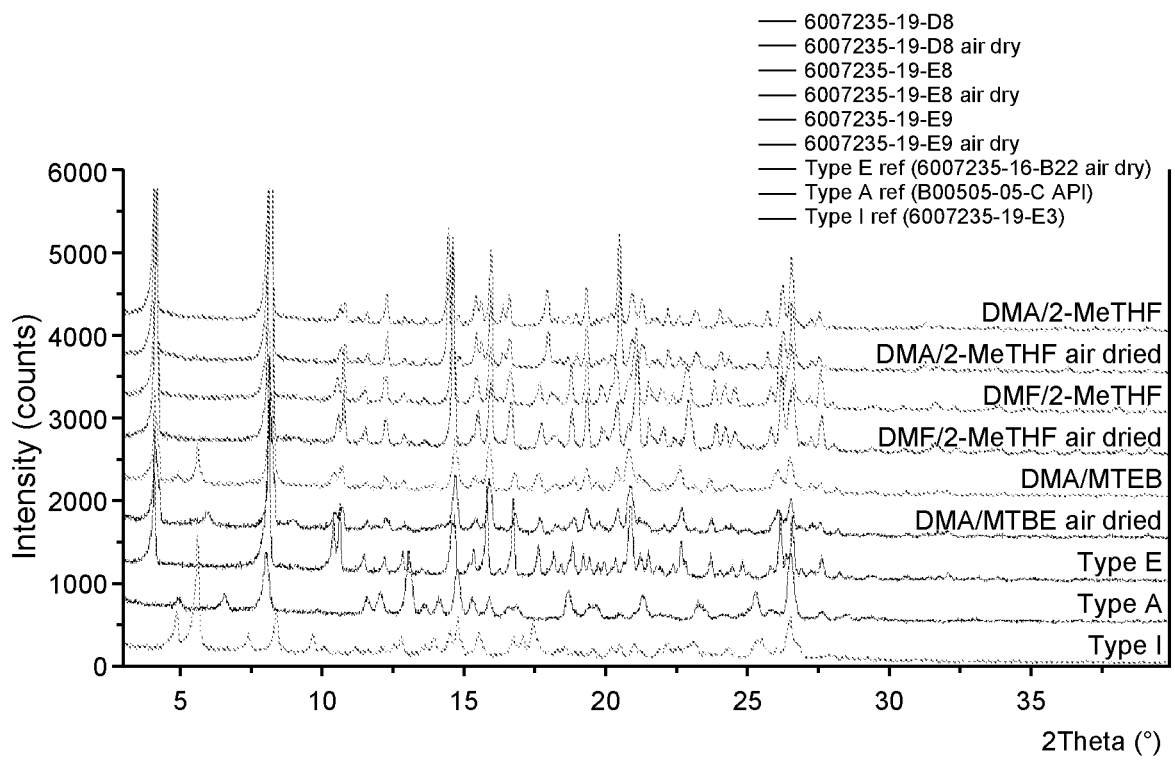
FIG. 22.
Figure 23:
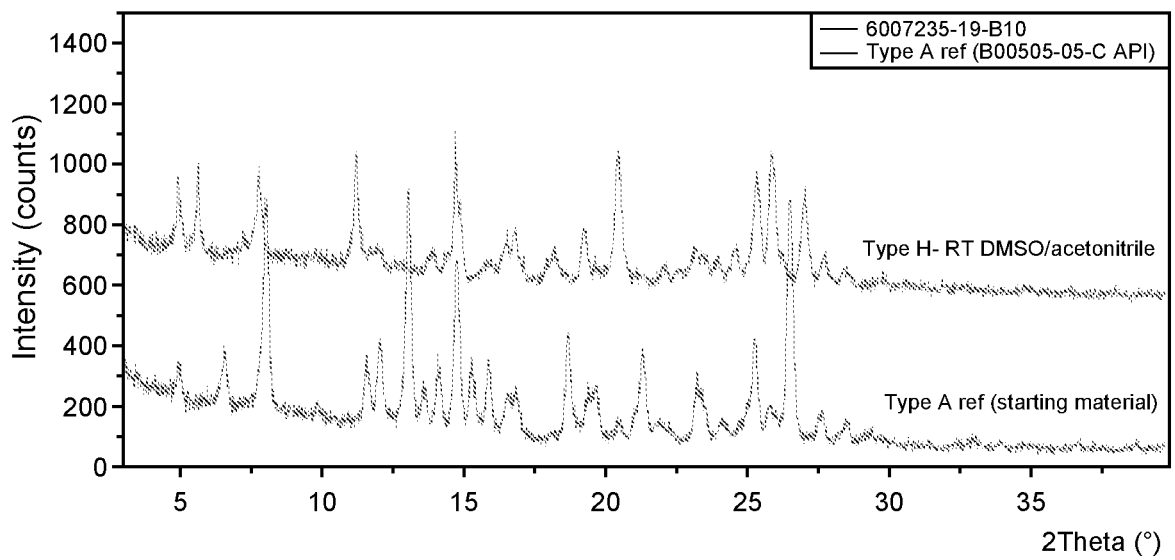
FIG. 23.
Figure 24:
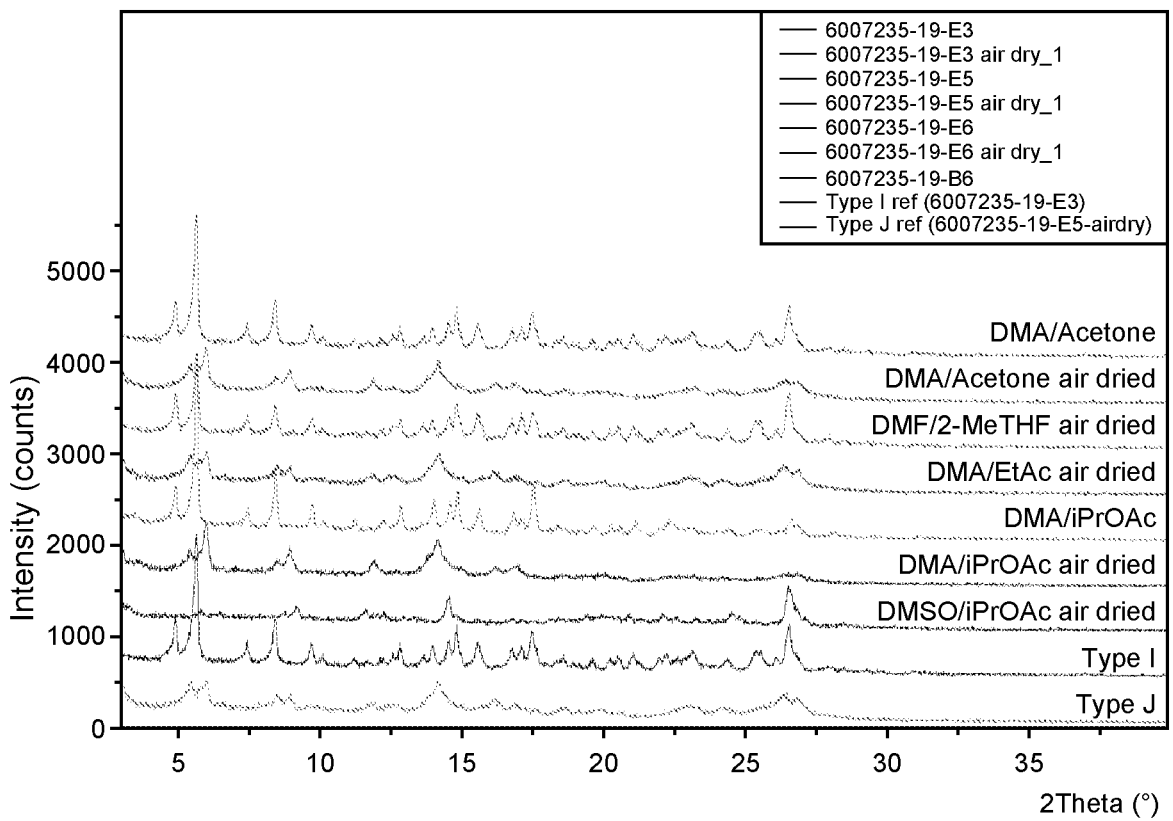
FIG. 24.

Generation and/or screening of HM30181 mesylate polymorphs was also performed by preparing HM30181 mesylate Type A starting material for liquid and solid vapor diffusion as described below. Resulting solids were analyzed by XRPD and identified for physical state. Results are summarized in Table 5, Table 6, and Table 7. Liquid vapor diffusion of MTBE into NMP solution yielded HM30181 mesylate Type D (see FIG. 21). Liquid vapor diffusion of MEK into NMP or DMA solution yielded HM30181 mesylate Type D (see FIG. 21). Some loss of crystallinity was noted on air-dried HM30181 mesylate Type D, suggesting possible solvate. Liquid vapor diffusion of 2-MeTHF into DMA or DMF solution yielded HM30181 mesylate Type E (see FIG. 22). Liquid vapor diffusion of MTBE into DMA solution yielded HM30181 mesylate Type E, with a few additional diffraction peaks, which Inventors believe are attributable to HM30181 mesylate Type I (FIGS. 4 to 8). Liquid vapor diffusion of ACN into DMSO solution yielded HM30181 mesylate Type H (see FIG. 23). Liquid vapor diffusion of Acetone, Ethyl Acetate, or isopropyl acetate into DMA solution yielded HM30181 mesylate Type I (see FIG. 24). Air-drying of HM30181 mesylate Type I yielded HM30181 mesylate Type J (see FIG. 24). Liquid vapor diffusion of isopropyl acetate into DMSO solution followed by air drying also yielded HM30181 mesylate Type J.

TABLE 5

| Exp | Temperature | Solvent | API (mg) | Solvent (mL) | Crystal Type |
|---|---|---|---|---|---|
| 6007235-17-A1 | ambient temperature | methanol | 25.2 | 0.1 | A |
| 6007235-17-A2 | ambient temperature | ethanol | 22.1 | 0.1 | A |
| 6007235-17-A3 | ambient temperature | isopropanol | 21.4 | 0.1 | A |
| 6007235-17-A4 | ambient temperature | acetone | 24.8 | 0.1 | A |
| 6007235-17-A5 | ambient temperature | methyl isobutyl ketone | 25.8 | 0.1 | A |
| 6007235-17-A6 | ambient temperature | ethyl acetate | 22.9 | 0.1 | A |
| 6007235-17-A7 | ambient temperature | isopropyl acetate | 23.8 | 0.1 | A |
| 6007235-17-A8 | ambient temperature | tetrahydrofuran | 24.5 | 0.1 | A |
| 6007235-17-A9 | ambient temperature | 2-methyl tetrahydrofuran | 24.9 | 0.1 | A |
| 6007235-17-A10 | ambient temperature | methyl t-butyl ether | 27.1 | 0.1 | A |
| 6007235-17-A11 | ambient temperature | acetonitrile | 27.7 | 0.1 | A |
| 6007235-17-A12 | ambient temperature | dichloromethane | 24.9 | 0.1 | A |

TABLE 5-continued

| Exp | Temperature | Solvent | API (mg) | Solvent (mL) | Crystal Type |
|---|---|---|---|---|---|
| 6007235-17-A13 | ambient temperature | CHCl$_3$ | 29 | 0.1 | A |
| 6007235-17-A14 | ambient temperature | methyl ethyl ketone | 23.4 | 0.1 | A |
| 6007235-17-A15 | ambient temperature | t-butanol | 28.2 | 0.1 | A |
| 6007235-17-A16 | ambient temperature | n-propanol | 25.4 | 0.1 | A |
| 6007235-17-A17 | ambient temperature | ethyl formate | 27.3 | 0.1 | A |
| 6007235-17-A18 | ambient temperature | cyclopentylmethyl ether | 25.1 | 0.1 | A |
| 6007235-17-A19 | 25° C. | 25° C./60% RH | 22.9 | 0.1 | A |
| 6007235-17-A20 | 40° C. | 40° C./75% RH | 23.5 | 0.1 | A |
| 6007235-17-A21 | 40° C. | 100% RH(water) | 22.7 | 0.1 | A |

Table 6 (continued on Table 7)

| Exp | Temp. | Solvent | API (mg) | Solvent (mL) | Anti-solvent | Anti-solvent (mL) | Crystal Type |
|---|---|---|---|---|---|---|---|
| 6007235-19-A1 | ambient temperature | methanol | 22 | 16 | ethyl formate | 0.5 | No solids |
| 6007235-19-A2 | ambient temperature | methanol | 23 | 16 | dichloromethane | 0.5 | No solids |
| 6007235-19-B1 | ambient temperature | DMSO | 25 | 0.3 | ethanol | 2 | No solids |
| 6007235-19-B2 | ambient temperature | DMSO | 25 | 0.3 | isopropanol | 2 | No solids |
| 6007235-19-B3 | ambient temperature | DMSO | 25 | 0.3 | acetone | 2 | Amorphous |
| 6007235-19-B4 | ambient temperature | DMSO | 25 | 0.3 | MIBK | 2 | Amorphous |
| 6007235-19-B5 | ambient temperature | DMSO | 25 | 0.3 | ethyl acetate | 2 | Amorphous |
| 6007235-19-B7 | ambient temperature | DMSO | 25 | 0.3 | tetrahydrofuran | 2 | Amorphous |
| 6007235-19-B8 | ambient temperature | DMSO | 25 | 0.3 | 2-MeTHF | 2 | Amorphous |
| 6007235-19-B9 | ambient temperature | DMSO | 25 | 0.3 | methyl t-butyl ether | 2 | Amorphous |
| 6007235-19-B11 | ambient temperature | DMSO | 25 | 0.3 | dichloromethane | 2 | Amorphous and A |
| 6007235-19-B12 | ambient temperature | DMSO | 25 | 0.3 | methyl ethyl ketone | 2 | Amorphous |
| 6007235-19-B13 | ambient temperature | DMSO | 25 | 0.3 | t-butanol | 2 | No solids |
| 6007235-19-C1 | ambient temperature | NMP | 30 | 3 | ethanol | 3 | No solids |
| 6007235-19-C2 | ambient temperature | NMP | 30 | 3 | isopropanol | 3 | No solids |
| 6007235-19-C3 | ambient temperature | NMP | 30 | 3 | acetone | 3 | No solids |
| 6007235-19-C4 | ambient temperature | NMP | 30 | 3 | MIBK | 3 | No solids |
| 6007235-19-C5 | ambient temperature | NMP | 30 | 3 | ethyl acetate | 3 | Amorphous and A |
| 6007235-19-C6 | ambient temperature | NMP | 30 | 3 | isopropyl acetate | 3 | No solids |
| 6007235-19-C7 | ambient temperature | NMP | 30 | 3 | tetrahydrofuran | 3 | No solids |
| 6007235-19-C8 | ambient temperature | NMP | 30 | 3 | 2-MeTHF | 3 | No solids |
| 6007235-19-C10 | ambient temperature | NMP | 30 | 3 | acetonitrile | 3 | No solids |
| 6007235-19-C11 | ambient temperature | NMP | 30 | 3 | dichloromethane | 3 | No solids |
| 6007235-19-C13 | ambient temperature | NMP | 30 | 3 | t-butanol | 3 | No solids |
| 6007235-19-D1 | ambient temperature | DMF | 30 | 3 | ethanol | 3 | No solids |

| | | API | | Anti-solvent | | |
|---|---|---|---|---|---|---|
| Exp. | Temp. | (mg) Solvent | Solvent (mL) | Anti-solvent | (mL) | XRPD (wet cake) XRPD (air-dry) |

| Exp. | Temp. | API (mg) | Solvent | Solvent (mL) | Anti-solvent | Anti-solvent (mL) | XRPD (wet cake) | XRPD (air-dry) |
|---|---|---|---|---|---|---|---|---|
| 6007235-19-D2 | ambient temperature | 30 | DMF | 3 | isopropanol | 3 | | Amorphous |
| 6007235-19-D4 | ambient temperature | 30 | DMF | 3 | MIBK | 3 | | No solids |
| 6007235-19-D5 | ambient temperature | 30 | DMF | 3 | ethyl acetate | 3 | | Amorphous |
| 6007235-19-D6 | ambient temperature | 30 | DMF | 3 | isopropyl acetate | 3 | | Amorphous |
| 6007235-19-D7 | ambient temperature | 30 | DMF | 3 | tetrahydrofuran | 3 | | No solids |
| 6007235-19-D9 | ambient temperature | 30 | DMF | 3 | methyl t-butyl ether | 3 | | Amorphous |
| 6007235-19-D10 | ambient temperature | 30 | DMF | 3 | acetonitrile | 3 | | No solids |
| 6007235-19-D11 | ambient temperature | 30 | DMF | 3 | dichloromethane | 3 | | No solids |
| 6007235-19-D12 | ambient temperature | 30 | DMF | 3 | methyl ethyl ketone | 3 | | Amorphous |
| 6007235-19-D13 | ambient temperature | 30 | DMF | 3 | t-butanol | 3 | | No solids |
| 6007235-19-E1 | ambient temperature | 20 | DMA | 4 | ethanol | 8 | | No solids |
| 6007235-19-E2 | ambient temperature | 20 | DMA | 4 | isopropanol | 8 | | No solids |
| 6007235-19-E4 | ambient temperature | 20 | DMA | 4 | MIBK | 8 | | No solids |
| 6007235-19-E7 | ambient temperature | 20 | DMA | 4 | tetrahydrofuran | 8 | | No solids |
| 6007235-19-E10 | ambient temperature | 20 | DMA | 4 | acetonitrile | 8 | | No solids |
| 6007235-19-E11 | ambient temperature | 20 | DMA | 4 | dichloromethane | 8 | | No solids |
| 6007235-19-E13 | ambient temperature | 20 | DMA | 4 | t-butanol | 8 | | No solids |

Table 7 (continued from Table 6)

| Exp. | Temp. | API (mg) | Solvent | Solvent (mL) | Anti-solvent | Anti-solvent (mL) | XRPD (wet cake) | XRPD (air-dry) |
|---|---|---|---|---|---|---|---|---|
| 6007235-19-C12 | ambient temperature | 30 | NMP | 3 | MEK | 3 | Type D | — |
| 6007235-19-E12 | ambient temperature | 20 | DMA | 4 | MEK | 8 | Type D | Type D and amorphous |
| 6007235-19-C9 | ambient temperature | 30 | NMP | 3 | MTBE | 3 | Type D | — |
| 6007235-19-D8 | ambient temperature | 30 | DMF | 3 | 2-MeTHF | 3 | Type E | E |
| 6007235-19-E8 | ambient temperature | 20 | DMA | 4 | 2-MeTHF | 8 | Type E | E |
| 6007235-19-E9 | ambient temperature | 20 | DMA | 4 | MTBE | 8 | Type E and I | E |
| 6007235-19-B10 | ambient temperature | 25 | DMSO | 0.3 | ACN | 2 | Type H | — |
| 6007235-19-E3 | ambient temperature | 20 | DMA | 4 | Acetone | 8 | Type I | Type J |
| 6007235-19-E5 | ambient temperature | 20 | DMA | 4 | EtOAc | 8 | Type I | Type J |
| 6007235-19-E6 | ambient temperature | 20 | DMA | 4 | iPrOAc | 8 | Type I | Type J |
| 6007235-19-B6 | ambient temperature | 25 | DMSO | 0.3 | iPrOAc | 3 | — | Type J |

Figure 25:
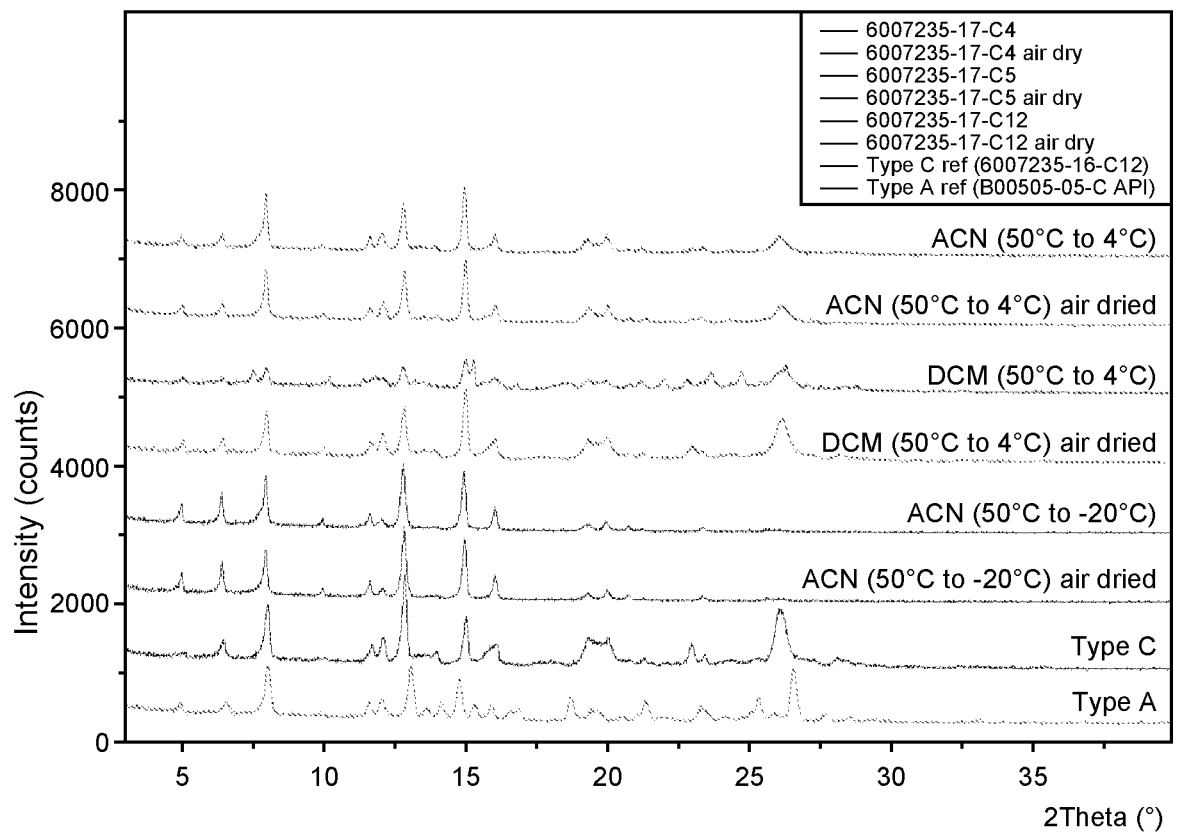
FIG. 25.

Generation and/or screening of HM30181 mesylate polymorphs by cooling was carried out by treating HM30181 mesylate Type A starting material using gradual or rapid (i.e. crash) cooling as described below. The resulting solids were analyzed by XRPD and identified for physical state. Results are summarized in Table 8. Cooling experiments in acetonitrile and DCM yielded HM30181 mesylate Type C; no significant change was noted on air-drying (see FIG. 25).

TABLE 8

| Exp. | Temp. | Temp | Solvent/Anti-solvent | API (mg) | Solvent/Anti-solvent (mL) | XRPD (wet cake) | XRPD (air-dry) |
|---|---|---|---|---|---|---|---|
| 6007235-17-C6 | Slow Cooling | 50° C.-->4° C. | NMP | 20.9 | 4 | No solids | |
| 6007235-17-C14 | Crash Cooling | 50° C.-->-20° C. | NMP | 26.2 | 4 | Amorphous | |
| 6007235-17-C2 | Slow Cooling | 50° C.-->4° C. | CHCl$_3$ | 25.4 | 4 | Amorphous and A | |
| 6007235-17-C10 | Crash Cooling | 50° C.-->-20° C. | CHCl$_3$ | 25.4 | 4 | No solids | |
| 6007235-17-C13 | Crash Cooling | 50° C.-->-20° C. | DCM | 22.1 | 10 | No solids | |
| 6007235-17-C3 | Slow Cooling | 50° C.-->4° C. | EtOH | 5 | 20 | No solids | |
| 6007235-17-C11 | Crash Cooling | 50° C.-->-20° C. | EtOH | 5 | 20 | No solids | |
| 6007235-17-C9 | Crash Cooling | 50° C.-->-20° C. | MeOH | 22.9 | 10 | No solids | |
| 6007235-17-C1 | Slow Cooling | 50° C.-->4° C. | MeOH | 24.7 | 20 | No solids | |
| 6007235-17-C7 | Slow Cooling | 50° C.-->4° C. | DMA | 25 | 4 | Amorphous and A | |
| 6007235-17-C15 | Crash Cooling | 50° C.-->-20° C. | DMA | 26.9 | 4 | Amorphous | |
| 6007235-17-C8 | Slow Cooling | 50° C.-->4° C. | DMF | 25.1 | 4 | No solids | |
| 6007235-17-C16 | Crash Cooling | 50° C.-->-20° C. | DMF | 25.1 | 4 | Amorphous | |
| 6007235-17-C4 | Slow Cooling | 50° C.-->4° C. | ACN | 12.6 | 10 | Type C | Type C |
| 6007235-17-C5 | Slow Cooling | 50° C.-->4° C. | DCM | 26.8 | 10 | Type C + peaks | Type C |
| 6007235-17-C12 | Crash cooling | 50° C.-->-20° C. | ACN | 12.6 | 10 | Type C | Type C |

HM30181 mesylate was also subjected to evaporation methods by treating HM30181 mesylate Type A starting material as described below. The resulting solids were analyzed by XRPD and identified for physical state. Results are shown in Table 9.

TABLE 9

| Exp | Temp. | Solvent | API (mg) | Solvent (mL) | Crystal Type |
|---|---|---|---|---|---|
| 6007235-17-B6 | ambient temperature | methanol | 12 | 10 | Amorphous |
| 6007235-17-B1 | ambient temperature | methanol | 12 | 10 | Amorphous |
| 6007235-17-B8 | 50° C. | ethanol | 5 | 20 | Amorphous and A |
| 6007235-17-B3 | 50° C. | ethanol | 5 | 20 | Amorphous |
| 6007235-17-B5 | 50° C. | dichloromethane | 21.2 | 20 | Amorphous |
| 6007235-17-B10 | 50° C. | dichloromethane | 28 | 20 | Amorphous |
| 6007235-17-B7 | ambient temperature | CHCl$_3$ | 27.4 | 7 | Amorphous |
| 6007235-17-B2 | ambient temperature | CHCl$_3$ | 26 | 7 | Amorphous |
| 6007235-17-B9 | 50° C. | acetonitrile | 10.5 | 40 | Amorphous |
| 6007235-17-B4 | 50° C. | acetonitrile | 10.5 | 40 | Amorphous |

Figure 26:
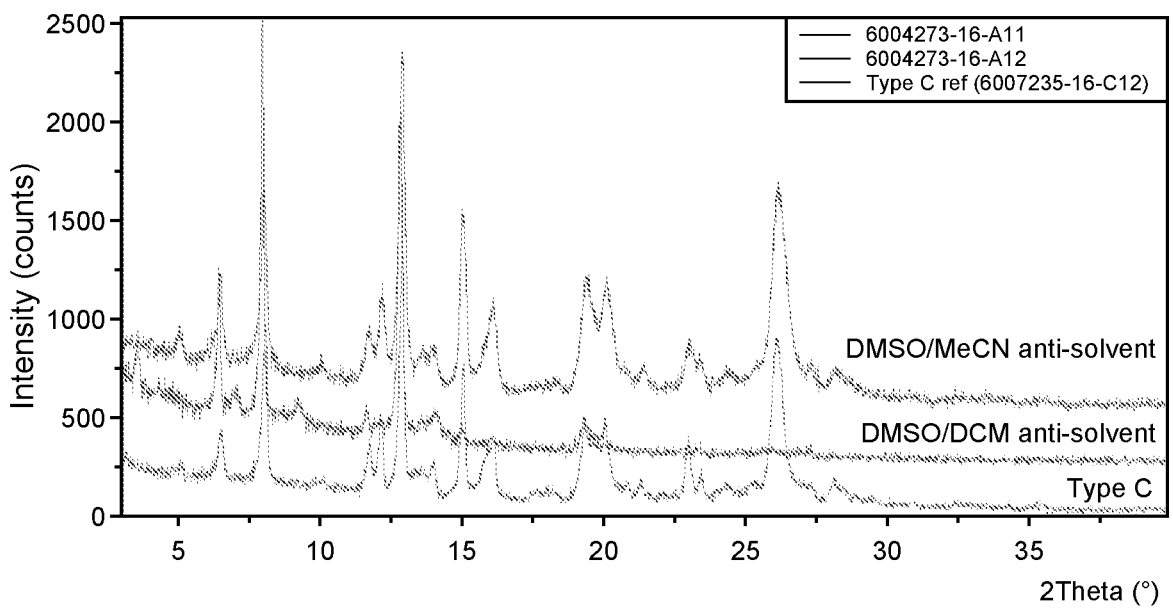
FIG. 26.
Figure 27:
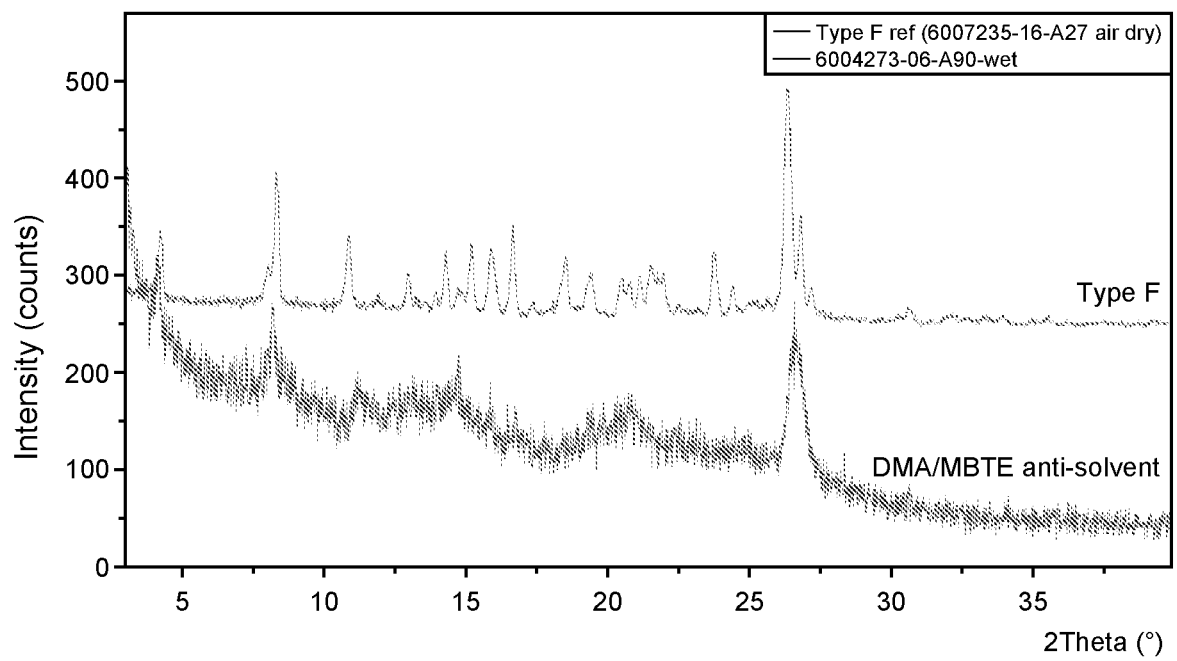
FIG. 27.
Figure 28:
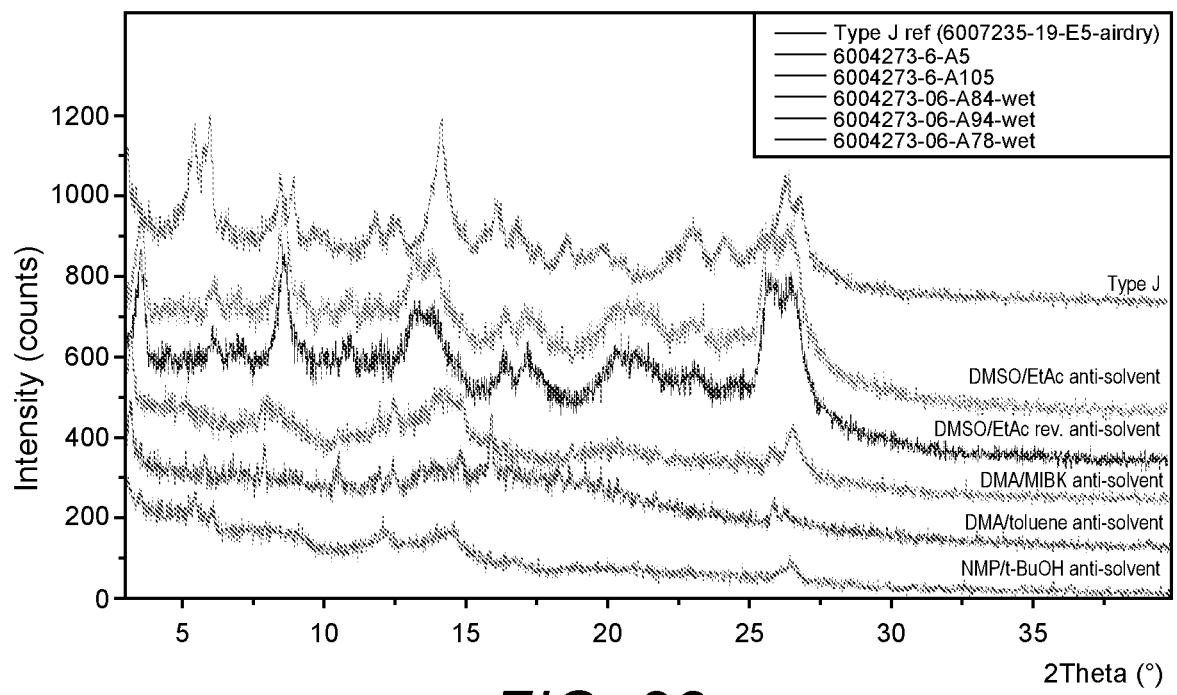
FIG. 28.
Figure 29:
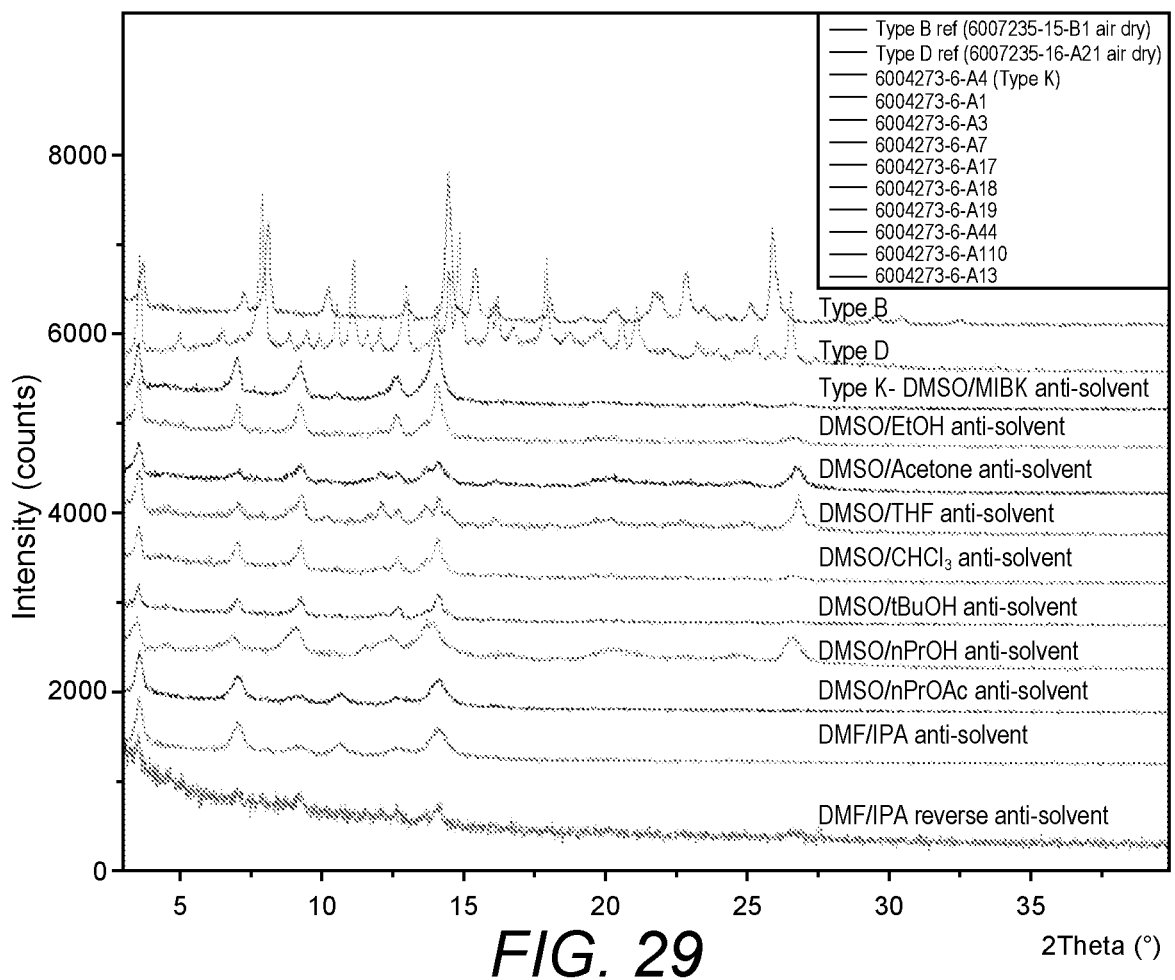
FIG. 29.
Figure 30:
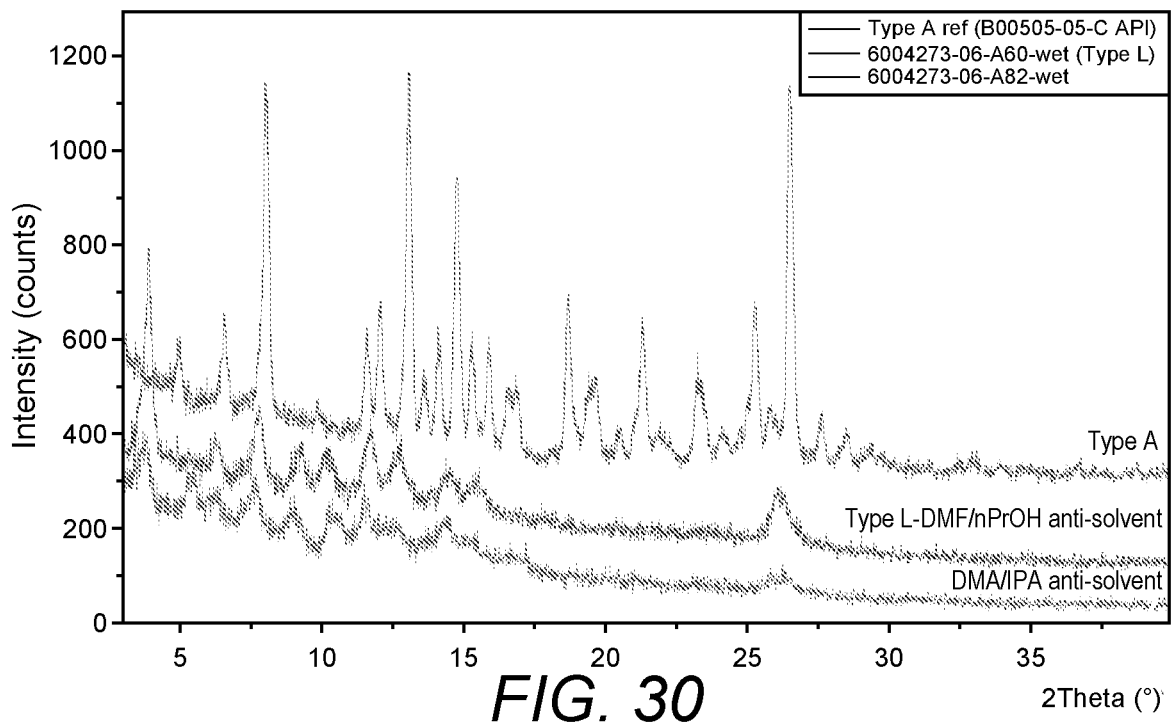
FIG. 30.
Figure 31:
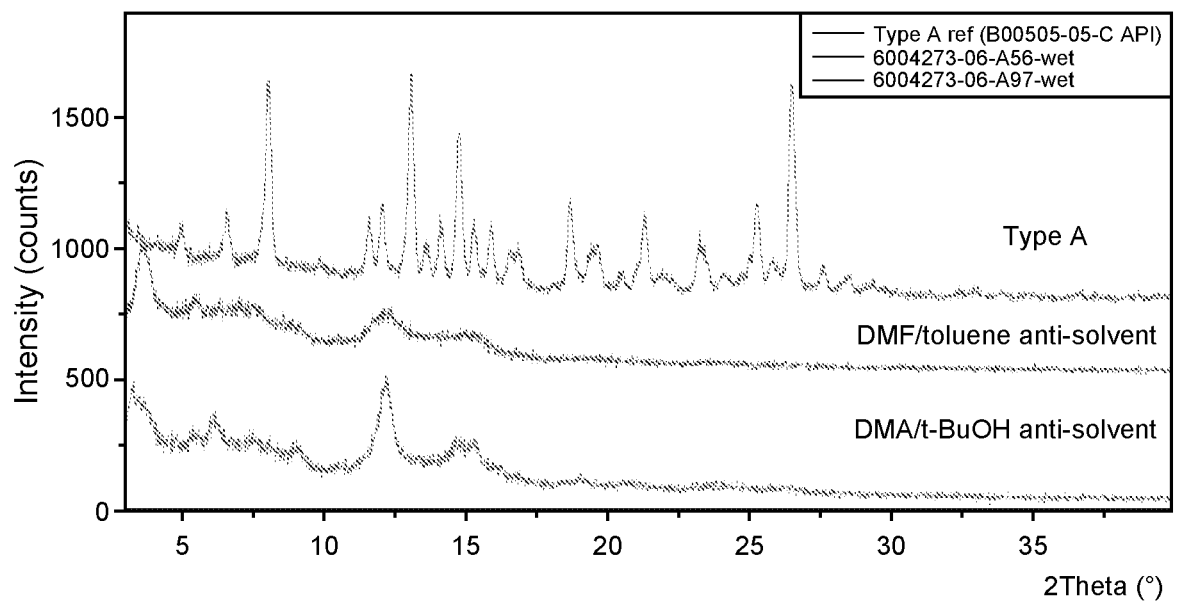
FIG. 31.

Generation and/or screening of HM30181 mesylate polymorphs by treatment with anti-solvents was performed by treating HM30181 mesylate Type A starting material as described below. The resulting solids were analyzed by XRPD and identified for physical state. Results are summarized in Table 10, Table 11, Table 12, and Table 13. Anti-solvent studies in DMSO yielded HM30181 mesylate Type C (see FIG. 26). Anti-solvent studies in N,N-dimethylacetamide with methyl t-butyl ether yielded a HM30181 mesylate Type F polymorphism (see FIG. 27). Anti-solvent addition and reverse anti-solvent addition in DMSO/EtOAc, DMA/MIBK, DMA/toluene and NMP/t-BuOH yielded primarily amorphous content and a polymorphism with some similarity to HM30181 mesylate Type J (see FIG. 28). Other anti-solvent studies in DMSO and DMF yielded a HM30181 mesylate Type K polymorphism (or possibly a mixture of types, see FIG. 29). Anti-solvent experiments in DMF/n-propanol and DMA/isopropanol yielded a HM30181 mesylate Type L polymorphism (see FIG. 30). Anti-solvent addition DMF/Toluene and DMA/t-BuOH were mostly amorphous, but also generated HM30181 mesylate Type M (see FIG. 31).

Table 10 (continued on Table 11)

| NB | Solvent | Anti-solvent | Anti-solvent (mL) | Precipitation? | Evap solids? | Identification |
|---|---|---|---|---|---|---|
| 6004273-06-A1 | DMSO | EtOH | 20 | N | Y | Type K |
| 6004273-06-A2 | DMSO | IPA | 10 | Y | | insufficient solids/gel |
| 6004273-06-A3 | DMSO | Acetone | 10 | Y | | Type K |
| 6004273-06-A4 | DMSO | MIBK | 10 | Y | | Type K |

| NB | Solvent | Anti-solvent | Anti-solvent (mL) | Precipitation? | Evap solids? | Identification |
|---|---|---|---|---|---|---|
| 6004273-06-A5 | DMSO | EtOAc | 10 | Y | | insufficient solids/gel |
| 6004273-06-A6 | DMSO | iPrOAc | 10 | Y | | insufficient solids/gel |
| 6004273-06-A7 | DMSO | THF | 10 | Y | | Similar to Type K |
| 6004273-06-A8 | DMSO | 2-MeTHF | 10 | Y | | Amorphous |
| 6004273-06-A9 | DMSO | 1,4-Dioxane | 20 | Y | | insufficient solids/gel |
| 6004273-06-A10 | DMSO | MTBE | 20 | Y | | Amorphous |
| 6004273-06-A11 | DMSO | ACN | 20 | N | Y | Type C |
| 6004273-06-A12 | DMSO | DCM | 20 | N | Y | Similar to Type C |
| 6004273-06-A13 | DMSO | CHCl$_3$ | 20 | N | Y | Type K |
| 6004273-06-A14 | DMSO | Toluene | 10 | Y | | Amorphous |
| 6004273-06-A15 | DMSO | Water | 20 | N | N | insufficient solids/gel |
| 6004273-06-A16 | DMSO | MEK | 10 | Y | | insufficient solids/gel |
| 6004273-06-A17 | DMSO | t-Butanol | 10 | Y | | Type K |
| 6004273-06-A18 | DMSO | n-Propanol | 10 | Y | | Type K |
| 6004273-06-A19 | DMSO | n-Propyl acetate | 10 | Y | | Type K |
| 6004273-06-A20 | CHCl$_3$ | Ethanol | 10 | Y | | Type A |
| 6004273-06-A21 | CHCl$_3$ | IPA | 10 | Y | | Type A |
| 6004273-06-A22 | CHCl$_3$ | Acetone | 10 | Y | | Type A |
| 6004273-06-A23 | CHCl$_3$ | MIBK | 10 | Y | | Type A |
| 6004273-06-A24 | CHCl$_3$ | EtOAc | 10 | Y | | Type A |
| 6004273-06-A25 | CHCl$_3$ | iPrOAc | 10 | Y | | Type A |
| 6004273-06-A26 | CHCl$_3$ | THF | 10 | Y | | Type A |
| 6004273-06-A27 | CHCl$_3$ | 2-MeTHF | 10 | Y | | Type A |
| 6004273-06-A28 | CHCl$_3$ | 1,4-Dioxane | 10 | Y | | insufficient solids/gel |
| 6004273-06-A29 | CHCl$_3$ | MTBE | 10 | Y | | Type A |
| 6004273-06-A30 | CHCl$_3$ | ACN | 10 | Y | | Type A |
| 6004273-06-A31 | CHCl$_3$ | DCM | 10 | Y | | Type A |
| 6004273-06-A32 | CHCl$_3$ | Toluene | 10 | Y | | Type A |
| 6004273-06-A33 | CHCl$_3$ | n-Heptane | 10 | Y | | Type A |

Table 11 (continued from Table 10 and on Table 12)

| NB | Solvent | Anti-solvent | Anti-solvent (mL) | Precipitation? | Evap solids? | Identification |
|---|---|---|---|---|---|---|
| 6004273-06-A34 | CHCl$_3$ | MeOAc | 10 | Y | | Type A |
| 6004273-06-A35 | CHCl$_3$ | Cyclohexane | 10 | Y | | Type A |
| 6004273-06-A36 | CHCl$_3$ | MEK | 10 | Y | | Type A |
| 6004273-06-A37 | CHCl$_3$ | t-Butanol | 10 | Y | | Type A |
| 6004273-06-A38 | CHCl$_3$ | n-Propanol | 10 | Y | | Type A |
| 6004273-06-A39 | CHCl$_3$ | n-Propyl acetate | 10 | Y | | Type A |
| 6004273-06-A40 | CHCl$_3$ | Ethyl formate | 10 | Y | | Type A |
| 6004273-06-A41 | CHCl$_3$ | iBuOAc | 10 | Y | | Type A |
| 6004273-06-A42 | CHCl$_3$ | CPME | 10 | Y | | Type A |
| 6004273-06-A43 | DMF | EtOH | 20 | N | Y | Amorphous |
| 6004273-06-A44 | DMF | IPA | 10 | Y | | Type K |
| 6004273-06-A45 | DMF | Acetone | 20 | N | Y | insufficient solids/gel |
| 6004273-06-A46 | DMF | MIBK | 10 | Y | | Amorphous |
| 6004273-06-A47 | DMF | EtOAc | 10 | Y | | Type A |
| 6004273-06-A48 | DMF | iPrOAc | 10 | Y | | insufficient solids/gel |
| 6004273-06-A49 | DMF | THF | 20 | N | Y | insufficient solids/gel |
| 6004273-06-A50 | DMF | 2-MeTHF | 10 | Y | | insufficient solids/gel |
| 6004273-06-A51 | DMF | 1,4-Dioxane | 20 | N | Y | insufficient solids/gel |
| 6004273-06-A52 | DMF | MTBE | 10 | Y | | Type A |
| 6004273-06-A53 | DMF | ACN | 20 | N | Y | insufficient solids/gel |
| 6004273-06-A54 | DMF | DCM | 20 | N | Y | insufficient solids/gel |
| 6004273-06-A55 | DMF | CHCl$_3$ | 20 | N | Y | insufficient solids/gel |
| 6004273-06-A56 | DMF | Toluene | 10 | Y | | Type M |
| 6004273-06-A57 | DMF | Water | 20 | N | Y | insufficient solids/gel |

-continued

| NB | Solvent | Anti-solvent | Anti-solvent (mL) | Precipitation? | Evap solids? | Identification |
|---|---|---|---|---|---|---|
| 6004273-06-A58 | DMF | MEK | 20 | N | Y | insufficient solids/gel |
| 6004273-06-A59 | DMF | t-Butanol | 10 | Y |  | insufficient solids/gel |
| 6004273-06-A60 | DMF | n-Propanol | 20 | N | Y | Type L + amorphous |
| 6004273-06-A61 | DMF | n-Propyl acetate | 10 | Y |  | Type A |
| 6004273-06-A62 | NMP | EtOH | 20 | N | N | insufficient solids/gel |
| 6004273-06-A63 | NMP | IPA | 10 | Y |  | insufficient solids/gel |
| 6004273-06-A64 | NMP | Acetone | 20 | N | N | insufficient solids/gel |
| 6004273-06-A65 | NMP | MIBK | 10 | Y |  | insufficient solids/gel |
| 6004273-06-A66 | NMP | EtOAc | 10 | Y |  | insufficient solids/gel |

Table 12 (continued from Table 11)

| NB | Solvent | Anti-solvent | Anti-solvent (mL) | Precipitation? | Evap solids? | Identification |
|---|---|---|---|---|---|---|
| 6004273-06-A67 | NMP | iPrOAc | 10 | Y |  | insufficient solids/gel |
| 6004273-06-A68 | NMP | THF | 20 | N | N | insufficient solids/gel |
| 6004273-06-A69 | NMP | 2-MeTHF | 10 | Y |  | insufficient solids/gel |
| 6004273-06-A70 | NMP | 1,4-Dioxane | 20 | N | N | Type A |
| 6004273-06-A71 | NMP | MTBE | 10 | Y |  | insufficient solids/gel |
| 6004273-06-A72 | NMP | ACN | 20 | N | N | insufficient solids/gel |
| 6004273-06-A73 | NMP | DCM | 20 | N | N | insufficient solids/gel |
| 6004273-06-A74 | NMP | CHCl$_3$ | 20 | N | N | insufficient solids/gel |
| 6004273-06-A75 | NMP | Toluene | 10 | Y |  | insufficient solids/gel |
| 6004273-06-A76 | NMP | Water | 20 | N | N | insufficient solids/gel |
| 6004273-06-A77 | NMP | MEK | 20 | N | Y | Amorphous |
| 6004273-06-A78 | NMP | t-BuOH | 20 | hazy | Y | Amorphous + Type J |
| 6004273-06-A79 | NMP | n-Propanol | 20 | N | N | insufficient solids/gel |
| 6004273-06-A80 | NMP | n-Propyl acetate | 10 | Y |  | insufficient solids/gel |
| 6004273-06-A81 | DMA | EtOH | 20 | N | N | insufficient solids/gel |
| 6004273-06-A82 | DMA | IPA | 20 | hazy | Y | Type L + amorphous |
| 6004273-06-A83 | DMA | Acetone | 20 | N | Y | insufficient solids/gel |
| 6004273-06-A84 | DMA | MIBK | 10 | Y |  | Amorphous + Type J |
| 6004273-06-A85 | DMA | EtOAc | 10 | Y |  | insufficient solids/gel |
| 6004273-06-A86 | DMA | iPrOAc | 10 | Y |  | insufficient solids/gel |
| 6004273-06-A87 | DMA | THF | 20 | N | N | insufficient solids/gel |
| 6004273-06-A88 | DMA | 2-MeTHF | 10 | Y |  | insufficient solids/gel |
| 6004273-06-A89 | DMA | 1,4-Dioxane | 20 | N | N | insufficient solids/gel |
| 6004273-06-A90 | DMA | MTBE | 10 | Y |  | Amorphous + Type F |
| 6004273-06-A91 | DMA | ACN | 20 | N | N | insufficient solids/gel |
| 6004273-06-A92 | DMA | DCM | 20 | N | N | insufficient solids/gel |
| 6004273-06-A93 | DMA | CHCl$_3$ | 20 | N | N | insufficient solids/gel |
| 6004273-06-A94 | DMA | Toluene | 10 | Y |  | Amorphous + Type J |

-continued

| NB | Solvent | Anti-solvent | Anti-solvent (mL) | Precipitation? | Evap solids? | Identification |
|---|---|---|---|---|---|---|
| 6004273-06-A95 | DMA | Water | 20 | N | Y | insufficient solids/gel |
| 6004273-06-A96 | DMA | MEK | 20 | N | N | insufficient solids/gel |
| 6004273-06-A97 | DMA | t-Butanol | 20 | N | Y | Type M |
| 6004273-06-A98 | DMA | n-Propanol | 20 | N | Y | insufficient solids/gel |
| 6004273-06-A99 | DMA | n-Propyl acetate | 10 | Y | | insufficient solids/gel |

TABLE 13

| NB | Solvent | Anti-solvent | Anti-solvent (mL) | Precipitation? | Evap solids? | Identification |
|---|---|---|---|---|---|---|
| 6004273-06-A100 | NMP | 1,4-Dioxane | 20 | N | | insufficient solids/gel |
| 6004273-06-A101 | NMP | MIBK | 10 | Y | | insufficient solids/gel |
| 6004273-06-A102 | CHCl3 | EtOH | 10 | Y | | Type A |
| 6004273-06-A103 | CHCl3 | MTBE | 10 | Y | | Type A |
| 6004273-06-A104 | CHCl3 | n-Heptane | 10 | Y | | Type A |
| 6004273-06-A105 | DMSO | EtOAc | 10 | Y | | insufficient solids/gel |
| 6004273-06-A106 | DMSO | Toluene | 10 | Y | | Amorphous |
| 6004273-06-A107 | DMSO | Water | 20 | N | | insufficient solids/gel |
| 6004273-06-A108 | DMA | Acetone | 20 | N | | insufficient solids/gel |
| 6004273-06-A109 | DMA | iPrOAc | 10 | Y | | insufficient solids/gel |
| 6004273-06-A110 | DMF | IPA | 10 | Y | | Amorphous + Type K |
| 6004273-06-A111 | DMF | THF | 20 | N | | insufficient solids/gel |

Large scale studies were performed with HM30181 mesylate Type A starting material on a 200 mg scale as described below. Results are summarized in Table 14. Solids were isolated by vacuum filtration. The wet cakes from filtration from DMA, DMF, and NMP slurries were washed with 1 mL to 2 mL methanol to remove solvents. Solids were then vacuum dried at 80° C. overnight.

Figure 32:
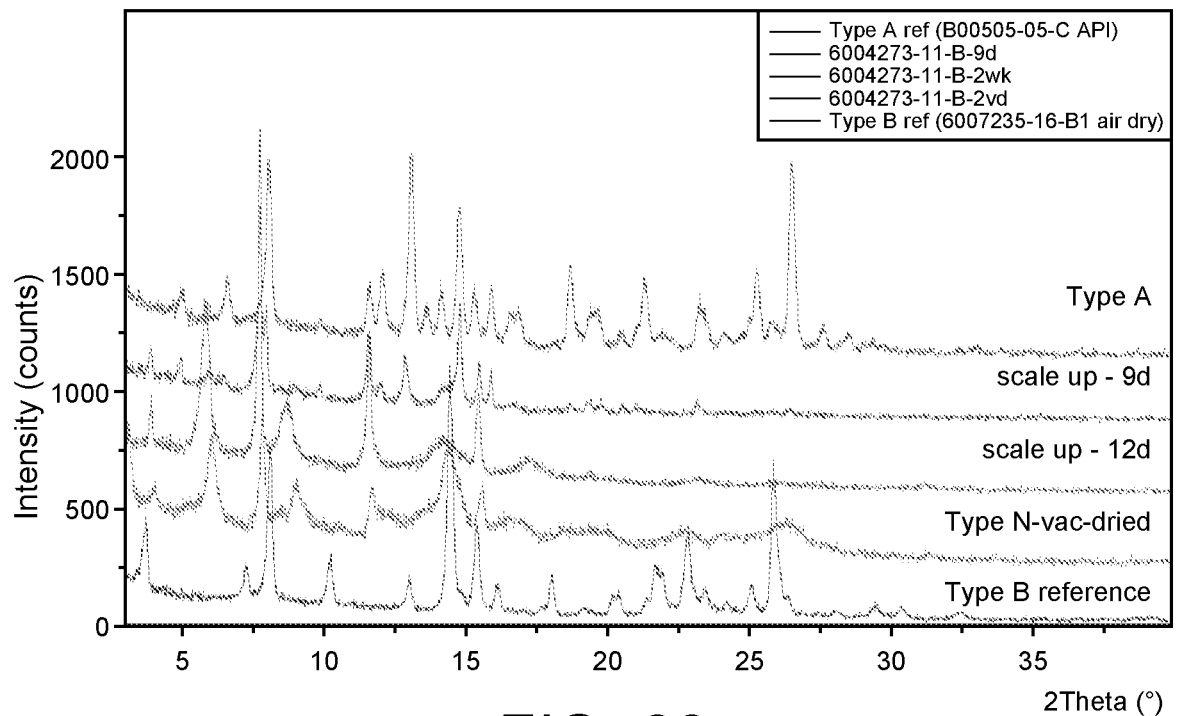
FIG. 32.
Figure 33:
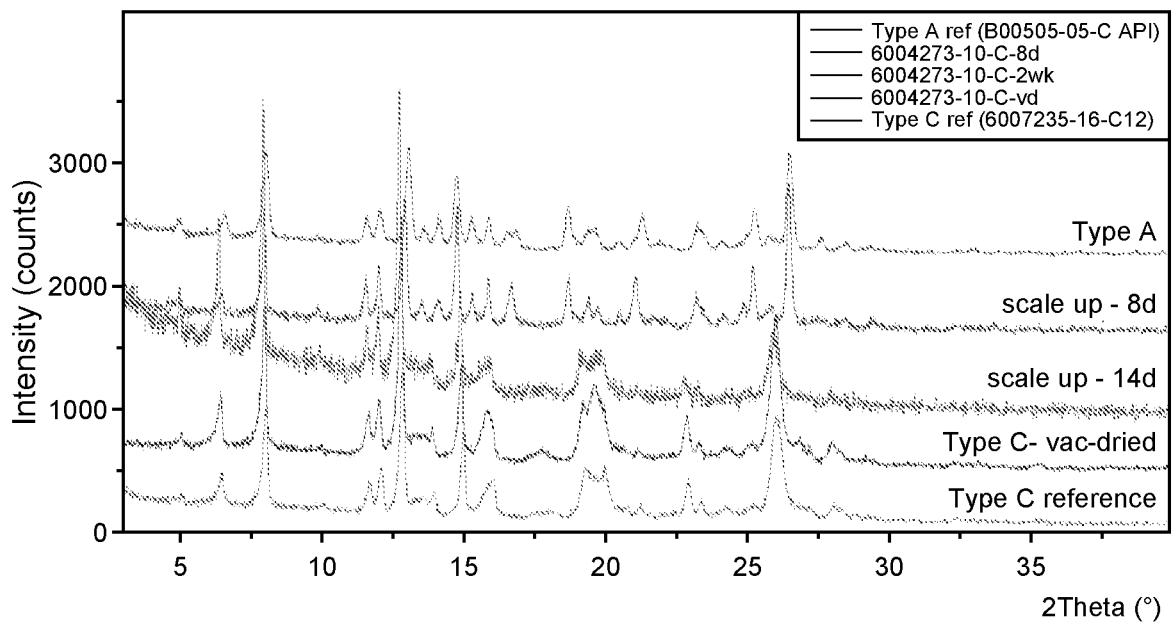
FIG. 33.
Figure 34:
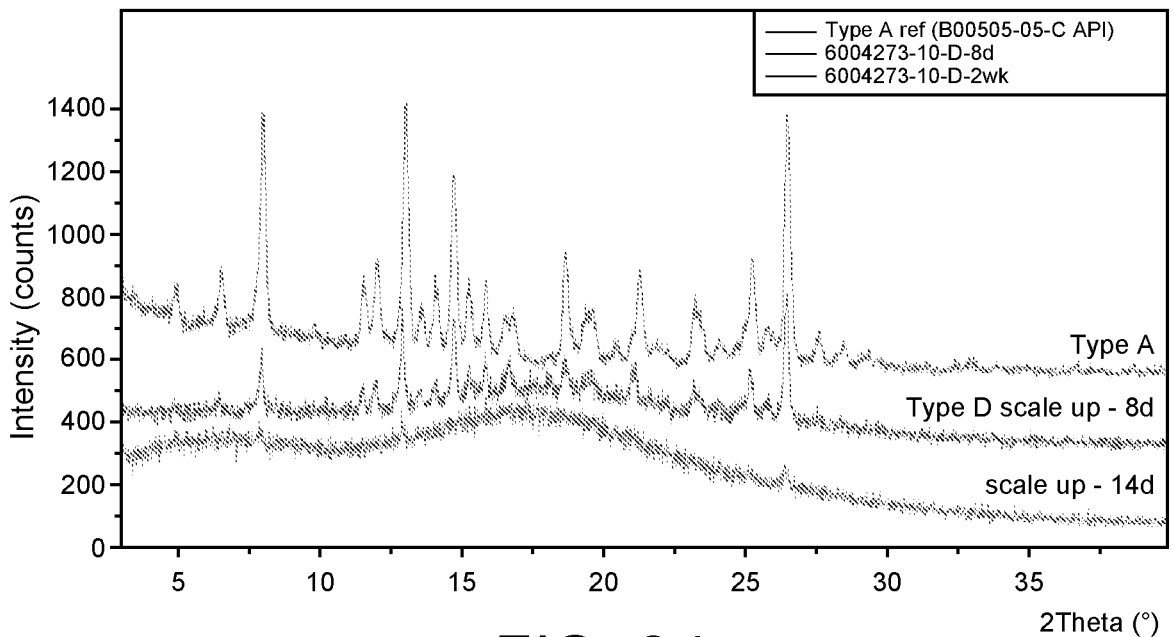
FIG. 34.
Figure 35:
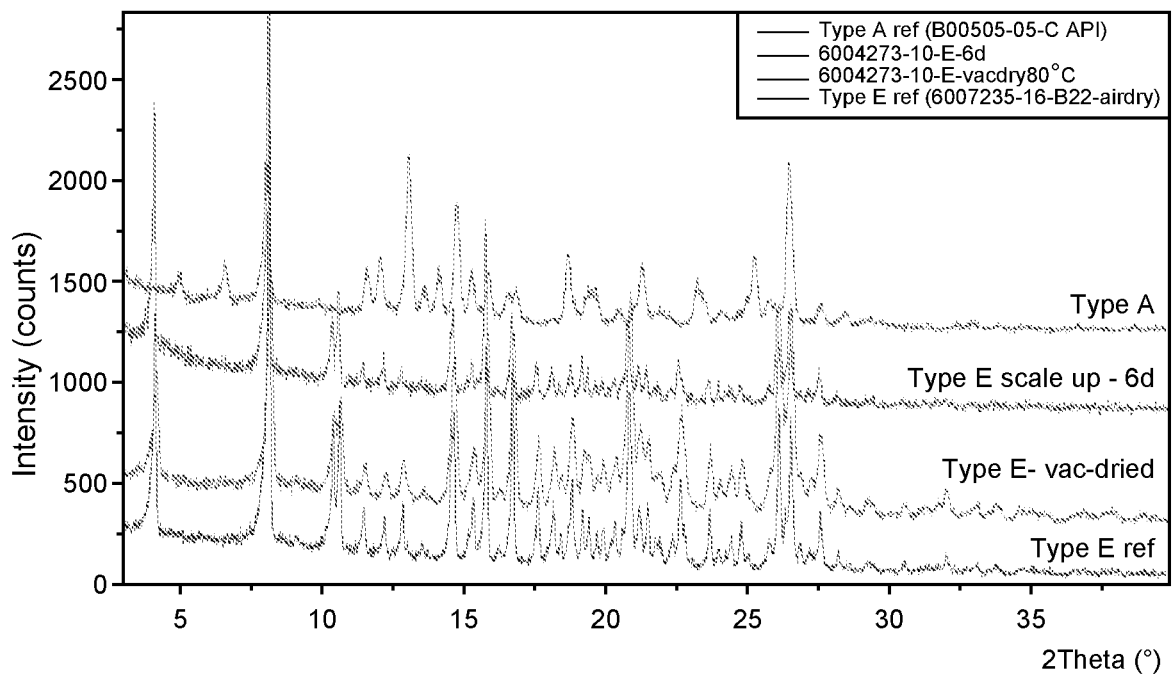
FIG. 35.
Figure 36:
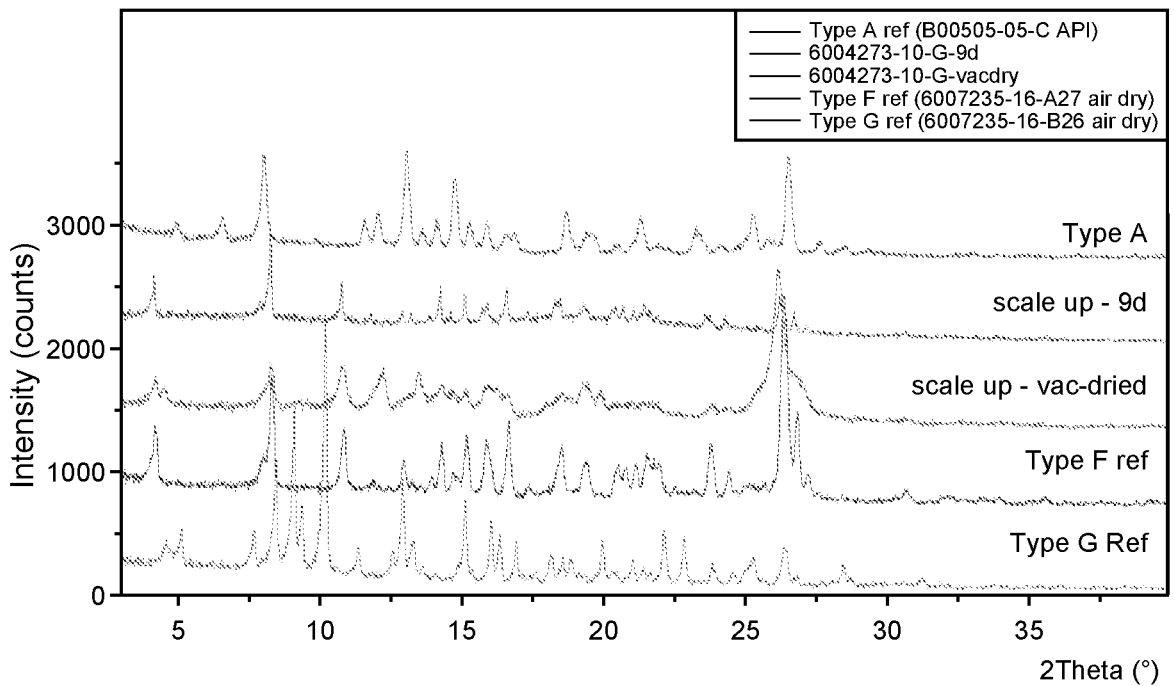
FIG. 36.
Figure 37:
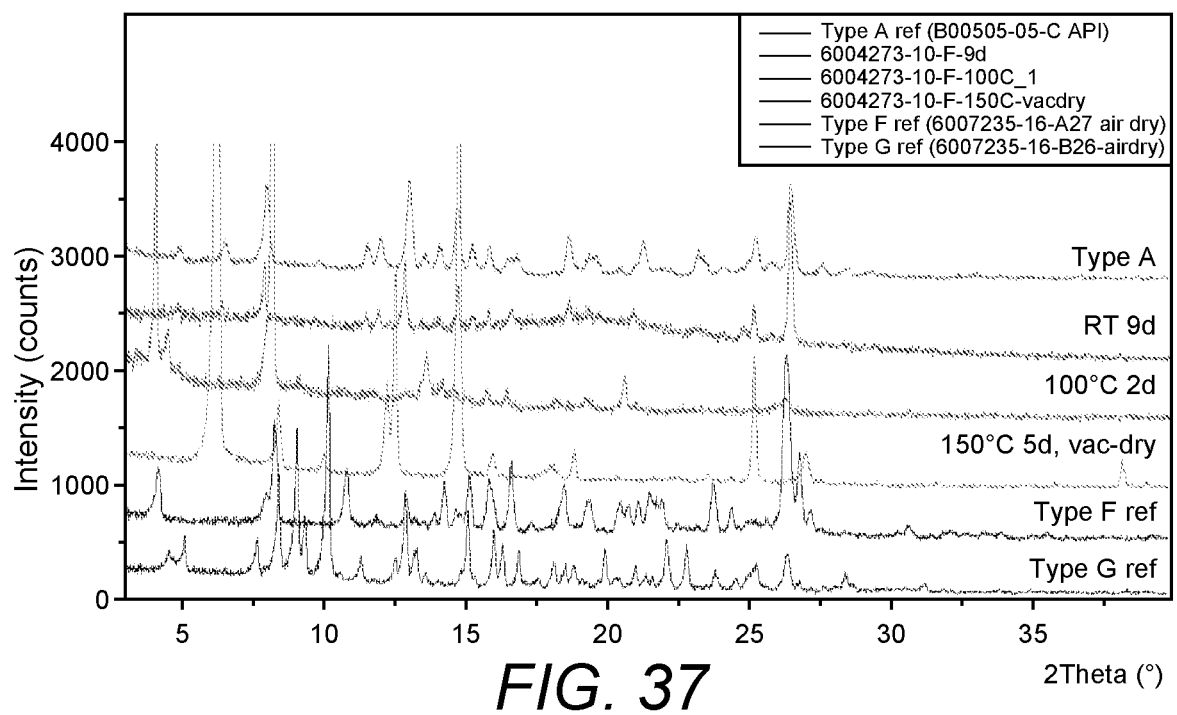
FIG. 37.
Figure 38:
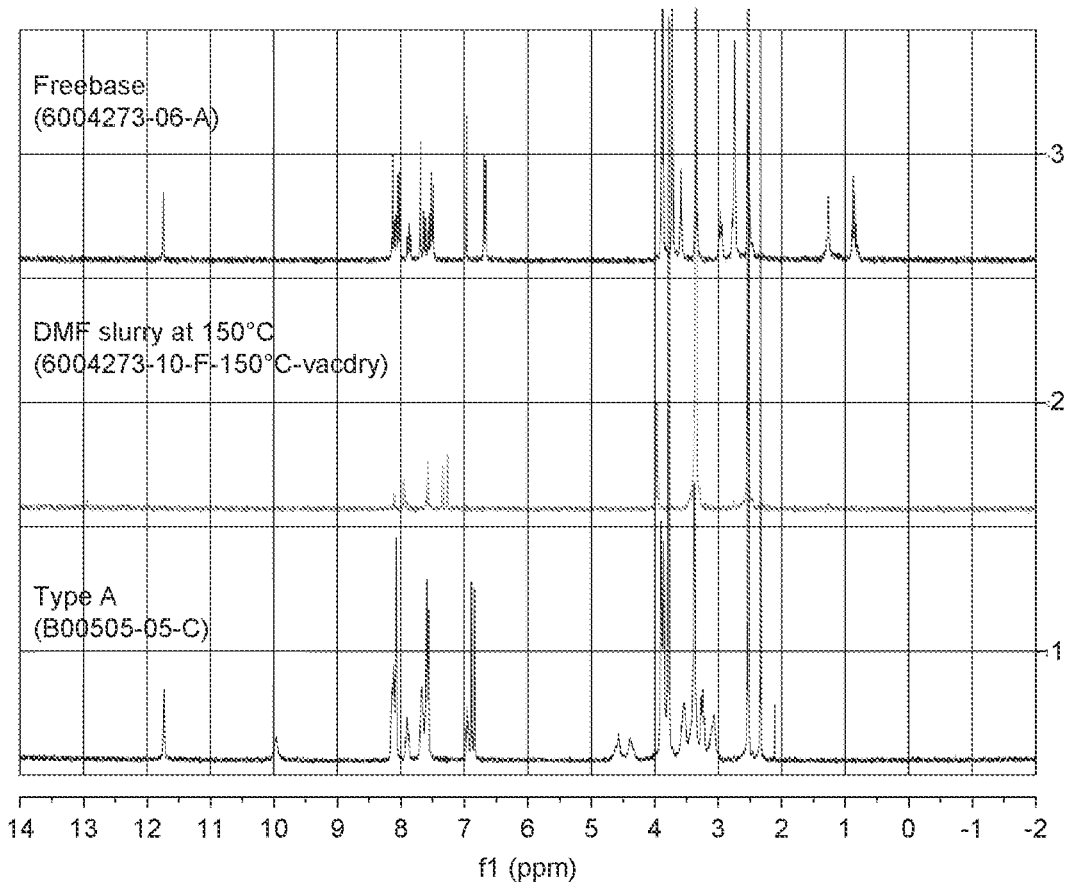
FIG. 38.

At large scale, a slurry of HM30181 mesylate Type A starting material in methanol at ambient conditions generated a mixture of HM30181 mesylate Type B and HM30181 mesylate Type A after 9 days (see FIG. 32). After 14 days, the slurry in methanol generated a HM30181 mesylate Type N polymorph. HM30181 mesylate Type N showed some loss of crystallinity after vacuum-drying, suggesting a methanol solvate (see FIG. 32). A slurry of HM30181 mesylate Type A starting material in acetonitrile at ambient conditions generated HM30181 mesylate Type C after 14 days; no loss of crystallinity was detected after vacuum-drying (see FIG. 33). A scaled-up slurry of HM30181 mesylate Type A starting material in NMP provided a primarily amorphous material (see FIG. 34). A scaled-up slurry of HM30181 mesylate Type A starting material in DMA yielded HM30181 mesylate Type E after 6 days (see FIG. 35). HM30181 mesylate Type E showed no loss of crystallinity after vacuum drying. A scaled-up slurry of HM30181 mesylate Type A starting material in DMF at 50° C. yielded HM30181 mesylate Type F rather than the expected HM30181 mesylate Type G after 9 days (see FIG. 36). Some change of pattern was noted after vacuum-drying. A scaled-up slurry of HM30181 mesylate Type A starting material in DMF at ambient temperature initially showed no change from Type A (see FIG. 37). This slurry was heated in an attempt to generate HM30181 mesylate Type G. A scaled-up slurry of HM30181 mesylate Type A starting material in DMF at 100° C. yielded HM30181 mesylate Type F after 2 days (see FIG. 37). A scaled-up slurry of HM30181 mesylate Type A starting material in DMF at 150° C. yielded a previously unobserved XRPD pattern after 5 days (see FIG. 37). $^1$H-NMR results in DMSO-$d_6$ suggested that the DMF slurry at 150° C. resulted in degradation, as the $^1$H-NMR spectrum did not match either the starting material or freebase (see FIG. 38).

Figure 39:
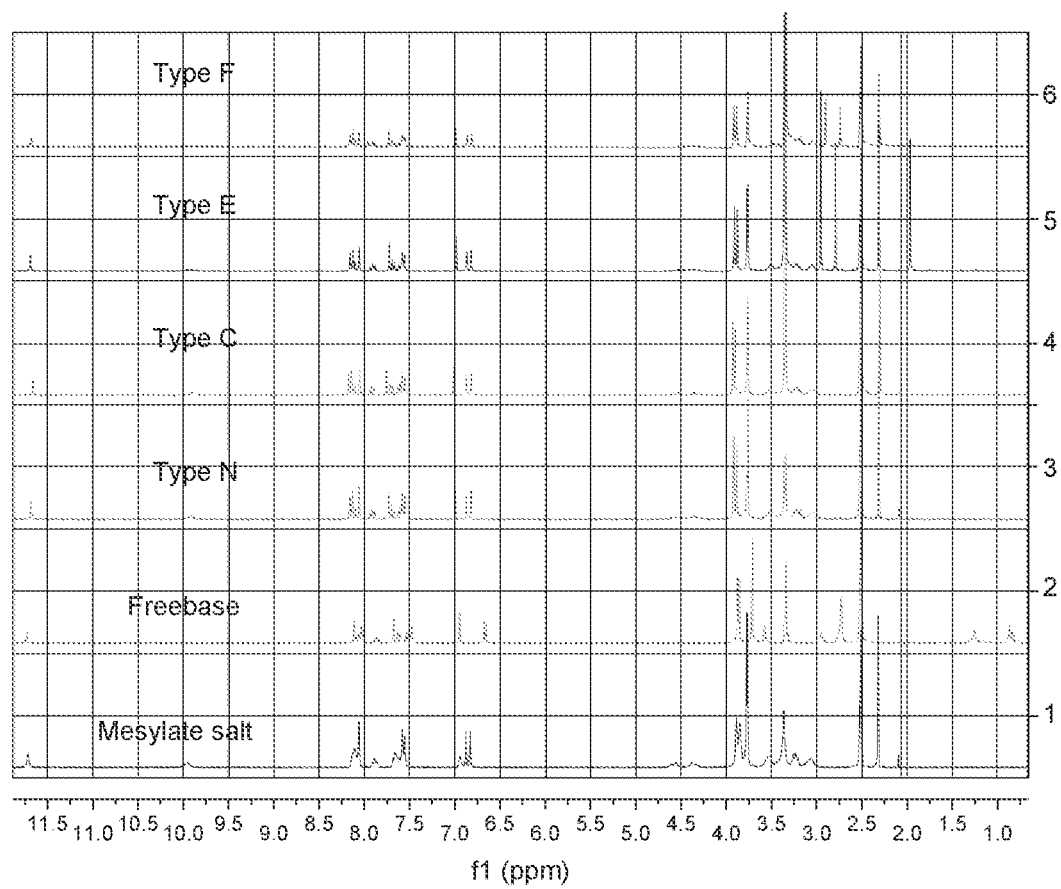
FIG. 39.

By $^1$H-NMR, no disproportionation or degradation was detected in HM30181 mesylate Types C, E, F and N polymorphs (see FIG. 39). By $^1$H-NMR, HM30181 mesylate Type E contained DMA, HM30181 mesylate Type F contains DMF, and HM30181 mesylate Type N contains MeOH.

TABLE 14

| NB | Method | Solvent | Solvent (mL) | Conc. (mg/mL) | Anti-solvent | Anti-solvent (mL) | Desired Type | Observations |
|---|---|---|---|---|---|---|---|---|
| 6004273-10-B | Slurry at ambient temperature | MeOH | 0.2 | 480 | | | B | Type N |
| 6004273-10-C | Slurry at ambient temperature | MeCN | 0.2 | 545 | | | C | Type C |
| 6004273-10-D | Slurry at ambient temperature | NMP | 0.2 | 550 | | | D | Amorphous |
| 6004273-10-E | Slurry at ambient temperature | DMA | 0.2 | 576 | | | E | Type E |
| 6004273-10-F | Slurry at ambient temperature | DMF | 0.2 | 595 | | | F | Type A |
| 6004273-10-F-100C | Slurry at 100° C. (for 2 days) | DMF | 0.2 | 595 | | | G | Type F |
| 6004273-10-F-150C | Slurry at 150° C. (for 5 d) | DMF | 0.2 | 595 | | | G | Decomposition |
| 6004273-10-G | Slurry at 50° C. | DMF | 0.2 | 576 | | | G | Type F |
| 6004273-10-H | Liquid vapor sorption | DMSO | 5 | 60 | MeCN | 3 | H | No precipitation, evaporated- no solids due to DMSO |
| 6004273-10-J | Liquid vapor sorption | DMSO | 10 | 60 | Acetone | 3 | J | No precipitation, evaporated- no solids due to DMSO |
| 6004273-10-K | Anti-solvent addition | DMSO | 10 | 60 | MIBK | 200 | K | Amorphous |
| 6004273-10-L | Anti-solvent addition | DMF | 20 | 5 | n-propanol | 200 | L | Amorphous |
| 6004273-10-M | Anti-solvent addition | DMA | 20 | 5 | t-BuOH | 200 | M | Amorphous |
| 6004273-10-M1 | Anti-solvent addition | DMF | 20 | 5 | Toluene | 300 | M | Amorphous |

Characteristics of HM30181 mesylate salt polymorphisms as characterized by XRPD, TGA, DSC, and DVS are summarized below:

HM30181 mesylate Type A represents a prior art preparation of HM30181 mesylate that can be used as a starting material in generation of novel polymorphs of this compound.

Figure 40:
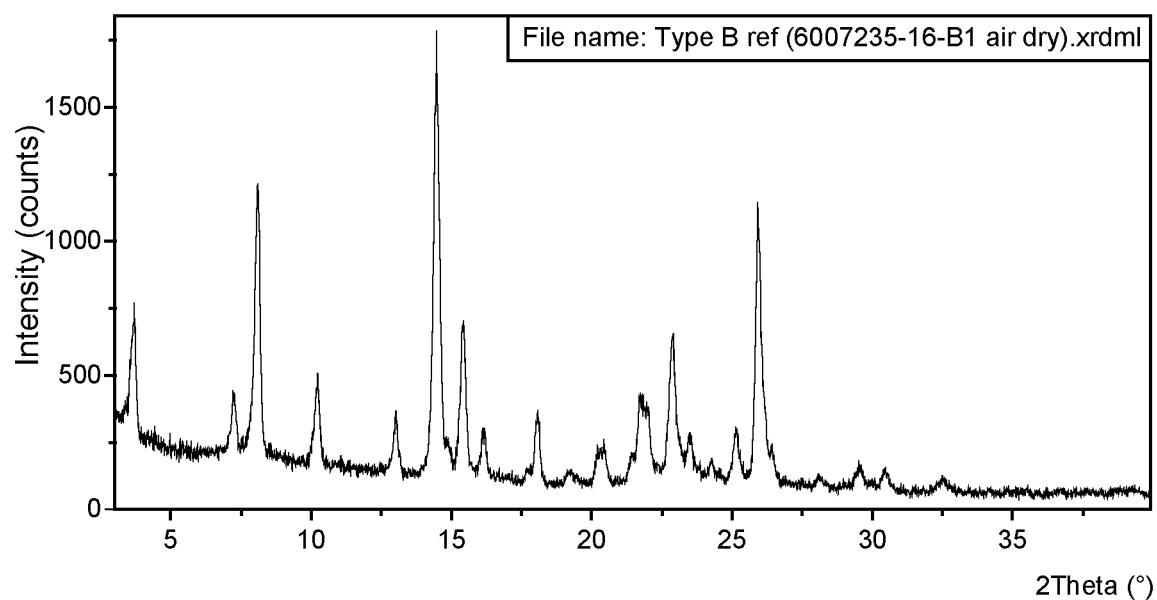
FIG. 40.
Figure 41:
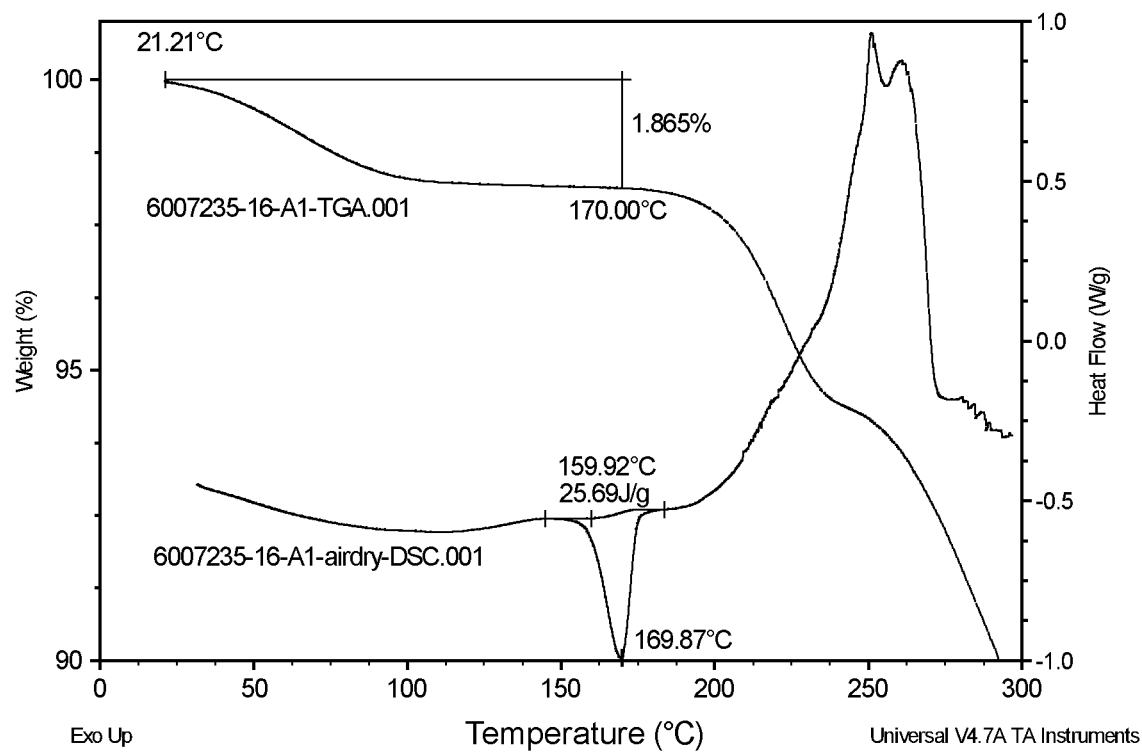
FIG. 41.

Crystalline HM30181 mesylate Type B was obtained through slurrying in methanol at 4° C. to 50° C. and is distinct by XRPD (see FIG. 40). By DSC, HM30181 mesylate Type B displayed an endotherm at 159.92° C. (see FIG. 41). By TGA, HM30181 mesylate Type B showed 1.865% weight loss before 170° C., followed by possible disassociation and decomposition (see FIG. 41).

Figure 42:
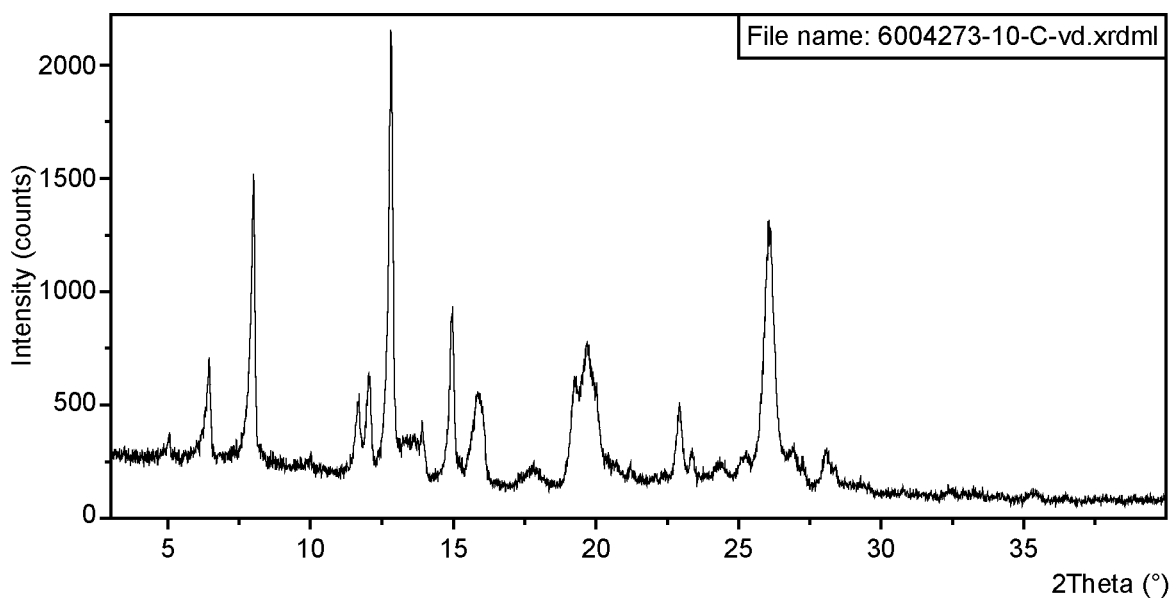
FIG. 42.
Figure 43:
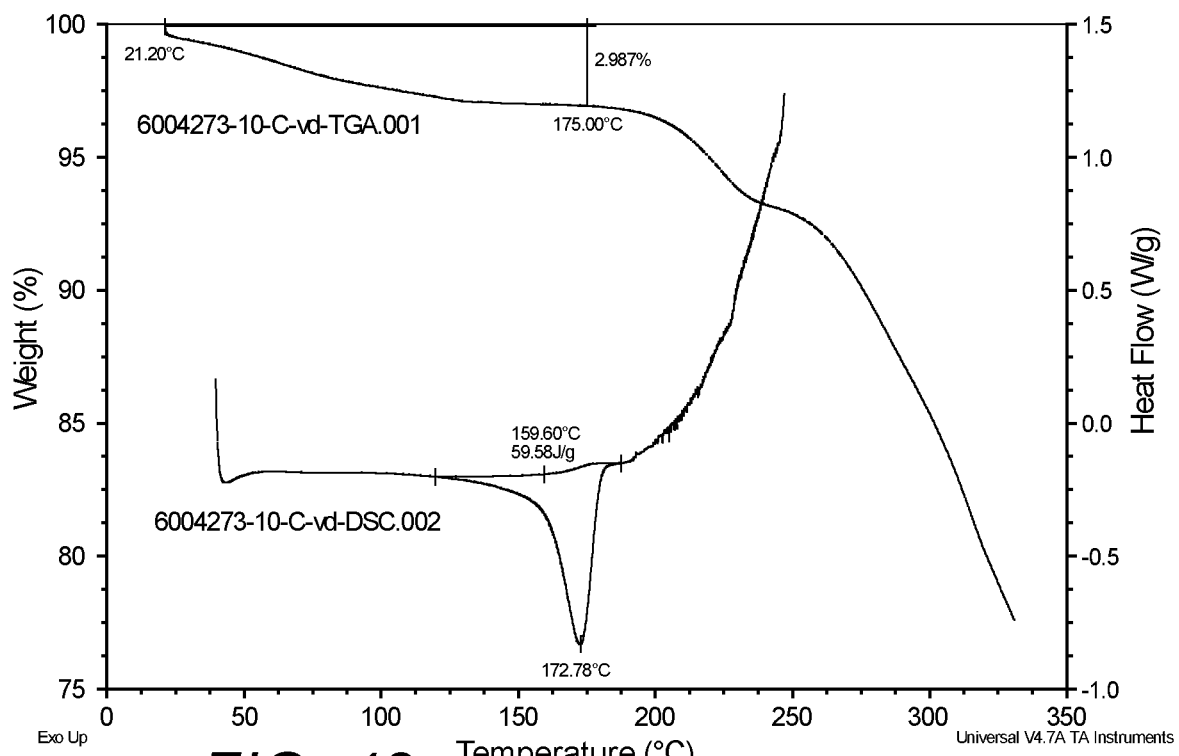
FIG. 43.
Figure 44:
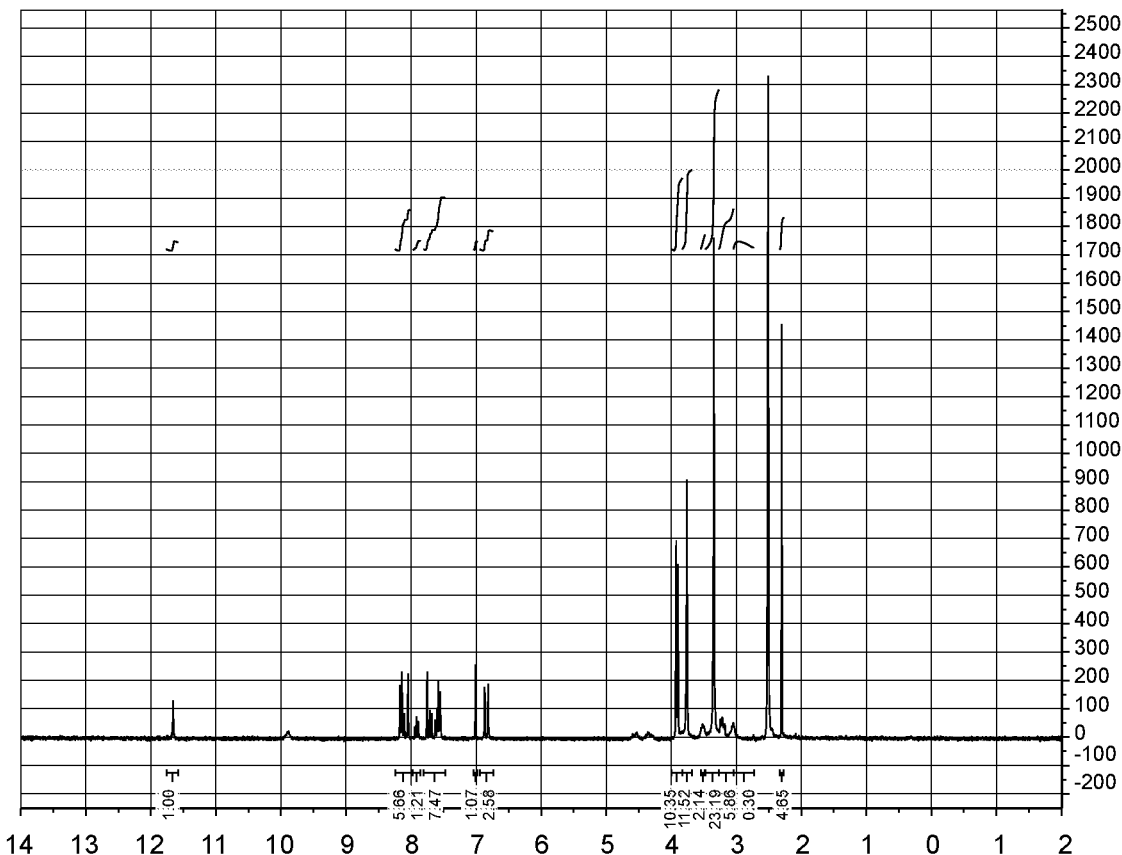
FIG. 44.

Crystalline HM30181 mesylate Type C polymorph was obtained through slurrying in acetonitrile at ambient temperature and shows characteristic results on XRPD. No change in crystalline pattern was noted after vacuum drying overnight (see FIG. 42). By DSC, HM30181 mesylate Type C displays an endotherm at 159.60° C. (see FIG. 43). By TGA, HM30181 mesylate Type C showed 2.987% weight loss before 170° C., followed by a disassociation and decomposition (see FIG. 43). By 1H-NMR, HM30181 mesylate Type C is confirmed to contain only water and no acetonitrile, (~2.07 ppm) suggesting a monohydrate (see FIG. 44).

Figure 45:
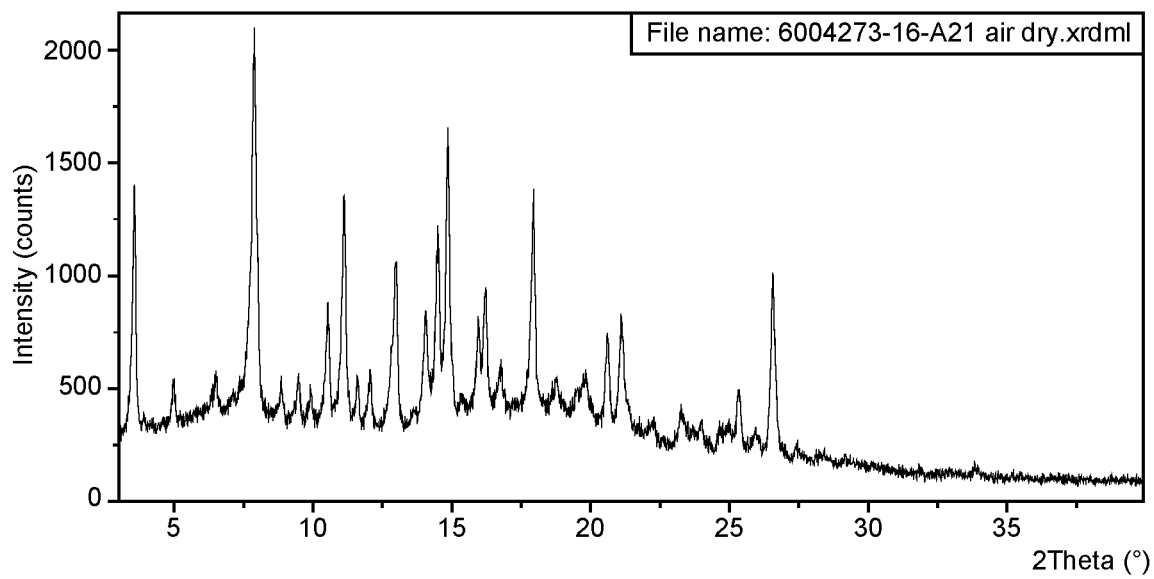
FIG. 45.
Figure 46:
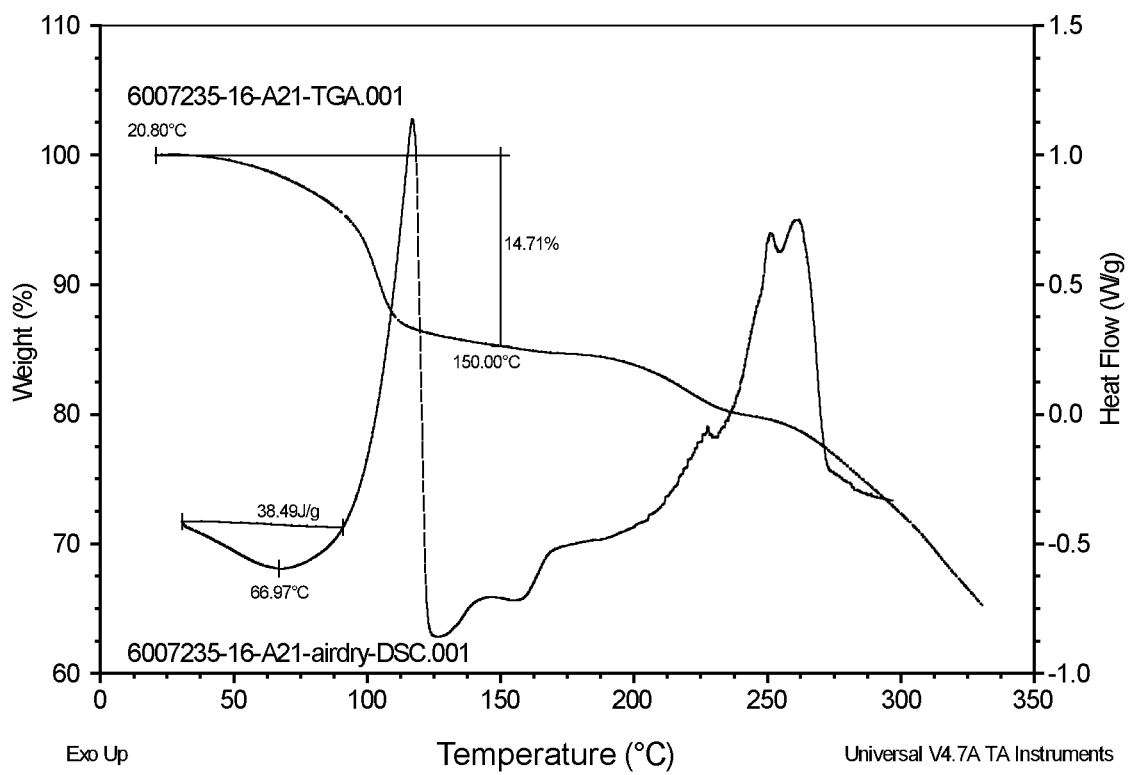
FIG. 46.

Crystalline HM30181 mesylate Type D was obtained through slurrying in N-methyl pyrrolidone at ambient temperature and shows characteristic results by XRPD. No change in crystalline pattern was noted after air drying overnight (see FIG. 45). By DSC/TGA, HM30181 mesylate Type D displayed an endotherm at 66.97° C. and a 14.71% weight loss before 150° C., suggesting significant residual solvent content (see FIG. 46).

Figure 47:
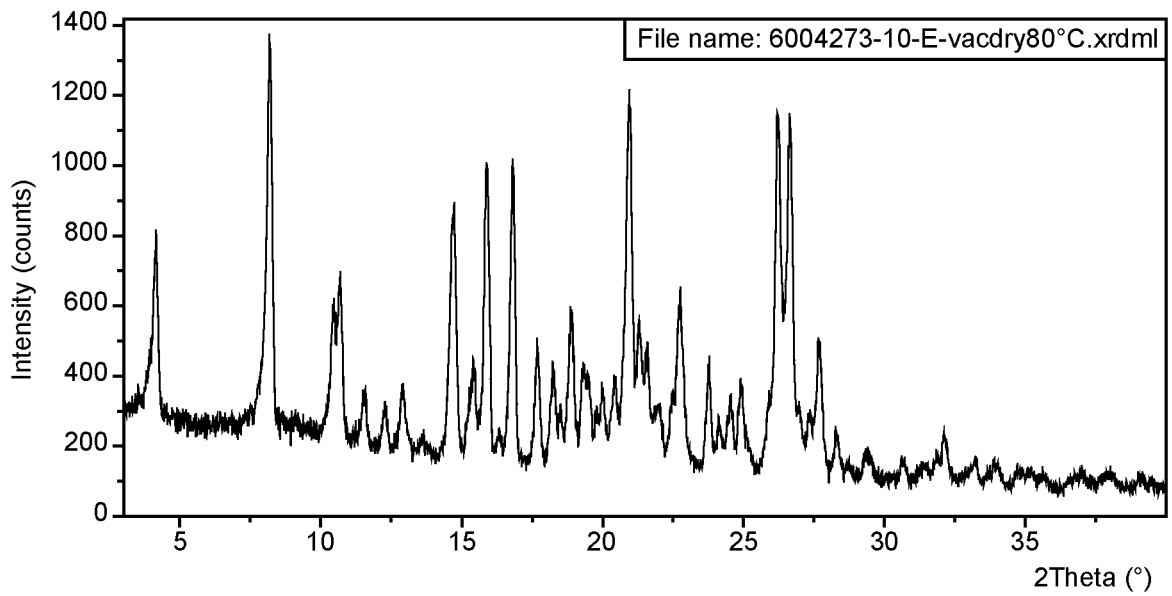
FIG. 47.
Figure 48:
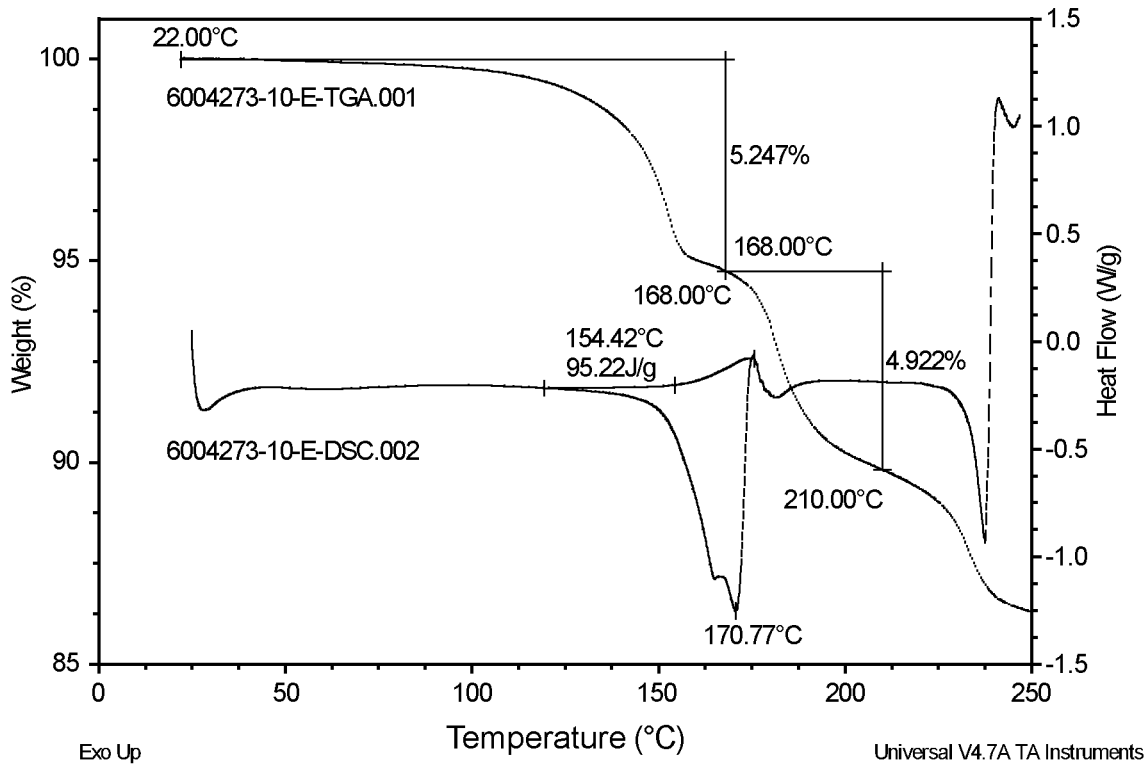
FIG. 48.
Figure 49:
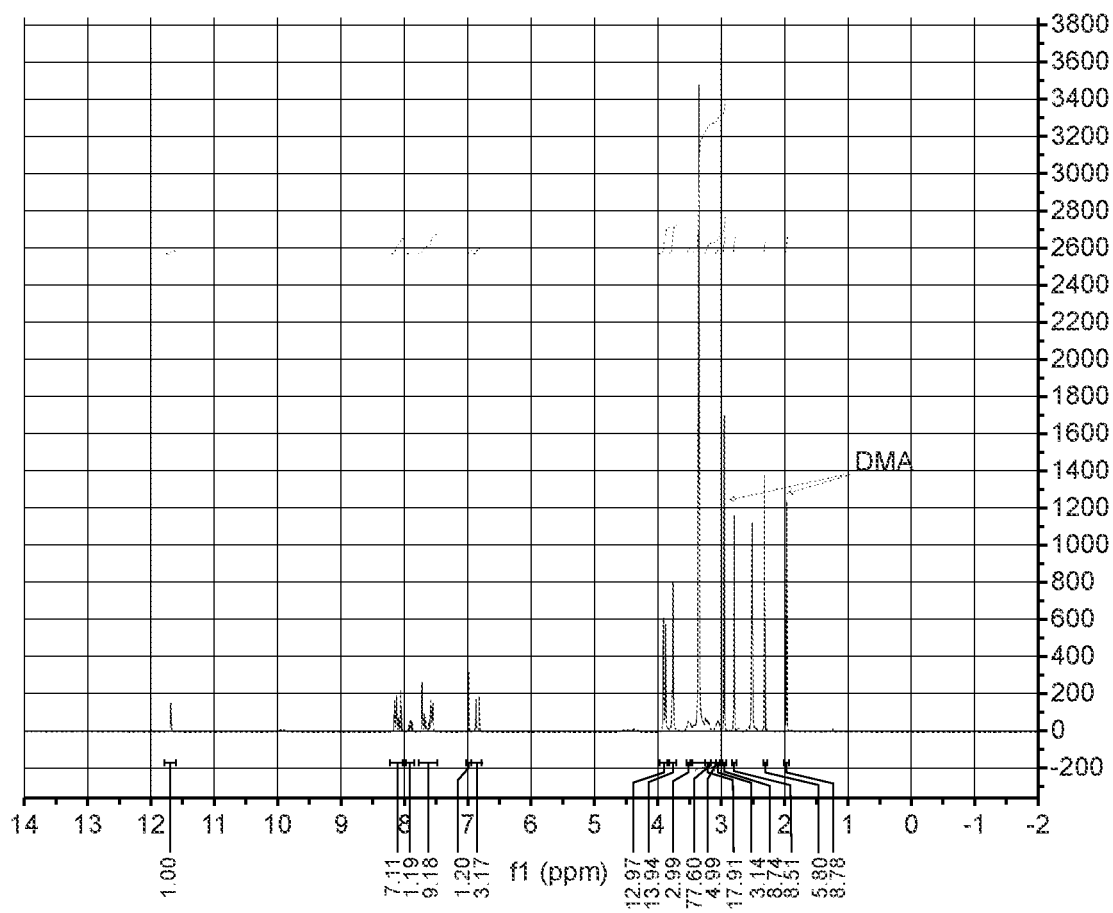
FIG. 49.

Crystalline HM30181 mesylate Type E was obtained through slurrying in N,N-dimethylacetamide at ambient temperature and shows characteristic results by XRPD. No change in crystalline pattern was noted after vacuum drying overnight at 80° C. (see FIG. 47). By DSC/TGA, HM30181 mesylate Type E displayed an endotherm at 154.42° C. and a 5.247% weight loss before 168° C., suggesting HM30181 mesylate Type E was a solvate (see FIG. 48). By $^1$H-NMR, HM30181 mesylate Type E was confirmed to contain DMA (see FIG. 49).

Figure 50:
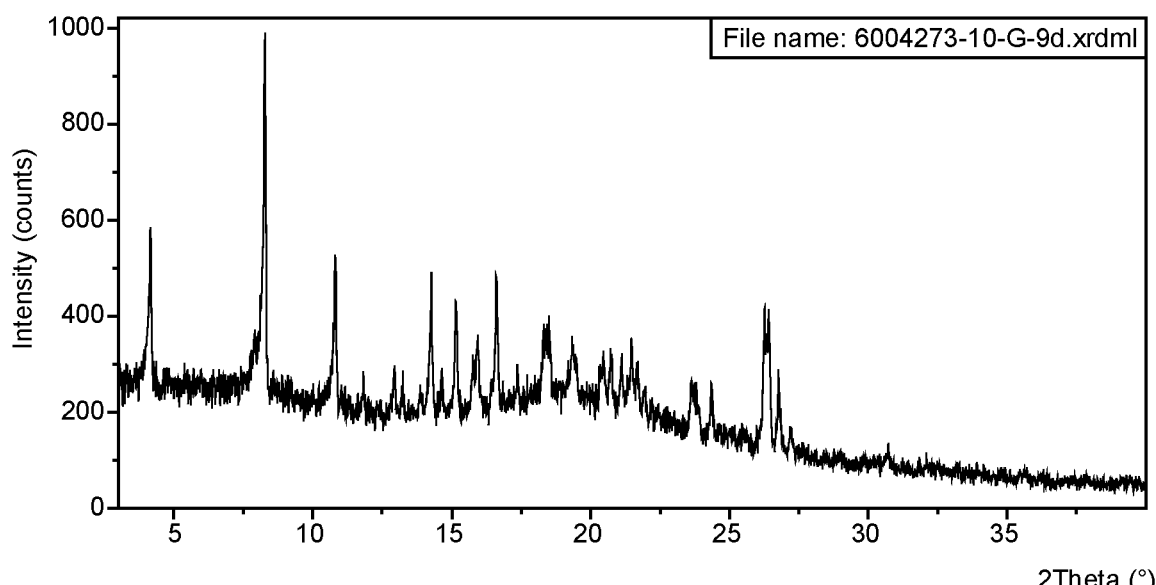
FIG. 50.
Figure 51:
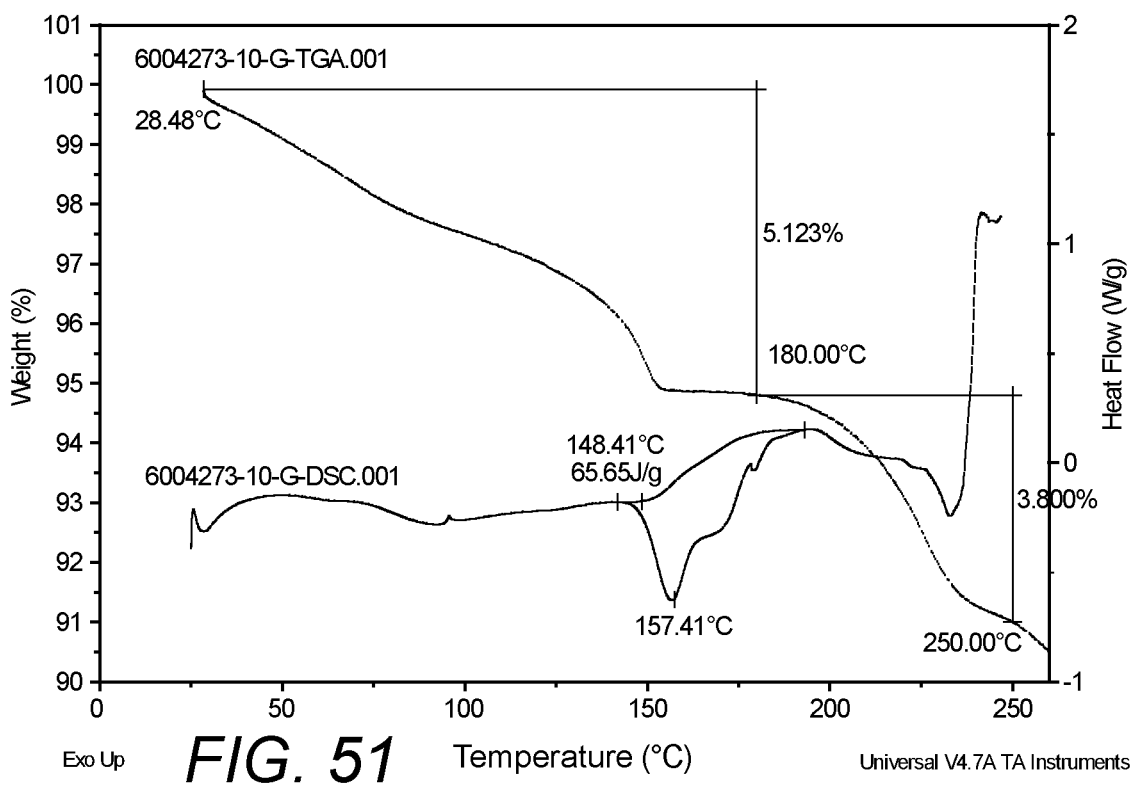
FIG. 51.
Figure 52:
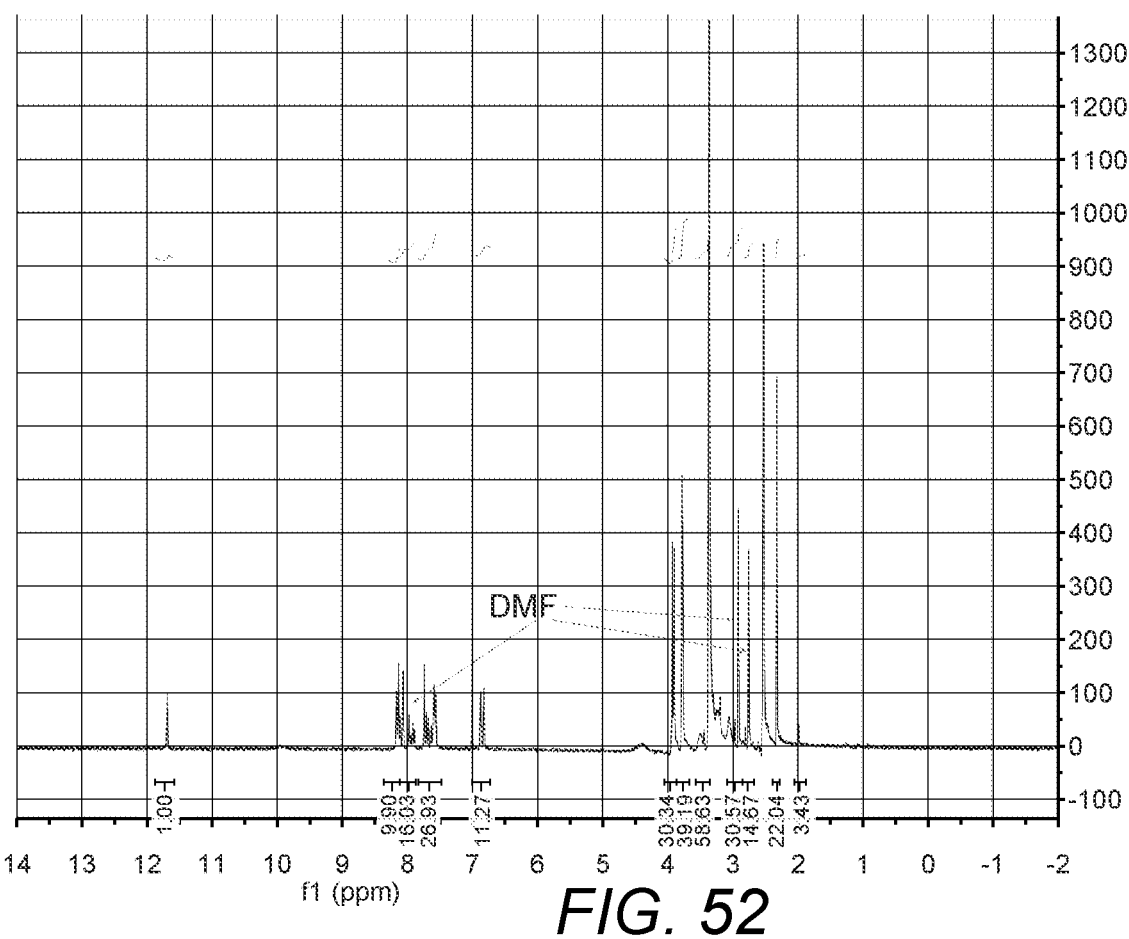
FIG. 52.

Crystalline HM30181 mesylate Type F was obtained through slurrying in dimethylformamide at 50° C. and shows characteristic results by XRPD (see FIG. 50). A significant reduction in crystallinity was noted after vacuum drying overnight at 80° C., suggesting HM30181 mesylate Type F is a metastable solvate. By DSC/TGA, HM30181 mesylate Type F displayed an endotherm at 148.41° C. and a 5.123% weight loss before 180° C., consistent with loss of DMF (see FIG. 51). By $^1$H-NMR, HM30181 mesylate Type F was confirmed to contain DMF (see FIG. 52).

Figure 53:
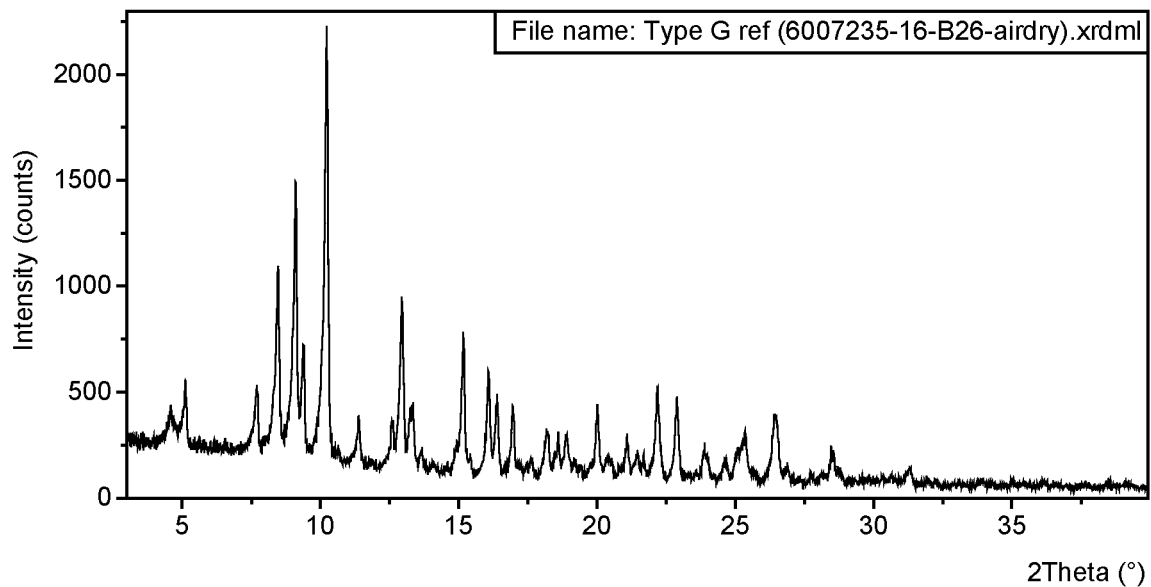
FIG. 53.
Figure 54:
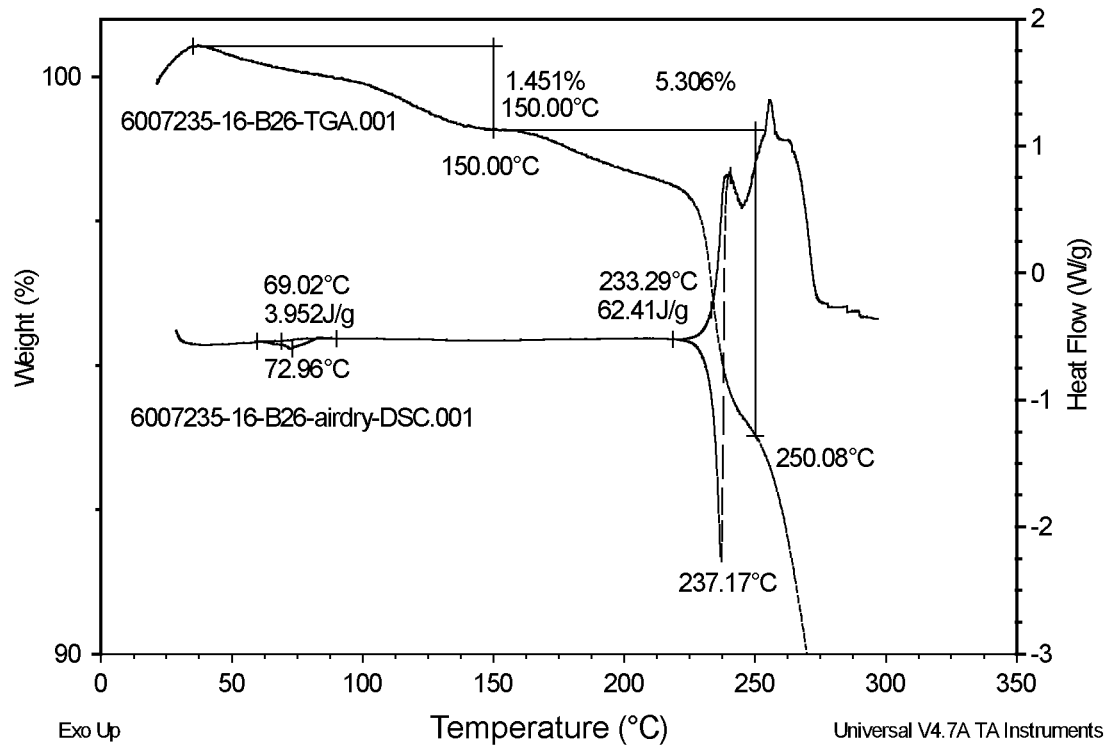
FIG. 54.

Crystalline HM30181 mesylate Type G was obtained through slurrying in dimethylformamide at 50° C. and shows characteristic results by XRPD. No reduction in crystallinity was noted after air drying overnight (see FIG. 53). By DSC/TGA, HM30181 mesylate Type G displayed an endotherm at 69.02° C. and at 233.29° C. and a 1.451% weight loss before 150° C., which was consistent with loss of DMF (see FIG. 54).

Figure 55:
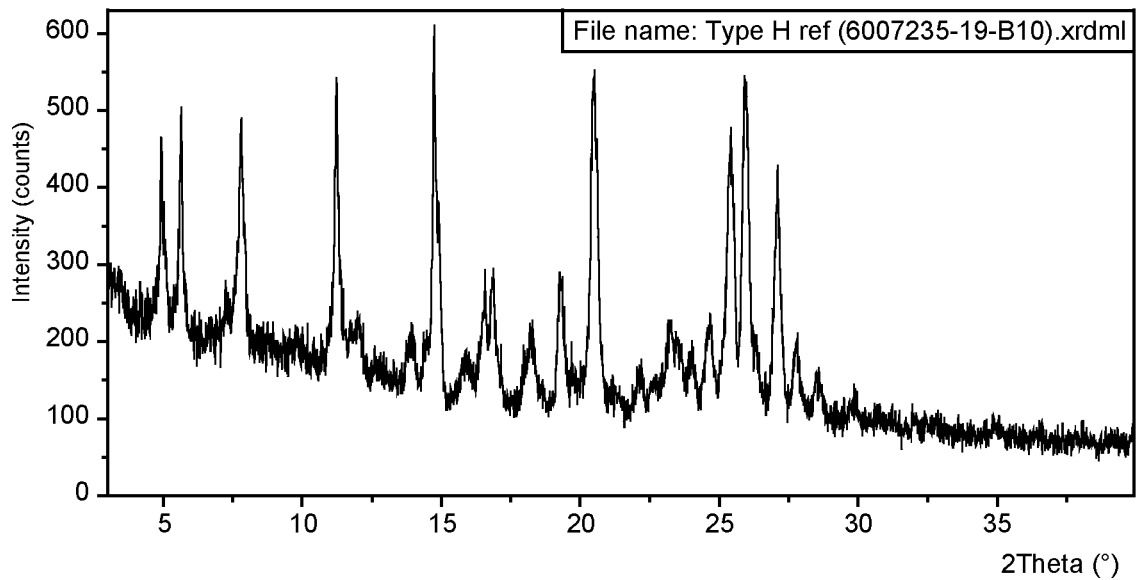
FIG. 55.
Figure 56:
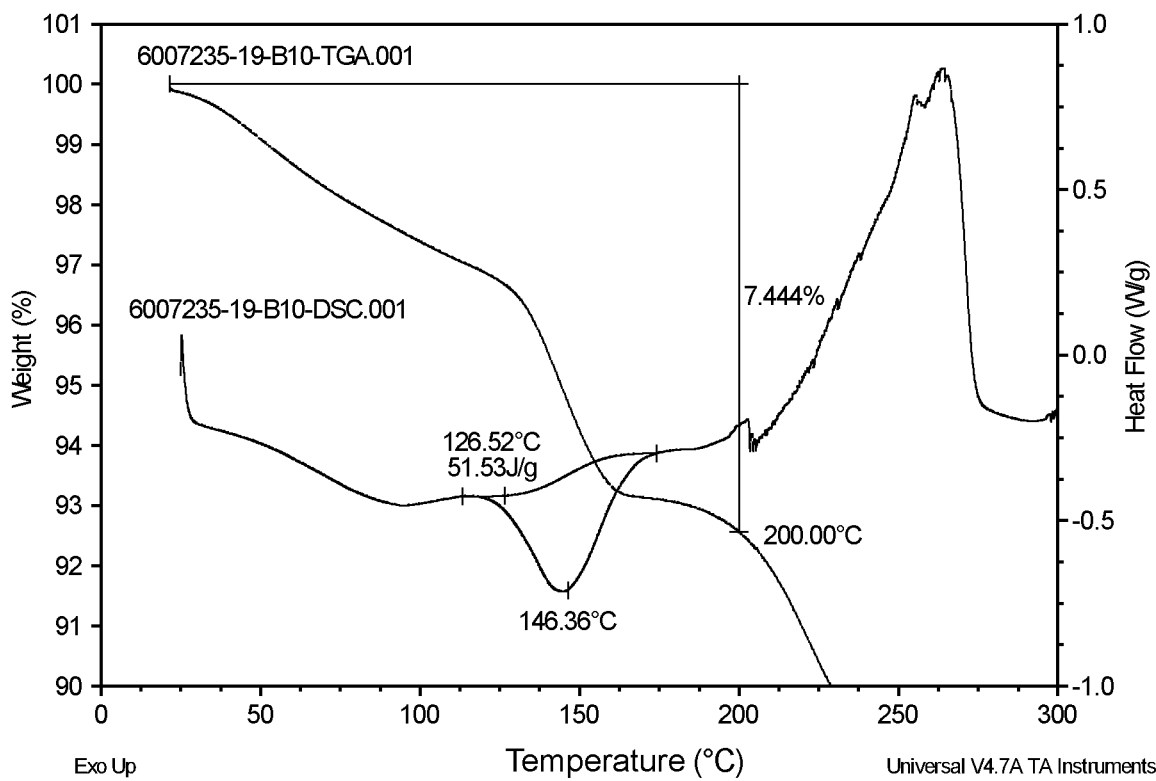
FIG. 56.

Crystalline HM30181 mesylate Type H was obtained through liquid vapor diffusion of acetonitrile into a DMSO stock of HM30181 mesylate and shows characteristic results by XRPD (see FIG. 55). By DSC/TGA, HM30181 mesylate Type H displayed an endotherm at 126.52° C. and a 7.444% weight loss before 200° C., potentially from residual ACN and DMSO or from a solvate (see FIG. 56).

Figure 57:
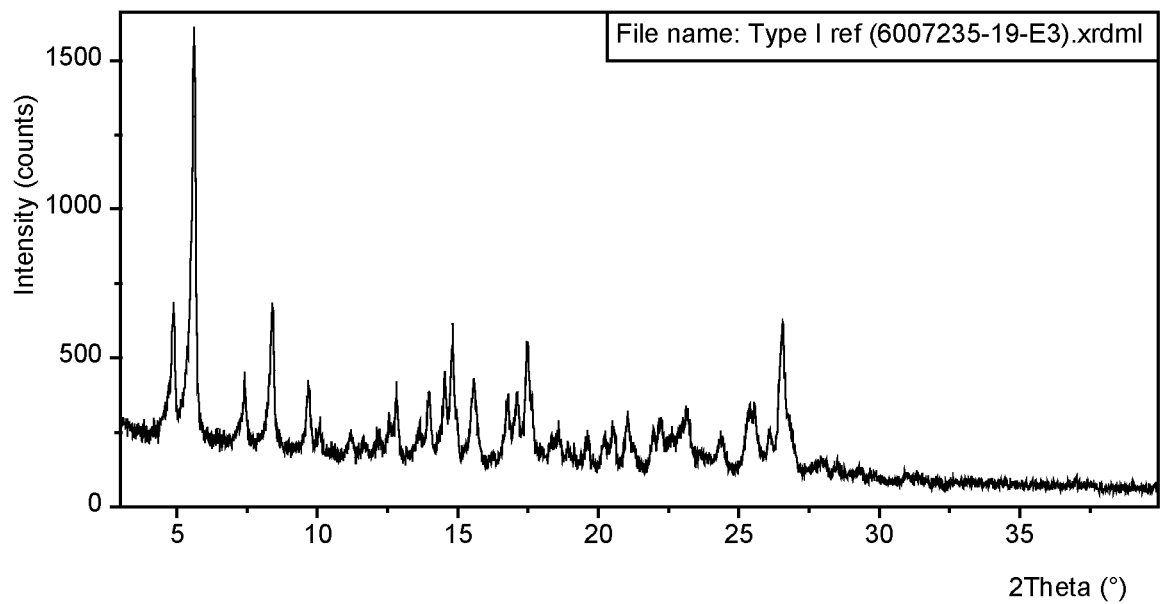
FIG. 57.

Crystalline HM30181 mesylate Type I was obtained through liquid vapor diffusion of acetone, ethyl acetate, or isopropyl acetate into a DMA stock of HM30181 mesylate and shows characteristic results by XRPD (see FIG. 57). Air-drying of HM30181 mesylate Type I yielded HM30181 mesylate Type J.

Figure 58:
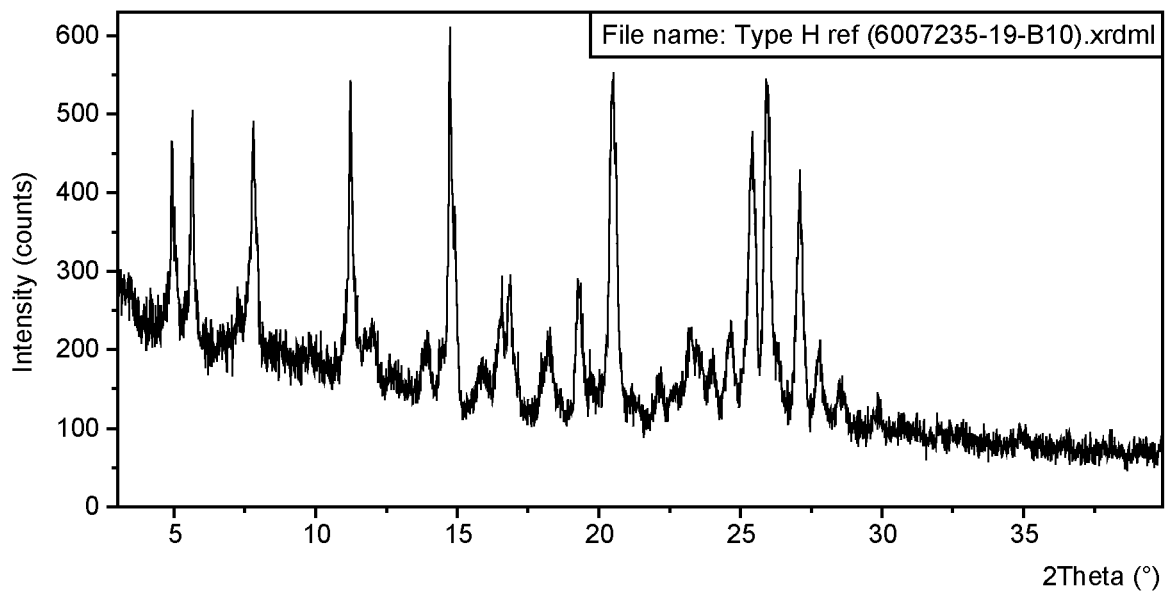
FIG. 58.
Figure 59:
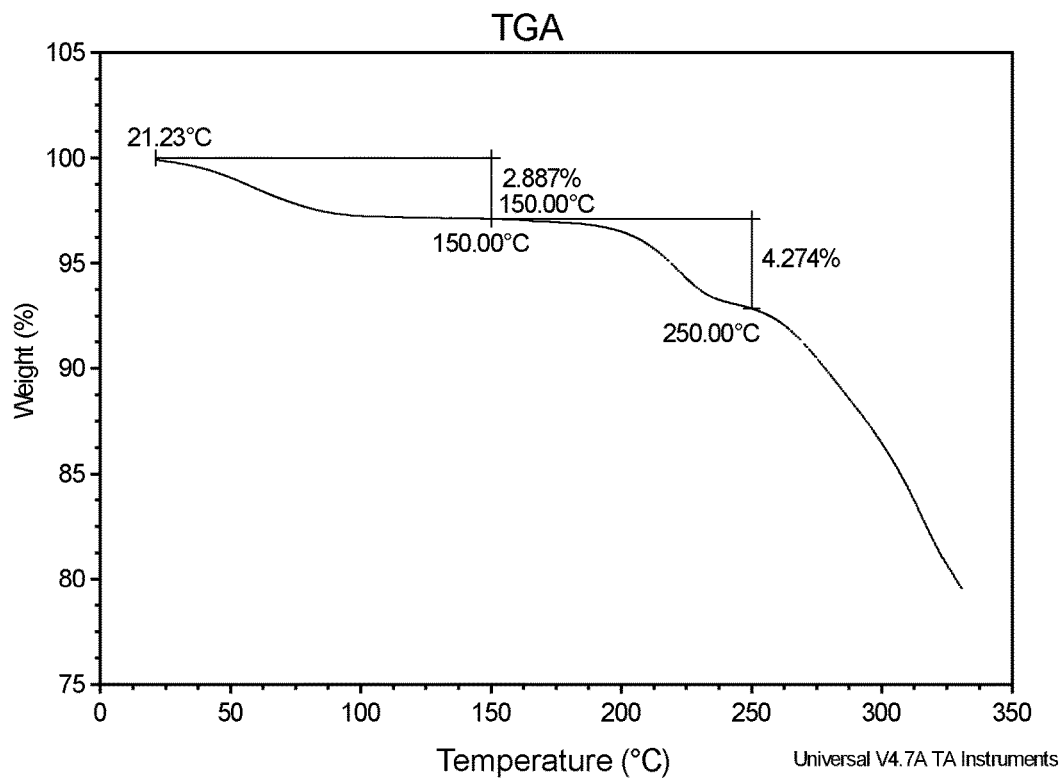
FIG. 59.

HM30181 mesylate Type J was obtained through liquid vapor diffusion of acetone, ethyl acetate, or isopropyl acetate into a DMA stock or isopropyl acetate into a DMSO stock of HM30181 mesylate followed by air-drying. By XRPD, HM30181 mesylate Type J is crystalline (see FIG. 58). By TGA, HM30181 mesylate Type J displayed a 2.887% weight loss before 150° C., suggesting a solvate or hydrate (see FIG. 59).

Figure 60:
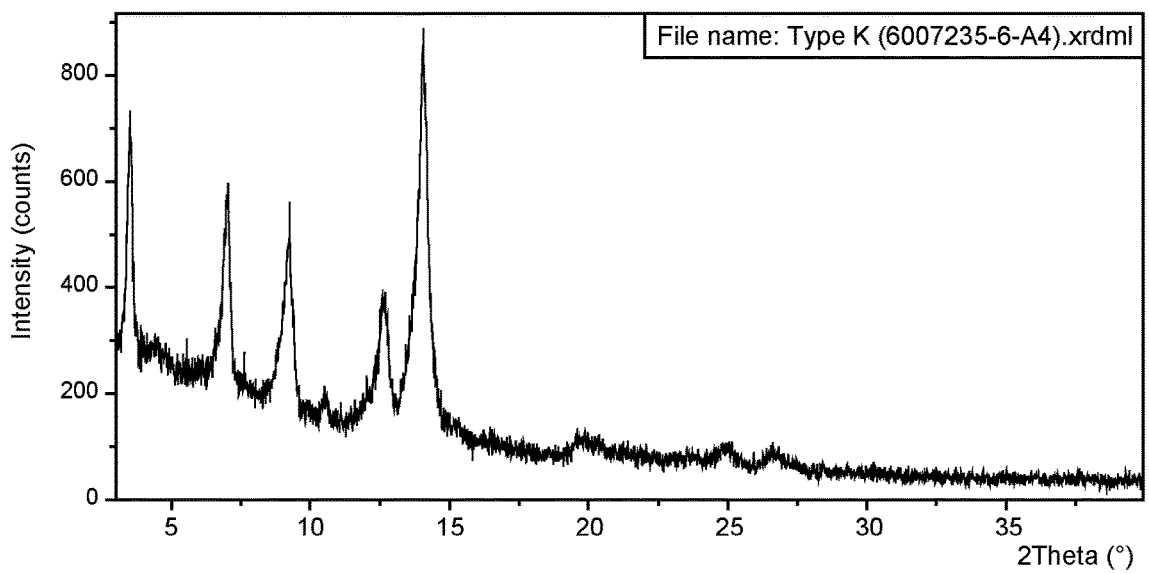
FIG. 60.

HM30181 mesylate type K was obtained through antisolvent addition using DMF/IPA and multiple DMSO systems (ethanol, acetone, MIBK, THF, chloroform, t-butanol, n-propyl acetate, and n-propanol). By XRPD, HM30181 mesylate Type K is partially crystalline (see FIG. 60).

Figure 61:
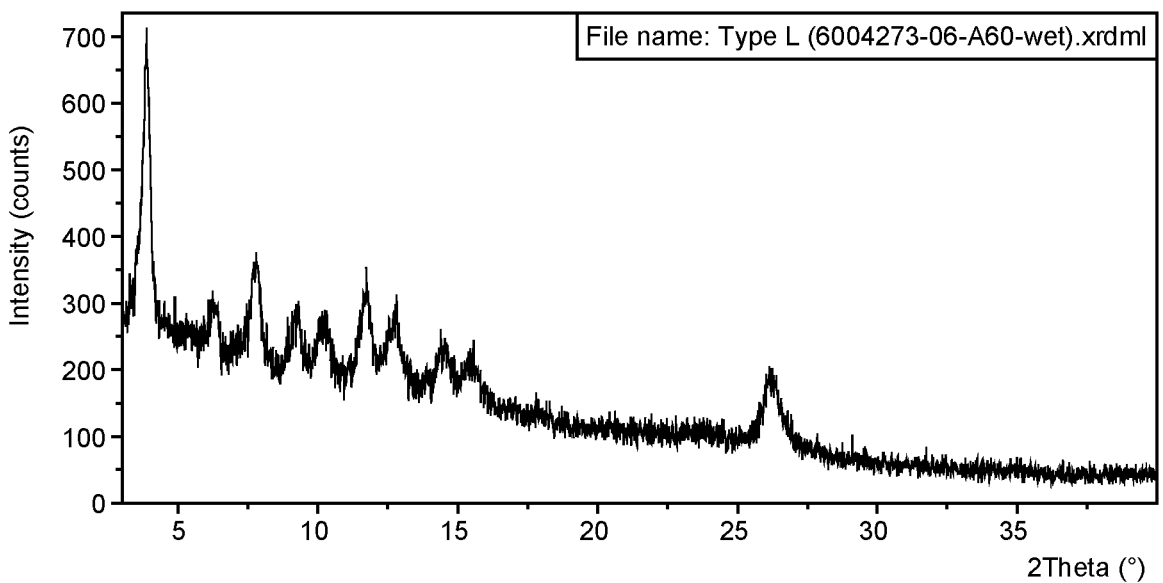
FIG. 61.

HM30181 mesylate Type L was obtained through antisolvent addition in DMF/n-propanol and DMA/isopropanol systems. By XRPD, HM30181 mesylate Type L is partially crystalline (see FIG. 61).

Figure 62:
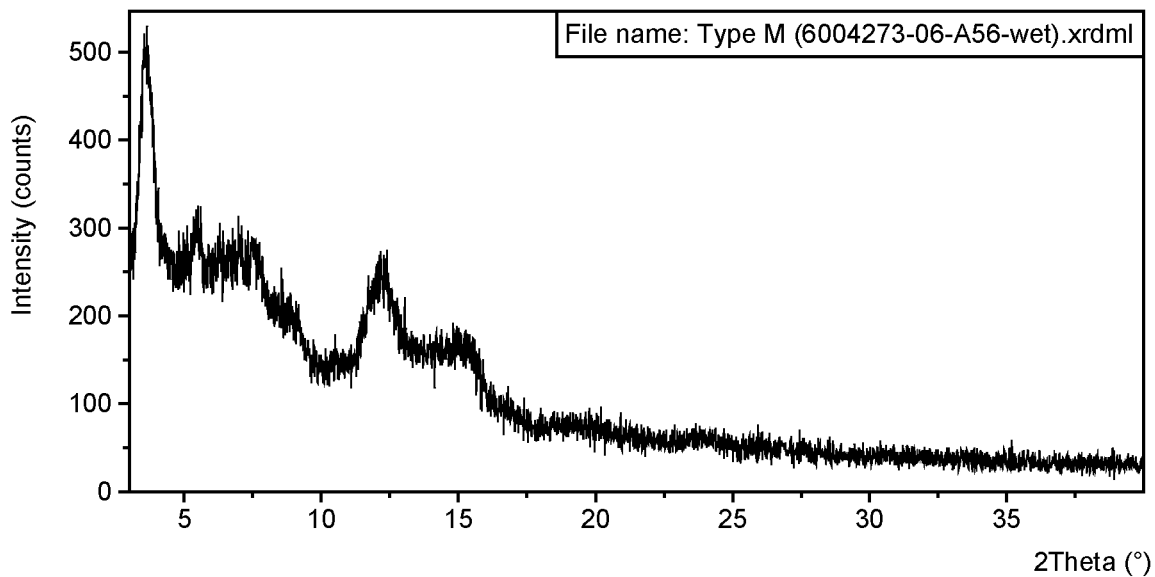
FIG. 62.

HM30181 mesylate type M was obtained through antisolvent addition in DMF/toluene and DMA/t-butanol systems. By XRPD, HM30181 mesylate Type M is partially crystalline (see FIG. 62).

Figure 63:
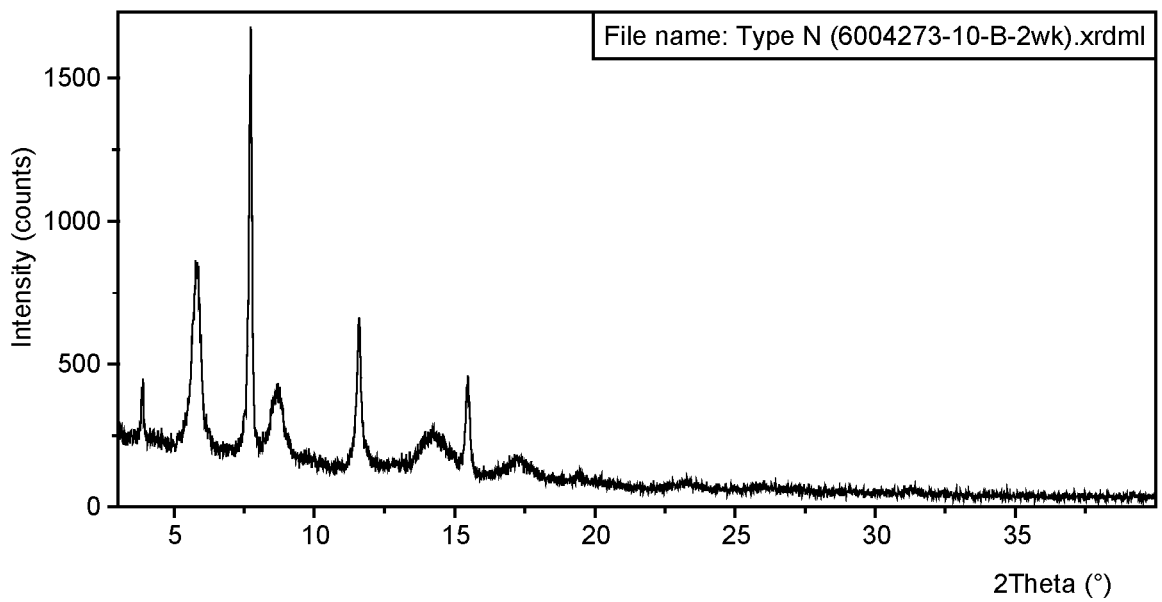
FIG. 63.
Figure 64:
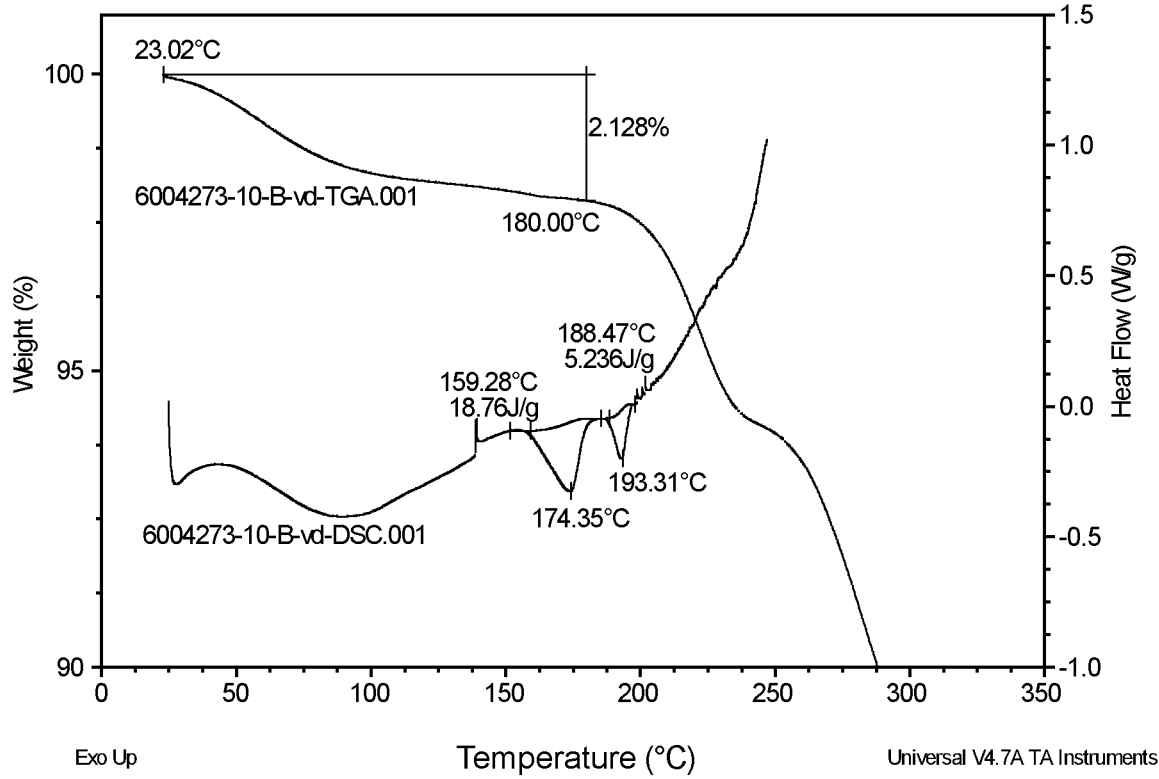
FIG. 64.
Figure 65:
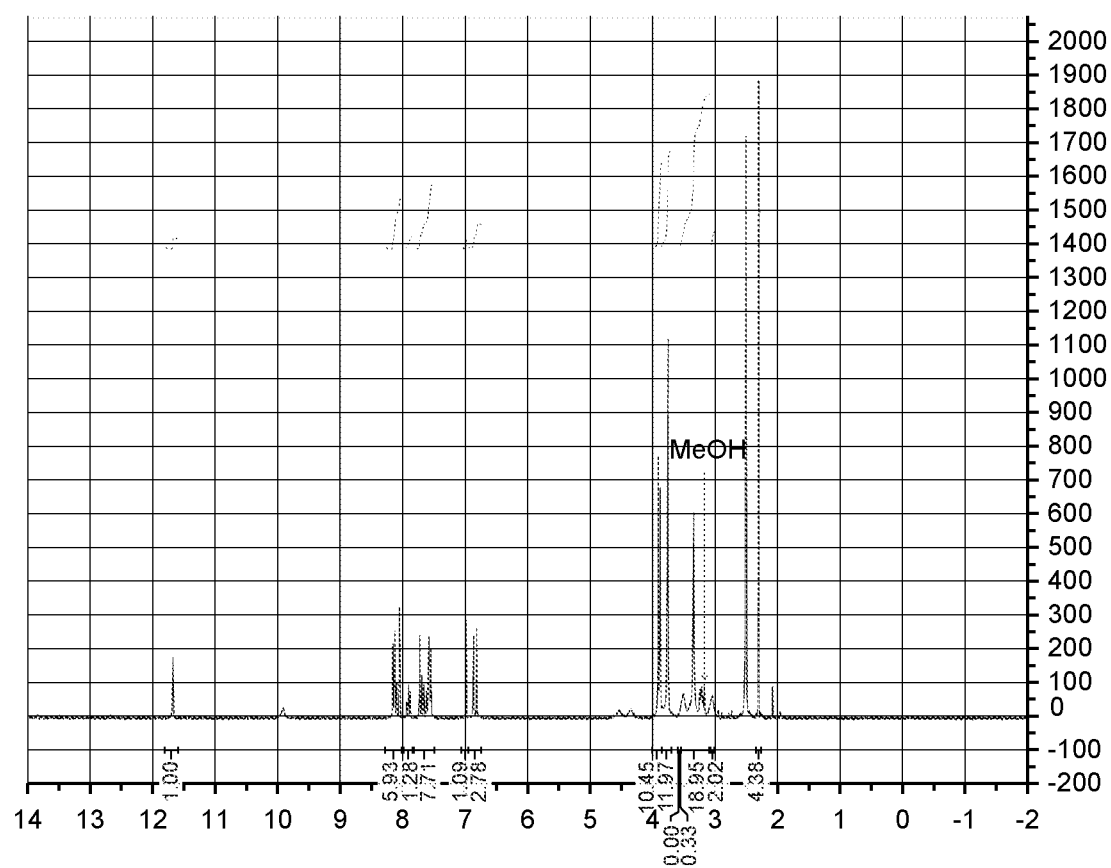
FIG. 65.

Crystalline HM30181 mesylate Type N was obtained after 14-days treatment of HM30181 mesylate Type A starting material as a slurry in methanol at ambient temperature (see FIG. 63). HM30181 mesylate Type N showed some loss of crystallinity after vacuum-drying, suggesting a methanol solvate. By DSC, HM30181 mesylate Type N displayed endotherms at 159.28° C. and 188.47° C. with a 2.128% weight loss before 180° C., followed by possible disassociation and decomposition (see FIG. 64). $^1$H-NMR confirmed the presence of methanol (see FIG. 65).

HM30181 mesylate Type C and E forms were further analyzed to determine unit cell dimensions. Unit cell parameters for the Type C polymorph of HM30181 mesylate were calculated using cumulative XRPD spectra, peak identifications for which are shown in Table 15. Notably distinct peaks for HM30181 mesylate Type C are shown in bold and italicized in Table 15. Estimated values of unit cell parameters derived from the Type C polymorph of HM30181 mesylate are shown in Table 16 and are consistent with triclinic P unit cells.

TABLE 15

| Pos. [°2Th.] | Height [cts] | FWHM Left [°2Th.] | d-spacing [Å] | Rel. Int. [%] |
|---|---|---|---|---|
| 3.5 | 34.6 | 0.05 | 25.5 | 1.8 |
| 5.1 | 95.5 | 0.115 | 17.5 | 5.0 |
| 5.6 | 30.2 | 0.08 | 15.8 | 1.6 |
| *6.4* | *419.6* | *0.08* | *13.7* | *22.2* |
| *8.0* | *1247.3* | *0.12* | *11.0* | *65.9* |
| 9.9 | 37.7 | 0.20 | 8.9 | 2.0 |
| 11.7 | 305.9 | 0.20 | 7.6 | 16.2 |
| 12.1 | 322.7 | 0.10 | 7.3 | 17.1 |
| 12.8 | 1892.0 | 0.10 | 6.9 | 100.0 |
| 13.9 | 205.8 | 0.13 | 6.4 | 10.9 |
| 15.0 | 609.3 | 0.13 | 5.9 | 32.2 |
| 15.5 | 113.8 | 0.82 | 5.7 | 6.0 |
| 16.1 | 253.9 | 0.15 | 5.5 | 13.4 |
| 17.8 | 71.2 | 0.46 | 5.0 | 3.8 |
| 19.2 | 439.5 | 0.20 | 4.6 | 23.2 |
| 19.7 | 590.3 | 0.20 | 4.5 | 31.2 |
| 20.0 | 362.7 | 0.20 | 4.4 | 19.2 |
| 21.2 | 60.7 | 0.10 | 4.2 | 3.2 |
| 22.1 | 20.0 | 0.10 | 4.0 | 1.0 |
| 22.9 | 309.0 | 0.13 | 3.9 | 16.3 |
| 23.4 | 99.7 | 0.18 | 3.8 | 5.3 |
| 24.5 | 37.2 | 0.20 | 3.6 | 2.0 |
| 25.1 | 63.6 | 0.31 | 3.6 | 3.4 |
| 26.1 | 1066.2 | 0.31 | 3.4 | 56.4 |
| 26.9 | 130.0 | 0.20 | 3.3 | 6.9 |
| 28.1 | 144.2 | 0.23 | 3.2 | 7.6 |
| 29.4 | 15.4 | 0.31 | 3.0 | 0.8 |
| 32.4 | 19.0 | 0.20 | 2.8 | 1.0 |
| 34.3 | 25.9 | 0.05 | 2.6 | 1.4 |
| 35.50 | 13.2 | 0.41 | 2.5 | 0.7 |
| 36.5 | 16.1 | 0.15 | 2.5 | 0.9 |
| 37.3 | 12.0 | 0.08 | 2.4 | 0.6 |

TABLE 16

| Reflection Conditions | |
|---|---|
| Crystal System | Triclinic |
| Bravais Type | Primitive (P) |
| Space Group | |
| Instrument Settings | |
| Goniometer Radius (mm) | 240.00 |
| Unit Cell | |
| a (Å) | 7.34 (2) |
| b (Å) | 14.6 (1) |
| c (Å) | 17.5 (8) |
| Alpha (°) | 51.8 (6) |
| Beta (°) | 62.3 (2) |
| Gamma (°) | 90.4 (3) |
| Volume (Å$^3$) | 1179.70 |
| Refinement Results | |
| No. Unindexed Lines | 0 |
| No. Indexed Lines | 17 |
| Total No. Calculated Lines | 5110 |
| Chi Square | 3.777537E−0006 |
| Snyder's FOM | 2.0791 |

Characteristic XRPD peak values for the Type E polymorph are provided in Table 17, where notably distinct peaks are indicated by bolded and italicized numerals. It should be appreciated that these are distinct and different from those of polymorph Type C, indicating that the Type C and Type E polymorphs are distinct and different from one another and that both Type C and Type E polymorphs are distinct and different from the prior art Type A polymorph of HM30181 mesylate.

TABLE 17

| Pos. [°2Th.] | Height [cts] | FWHM Left [°2Th.] | d-spacing [Å] | Rel. Int. [%] |
|---|---|---|---|---|
| *4.2* | *458.0* | *0.15* | *21.2* | *43.7* |
| 5.2 | 4.1 | 0.05 | 17.0 | 0.4 |
| 6.0 | 16.0 | 0.038 | 14.7 | 1.5 |
| 6.2 | 13.5 | 0.051 | 14.3 | 1.3 |
| 6.3 | 22.1 | 0.038 | 14.0 | 2.1 |
| 8.2 | 1047.3 | 0.15 | 10.8 | 100.0 |
| 9.0 | 35.8 | 0.038 | 9.9 | 3.4 |
| 9.1 | 29.7 | 0.15 | 9.7 | 2.8 |
| 9.9 | 13.9 | 0.05 | 9.0 | 1.3 |
| *10.4* | *344.2* | *0.13* | *8.5* | *32.9* |
| *10.7* | *430.1* | *0.15* | *8.3* | *41.1* |
| 11.6 | 136.8 | 0.20 | 7.6 | 13.1 |
| 12.3 | 114.7 | 0.18 | 7.2 | 11.0 |
| 12.9 | 170.3 | 0.15 | 6.9 | 16.3 |
| 13.6 | 30.8 | 0.15 | 6.5 | 2.9 |
| *14.7* | *685.3* | *0.26* | *6.0* | *65.4* |
| 15.4 | 227.7 | 0.13 | 5.7 | 21.8 |
| 15.9 | 801.8 | 0.23 | 5.6 | 76.6 |
| 16.3 | 46.5 | 0.15 | 5.4 | 4.4 |
| *16.8* | *827.7* | *0.13* | *5.3* | *79.0* |
| 17.7 | 281.7 | 0.20 | 5.0 | 26.9 |
| 18.3 | 200.1 | 0.23 | 4.9 | 19.1 |
| 18.9 | 298.0 | 0.20 | 4.7 | 28.4 |
| 19.3 | 164.2 | 0.13 | 4.6 | 15.7 |
| 19.6 | 106.5 | 0.13 | 4.5 | 10.2 |
| 20.0 | 103.1 | 0.15 | 4.4 | 9.8 |
| 20.4 | 153.2 | 0.13 | 4.3 | 14.6 |
| *21.0* | *842.3* | *0.22* | *4.2* | *80.4* |
| 21.3 | 320.9 | 0.13 | 4.2 | 30.6 |
| 21.6 | 243.7 | 0.10 | 4.1 | 23.3 |
| 22.0 | 111.1 | 0.20 | 4.0 | 10.6 |
| 22.4 | 128.7 | 0.15 | 4.0 | 12.3 |
| 22.7 | 418.2 | 0.26 | 3.9 | 39.9 |
| *23.8* | *272.6* | *0.26* | *3.7* | *26.0* |
| 24.1 | 116.9 | 0.10 | 3.7 | 11.2 |
| 24.6 | 174.5 | 0.20 | 3.6 | 16.7 |
| 24.9 | 214.9 | 0.18 | 3.6 | 20.5 |
| 26.2 | 994.9 | 0.15 | 3.4 | 95.0 |
| *26.6* | *965.7* | *0.15* | *3.3* | *92.2* |
| *27.7* | *343.3* | *0.20* | *3.2* | *32.8* |
| 28.3 | 94.3 | 0.18 | 3.2 | 9.0 |
| 28.8 | 20.2 | 0.15 | 3.1 | 1.9 |
| 29.3 | 62.1 | 0.15 | 3.0 | 5.9 |
| 30.7 | 45.9 | 0.20 | 2.9 | 4.4 |
| 32.1 | 117.5 | 0.18 | 2.8 | 11.2 |
| 33.3 | 40.2 | 0.15 | 2.7 | 3.8 |
| 33.9 | 42.7 | 0.31 | 2.6 | 4.1 |
| 34.7 | 33.4 | 0.26 | 2.6 | 3.2 |
| 35.7 | 22.6 | 0.20 | 2.5 | 2.2 |
| 37.0 | 29.8 | 0.15 | 2.4 | 2.8 |

Unit cell parameters for the Type E polymorph of HM30181 mesylate were calculated using cumulative XRPD spectra. Estimated values of unit cell parameters derived from the Type E polymorph of HM30181 mesylate are shown in Table 18 and are consistent with triclinic P unit cells.

TABLE 18

| Reflection Conditions | |
|---|---|
| Crystal System | Triclinic |
| Bravais Type | Primitive (P) |
| Space Group | |
| Instrument Settings | |
| Goniometer Radius (mm) | 240.00 |
| Unit Cell | |
| a (Å) | 8.2 (2) |
| b (Å) | 9.8 (2) |
| c (Å) | 23.7 (4) |
| Alpha (°) | 75.2 (2) |
| Beta (°) | 78.66 (3) |
| Gamma (°) | 111.69 (3) |
| Volume (Å$^3$) | 1618.45 |
| Refinement Results | |
| No. Unindexed Lines | 0 |
| No. Indexed Lines | 32 |
| Total No. Calculated Lines | 6088 |
| Chi Square | 8.802423E−0007 |
| Snyder's FOM | 5.7186 |

As noted above, HM30181 is an inhibitor of P-glycoprotein, an efflux transport protein that is effective at removing a wide range of therapeutic from cells and forms an important part of the blood brain barrier. While this function is essentially protective, it can adversely impact the use of therapeutic drugs that P-glycoprotein substrates. Examples of drugs that are transported by P-glycoprotein include, but are not limited to, antineoplastic drugs (e.g., docetaxel, etoposide, vincristine), calcium channel blockers (e.g., amlodipine), calcineurin inhibitors (e.g., cyclosporin, tacrolimus), digoxin, macrolide antibiotics (e.g., clarithromycin), and protease inhibitors. Accordingly, HM30181 mesylate can be used to alter the pharmacokinetics of therapeutic drug substrates of P-glycoprotein by reducing efflux of such drugs from the cells of an individual undergoing treatment.

Conventional process for the production of HM30181 provide the Type A polymorph. Inventors have produced and identified a number of other forms of this compound, including Type B, Type C, Type D, Type E, Type F, Type G, Type H, Type I, Type J, Type K, Type L, Type M, and Type N polymorphs of HM30181. As shown above, these are different and distinct from the prior art Type A polymorph and from each other. Inventors believe that these new polymorphs of HM30181 can provide different stabilities and/or pharmacokinetics (e.g., rate of absorption, etc.) than those provided by the prior art Type A polymorph.

Accordingly, another embodiment of the inventive concept is the application of one or more of a Type B, Type C, Type D, Type E, Type F, Type G, Type H, Type I, Type J, Type K, Type L, Type M, and/or Type N polymorph of HM30181 to inhibit P-glycoprotein, and in turn alter the pharmacokinetics of a drug that is a substrate of P-glycoprotein. In some of such embodiments the drug can be a chemotherapeutic drug used in the treatment of cancer.

In such embodiments one or more of a Type B, Type C, Type D, Type E, Type F, Type G, Type H, Type I, Type J, Type K, Type L, Type M, and/or Type N polymorph of HM30181 can be administered in concert with a drug that is a P-glycoprotein substrate to an individual that is in need of treatment for a disease or condition that is responsive to such a drug. In some embodiments a Type B, Type C, Type D, Type E, Type F, Type G, Type H, Type I, Type J, Type K, Type L, Type M, and/or Type N polymorph of HM30181 can be provided as a separate formulation. Alternatively, one or more of a Type B, Type C, Type D, Type E, Type F, Type G, Type H, Type I, Type J, Type K, Type L, Type M, and/or Type N polymorph of HM30181 can be formulated in combination with a drug that is a P-glycoprotein substrate. In a preferred embodiment the disease is cancer, and the drug that is a P-glycoprotein substrate is a chemotherapeutic drug used to treat cancer.

Methods

As noted above, polymorphs of HM30181 mesylate were provided by treatment of a conventional HM30181 mesylate Type A preparation with a variety of solvents, and using a range of techniques. For solubility studies of HM30181 mesylate Type A in a variety of solvents a sample (~2 mg) of the solid was transferred into a 4-mL glass vial. Solvent was added to the vial in a stepwise fashion, 50 µL per step until 100 µL total volume followed by 100 µL per step until concentration was less than 1.0 mg/mL. Samples were mixed thoroughly after each addition by sonication for 2 minutes and vortexing for 1 minute. Volumes of solvent (V1 and V2) were recorded and used to estimate solubility. Solvents used are summarized below in Table 19.

TABLE 19

| Abbreviation | Solvent | Abbreviation | Solvent |
|---|---|---|---|
| MeOH | Methanol | THF | Tetrahydrofuran |
| EtOH | Ethanol | 2-MeTHF | 2-Methyltetrahydrofuran |
| IPA | Isopropyl alcohol | DMF | Dimethyl formamide |
| ACN | Acetonitrile | DMSO | Dimethyl sulfoxide |
| MIBK | Methyl isobutyl ketone | CHCl$_3$ | Chloroform |
| EtOAc | Ethyl acetate | DCM | Dichloromethane |
| iPrOAc | Isopropyl acetate | DMAc | Dimethylacetamide |
| MTBE | Methyl tert-butyl ether | t-BuOH | t-Butanol |

Screening of polymorphisms of HM30181 mesylate can include preparation of a slurry. Typically, a slurry was prepared by suspending 5 mg to 20 mg of sample in 0.1 mL to 0.5 mL solvent in a 1.5 mL or 3.0 mL glass vial. The suspension a was stirred at target temperature (e.g. 4° C., ambient temperature, 50° C.) at 200 rpm. Solids for X-ray powder diffraction (XRPD) analysis were separated by centrifuging at 14,000 rpm for 5 minutes at ambient temperature. If no solid or gel is obtained, the slurry can be move to a fume hood for evaporation of the solvent.

In some embodiments anti-solvent addition was used. In this method a concentrated stock of compound in solvent is provided and an anti-solvent quickly added to the concentrated solution while stirring to induce precipitation. Solids can be isolated for XRPD analysis using filtration or centrifugation.

In some embodiments reverse anti-solvent addition was used. In this method a concentrated stock of compound in solvent is provided and quickly added to an anti-solvent with stirring to induce precipitation. Solids can be isolated for XRPD analysis using filtration or centrifugation.

In some embodiments slow cooling was used. In this method a concentrated suspension of compound in solvent is provided. This solution was heated to 50° C. and held at 50° C. for at least 30 minutes. The resulting solution or suspension was filtered at 50° C. using a 0.45 micron PTFE filter and the filtrate collected into clean vials. The resulting clear solution was cooled to 5° C. to induce precipitation. Solids were isolated solids for XRPD analysis using filtration or centrifugation.

In some embodiments crash cooling was used. In this method a concentrated suspension of compound in solvent is provided. The suspension was heated to 50° C. and held at 50° C. for at least 30 minutes. The heated solution or suspension was filtered at 50° C. using a 0.45 micron PTFE filter and the filtrate collected into clean vials. The clear solution was cooled to −20° C. to induce precipitation. Solids were isolated for XRPD analysis using filtration or centrifugation.

In some embodiments liquid vapor diffusion was used. In this method a concentrated stock of compound in solvent is provided. This concentrated stock is transferred to an inner vial that is sealed within a larger vial containing anti-solvent. Solids were isolated for XRPD analysis using filtration or centrifugation.

In some embodiments solid vapor diffusion was used. In this method 5-15 mg of sample were weighed into a small (e.g., 3 mL) vial. The vial was placed inside a larger vial (e.g., 20 mL) containing 3- to 4 mL of a volatile solvent. The outer vial was then sealed. This assembly was kept at ambient temperature for 7 days, allowing solvent vapor to interact with the solid, and the resulting product characterized by XRPD.

Unique HM30181 mesylate polymorphisms were characterized by a variety of techniques, including X-ray powder diffraction (XRPD), NMR, and calorimetry. These were performed as follows.

XRPD was performed using a Panalytical X'Pert3™ Powder XRPD and on a Si zero-background holder. The 2θ position was calibrated against a Panalytical™ 640 Si powder standard. Details of XRPD used in the experiments are listed below in Table 20.

TABLE 20

| | Parameters for Reflection Mode |
|---|---|
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0131 |
| Scan speed (°/s) | 0.16 |

Differential Scanning calorimetry (DSC) was performed using a TA Q2000™ DSC from TA Instruments. Temperature was ramped from ambient temperature to desired temperature at a heating rate of 10° C./min using N$_2$ as the purge gas, with pan crimped (see Table 21).

TABLE 21

| Parameters | DSC |
|---|---|
| Pan Type | Aluminum pan, closed |
| Temperature | ambient temperature-300° C. |
| Ramp rate | 10° C./min |
| Purge gas | N$_2$ |

In some studies, a cyclic DSC method was used. In such cycling DSC methods temperature was ramped from ambient to 150° C. at a heating rate of 10° C./min using N$_2$ as the purge gas, then cooled by 10° C. to 25° C. This temperature cycle repeated twice (see Table 22).

TABLE 22

| Parameters | DSC |
|---|---|
| Pan Type | Aluminum pan, closed |
| Temperature | 25-150° C. |
| Ramp rate | 10° C./min |
| Purge gas | N₂ |
| Heat/cool Cycles | 2 |

Thermogravimetric Analysis (TGA) was performed using a TA Q500™ TGA from TA Instruments. Temperature was ramped from ambient to desired temperature at a heating rate of 10° C./min using $N_2$ as the purge gas, with pan open (see Table 23).

TABLE 23

| Parameters | TGA |
|---|---|
| Pan Type | Platinum plate, open |
| Temperature | 300° C. |
| Ramp rate | 10° C./min |
| Purge gas | N₂ |
| Sample purge flow | 15 mL/min |
| Balance purge flow | 25 mL/min |

Dynamic Vapor Sorption (DVS) was measured using a SMS (Surface Measurement Systems™) DVS Intrinsic. Parameters for DVS test are listed below in Table 24.

TABLE 24

| Parameters | Values |
|---|---|
| Temperature | 25° C. |
| Sample size | 10-20 mg |
| Gas and flow rate | N₂, 200 mL/min |
| dm/dt | 0.002%/min |
| Min. dm/dt stability duration | 10 min |
| Max. equilibrium time | 360 min |
| RH range | 40% RH-95% RH-0% RH-95% RH |
| RH step size | 10% (0% RH-90% RH) |
|  | 5% (90% RH-95% RH) |

Proton NMR were obtained using a Varian 200M™ NMR in deuterated DMSO (DMSO-$d_6$).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A composition comprising a crystalline form of HM30181 mesylate wherein the crystalline form is polymorph C, and wherein the crystalline form has an X-ray diffraction pattern corresponding to FIG. 42 and has an endotherm at about 159.6° C.

2. A method of inhibiting P-glycoprotein activity, comprising contacting P-glycoprotein with the crystalline form of HM30181 mesylate of claim 1 in an amount effective to inhibit an activity of P-glycoprotein.

* * * * *